US012709770B2

(12) United States Patent
Yeo et al.

(10) Patent No.: US 12,709,770 B2
(45) Date of Patent: Aug. 18, 2026

(54) METHODS OF IDENTIFYING PROTEIN BINDING SITES ON RNA

(71) Applicant: The Regents of the University of California, Oakland, CA (US)

(72) Inventors: Eugene Yeo, La Jolla, CA (US); Meredith Corley, La Jolla, CA (US)

(73) Assignee: The Regents of the University of California, Oakland, CA (US)

( * ) Notice: Subject to any disclaimer, the term of this patent is extended or adjusted under 35 U.S.C. 154(b) by 557 days.

(21) Appl. No.: 18/027,478

(22) PCT Filed: Sep. 24, 2021

(86) PCT No.: PCT/US2021/051952
§ 371 (c)(1),
(2) Date: Mar. 21, 2023

(87) PCT Pub. No.: WO2022/067036
PCT Pub. Date: Mar. 31, 2022

(65) Prior Publication Data

US 2023/0374566 A1 Nov. 23, 2023

Related U.S. Application Data

(60) Provisional application No. 63/083,393, filed on Sep. 25, 2020.

(51) Int. Cl.
*C12Q 1/68* (2018.01)
*C07K 16/44* (2006.01)
*C12Q 1/6806* (2018.01)

(52) U.S. Cl.
CPC ............ *C12Q 1/6806* (2013.01); *C07K 16/44* (2013.01)

(58) Field of Classification Search
CPC ........................................................ C12Q 1/68
See application file for complete search history.

(56) References Cited

U.S. PATENT DOCUMENTS

| | | | |
|---|---|---|---|
| 12,139,710 | B2 | 11/2024 | Yeo et al. |
| 2011/0287412 | A1 | 11/2011 | Landthaler et al. |
| 2014/0378316 | A1 | 12/2014 | Darnell et al. |
| 2018/0073018 | A1 | 3/2018 | Hu et al. |
| 2022/0127611 | A1 | 4/2022 | Yeo et al. |
| 2024/0417730 | A1 | 12/2024 | Yeo et al. |

FOREIGN PATENT DOCUMENTS

| | | |
|---|---|---|
| WO | WO 2017/091630 | 6/2017 |
| WO | WO 2021/202542 | 10/2021 |

OTHER PUBLICATIONS

Belluci et al., Nature Methods 8(6), 444-445 (2011). (Year: 2011).*
Hu et al., "HIV-1 reverse transcription," Cold Spring Harbor Perspectives in Medicine, Oct. 1, 2012, 2(10): a006882.
Lou, "Large-scale activity assignment of RNA-interacting proteins identified a functional antagonist to fragile X mental retardation protein," Thesis for the degree of Doctor of Philosophy, University of California San Diego, School of Bioengineering, Oct. 2020, 24 pages.
Spitale et al., "RNA Shape analysis in living cells—Supplementary Information," Nature Chemical Biology, Nov. 25, 2012, 18 pages.
Van Nostrand et al., "Robust transcriptome-wide discovery of RNA-binding protein binding sites with enhanced CLIP (eCLIP)—Supplementary Material," Nature Methods, Mar. 28, 2016, 47 pages.
Aucagne et al., "UBAP2L is amplified in a large subset of human lung adenocarcinoma and is critical for epithelial lung cell identity and tumor metastasis," The FASEB Journal, Nov. 2017, 31(11):5012-5018.
Cook et al., "RBPDB: a database of RNA-binding specificities, " Nucleic Acids Research, Jan. 2011, 39:D301-D308.
Lino et al., "Delivering CRISPR: a review of the challenges and approaches, " Drug Delivery, Nov. 2018, 25(1):1234-1257.
Polstein et al., "A light-inducible CRISPR-Cas9 system for control of endogenous gene activation," Nature Chemical Biology, Mar. 2015, 11(3):198-200.
Andreev et al., "Translation control of mRNAs encoding mammalian translation initiation factors," Gene, Apr. 2018, 651:174-182.
Ashburner et al., "Gene Ontology: tool for the unification of biology," Nature Genetics, May 2000, 25:25-29.
Attwood et al., "PRINTS and its automatic supplement, prePRINTS," Nucleic Acids Research, Jan. 2003, 31(1):400-402.
Baltz et al., "The mRNA-Bound Proteome and Its Global Occupancy Profile on Protein-Coding Transcripts," Molecular Cell, Jun. 2012, 46(5):674-690.
Batra et al., "Elimination of Toxic Microsatellite Repeat Expansion RNA by RNA-Targeting Cas9," Cell, Aug. 2017, 170(5):899-912.
Beckmann et al., "The RNA-binding proteomes from yeast to man harbour conserved enigmRBPs," Nature Communications, Dec. 2015, 6(10127):1-9.
Benjamini et al., "Adaptive linear step-up procedures that control the false discovery rate," Biometrika, Sep. 2006, 93(3):491-507.
Bicknell et al., "When mRNA translation meets decay," Biochemical Society Transactions, Apr. 2017, 45(2):339-351.
Boelens et al., "The human UI snRNP-Specific UIA protein inhibits polyadenylation of its own pre-mRNA," Cell, Mar. 1993, 72(6):881-892.
Bos et al., "Tethered Function Assays as Tools to Elucidate the Molecular Roles of RNA-Binding Proteins," Advances in Experimental Medicine and Biology, Jun. 2016, 907:61-88.

(Continued)

*Primary Examiner* — Kenneth R Horlick
(74) *Attorney, Agent, or Firm* — Fish & Richardson P.C.

(57) ABSTRACT

Provided are methods for identifying an RNA nucleobase that interacts with an RNA binding protein (RBP) including (a) crosslinking the RNA binding protein to an RNA fragment in a biological sample; (b) detecting an RNA-RBP complex, wherein the RNA-RBP complex comprises the RNA fragment bound by the RNA binding protein; (c) isolating the RNA fragment of the RNA-RBP complex; and (d) profiling the isolated RNA fragment bound by the RNA binding protein, thereby identifying the RNA nucleobase of the RNA fragment that interacts with the RNA binding protein.

6 Claims, 33 Drawing Sheets

(56) References Cited

OTHER PUBLICATIONS

Brannan et al., "SONAR Discovers RNA-Binding Proteins from Analysis of Large-Scale Protein-Protein Interactomes," Molecular Cell, Oct. 2016, 64(2):282-293.
Busan et al., "Guidelines for SHAPE Reagent Choice and Detection Strategy for RNA Structure Probing Studies," Biochemistry, May 2019, 58:2655-2664.
Cano et al., "A non-proteolytic role for ubiquitin in deadenylation of MHC-I mRNA by the RNA-binding E3-ligase MEX-3C," Nature Communications, Oct. 2015, 6(8670):1-8.
Castello et al., "Comprehensive Identification of RNA-Binding Domains in Human Cells," Molecular Cell, Aug. 2016, 63(4):696-710.
Castello et al., "Insights into RNA Biology from an Atlas of Mammalian mRNA-Binding Proteins, " Cell, Jun. 2012, 149(6):1393-1406.
Chen et al., "Functional dissection of hnRNP D suggests that nuclear import is required before hnRNP D can modulate mRNA turnover in the cytoplasm," RNA, 2004, 10:669-680.
Cirillo et al., "UBAP2L Forms Distinct Cores that Act in Nucleating Stress Granules Upstream of G3BP1," Current Biology, Feb. 2020, 30(4):698-707.
Clement et al., "A Tethering Approach to Study Proteins that Activate mRNA Turnover in Human Cells, " Methods In Molecular Biology, 2008, 419:121-133.
Clery et al., "From Structure to Function of RNA Binding Domains," RNA Binding Proteins, 2011, 137-158.
Coller et al., "mRNA stabilization by poly(A) binding protein is independent of poly(A) and requires translation," Genes & Development, 1998, 12:3226-3235.
Coller et al., "Tethered function assays using 3' untranslated regions," Methods, Feb. 2002, 26(2):142-150.
Coller et al., "Tethered Function Assays: An Adaptable Approach to Study RNA Regulatory Proteins," Methods in Enzymology, 2007, 429:299-321.
Colombrita et al., "TDP-43 and FUS RNA-binding Proteins Bind Distinct Sets of Cytoplasmic Messenger RNAs and Differently Regulate Their Post-transcriptional Fate in Motoneuron-like Cells," Journal of Biological Chemistry, May 2012, 287(19):15635-15647.
Conway et al., "Enhanced CLIP Uncovers IMP Protein-RNA Targets in Human Pluripotent Stem Cells Important for Cell Adhesion and Survival," Cell Reports, Apr. 2016, 15(3):666-679.
Corley et al., "Footprinting SHAPE-eCLIP Reveals Transcriptome-wide Hydrogen Bonds at RNA-Protein Interfaces," Molecular Cell, Dec. 2020, 80(5):903-914.
Corley et al., "How RNA-Binding Proteins Interact with RNA: Molecules and Mechanisms," Molecular Cell, Apr. 2020, 78(1):9-29.
Cox et al., "RNA editing with CRISPR-Cas13," Science, Oct. 2017, 358(6366):1019-1027.
Deigan et al., "Accurate SHAPE-directed RNA structure determination," Proceedings of the National Academy of Sciences (PNAS), Jan. 2009, 106(1):97-102.
Deragon et al., "The role of LARP1 in translation and beyond," Wiley Interdisciplinary Reviews RNA, 2015, 6(4):399-417.
Di Sanzo et al., "shRNA targeting of ferritin heavy chain activates H19/miR-675 axis in K562 cells," Gene, May 2018, 657:92-99.
Ding et al., "In vivo genome-wide profiling of RNA secondary structure reveals novel regulatory features, " Nature, 2014, 505:696-700.
Diribarne et al., "7SK RNA, a non-coding RNA regulating P-TEFb, a general transcription factor," RNA Biology, Apr. 2009, 6(2):122-128.
Dobin et al., "STAR: ultrafast universal RNA-seq aligner," Bioinformatics, Jan. 2013, 29(1):15-21.
Doench et al., "Rational design of highly active sgRNAs for CRISPR-Cas9-mediated gene inactivation," Nature Biotechnology, Dec. 2014, 32(12):1262-1267.
Dominguez et al., "Sequence, Structure, and Context Preferences of Human RNA Binding Proteins, " Molecular Cell, Jun. 2018, 70(5):854-867.e9.
Duncan et al., "The Clk2 and Clk3 Dual-Specificity Protein Kinases Regulate the Intranuclear Distribution of SR Proteins and Influence Pre-mRNA Splicing," Experimental Cell Research, Jun. 1998, 241(2):300-308.
Feng et al., "Light-activated chemical probing of nucleobase solvent accessibility inside cells," Nature Chemical Biology, Jan. 2018, 14:276-283.
Fensterl et al., "Interferon-Induced Ifit Proteins: Their Role in Viral Pathogenesis," Journal of Virology, Mar. 2015, 89(5):2462-2468.
Fillebeen et al., "Electrophoretic Mobility Shift Assay (EMSA) for the Study of RNA-Protein Interactions: The IRE/IRP Example," Journal of Visualized Experiments, Dec. 2014, 94(e52230):1-9.
Fiorini et al., "Human Upfl is a highly processive RNA helicase and translocase with RNP remodelling activities," Nature Communications, Jul. 2015, 6(7581):1-10.
Fischer et al., "Structure-Mediated RNA Decay by UPF1 and G3BP1," Molecular Cell, Apr. 2020, 78(1):70-84.
Flores et al., "Structural Changes of RNA in Complex with Proteins in the SRP," Frontiers in Molecular Biosciences, Feb. 2018, 5(7):1-8.
Flynn et al., "Transcriptome-wide interrogation of RNA secondary structure in living cells with icSHAPE," Nature Protocols, Jan. 2016, 11(2):273-290.
Fu et al., "DAZ Family Proteins, Key Players for Germ Cell Development," International Journal of Biological Sciences, 2015, 11(10):1226-1235.
Fujii et al., "Decoding the Function of Expansion Segments in Ribosomes," Molecular Cell, Dec. 2018, 72(6):1013-1020.
Garneau et al., "The highways and byways of mRNA decay," Nature Reviews Molecular Cell Biology, Feb. 2007, 8:113-126.
Gehman et al., "The splicing regulator Rbfox1 (A2BP1) controls neuronal excitation in the mammalian brain," Nature Genetics, May 2011, 43(7):706-711.
Gerstberger et al., "A census of human RNA-binding proteins," Nature Reviews Genetics, Nov. 2014, 15(12):829-845.
Gerstberger et al., "Evolutionary Conservation and Expression of Human RNA-Binding Proteins and Their Role in Human Genetic Disease," Advances in Experimental Medicine Biology, Aug. 2014, 825:1-55.
Graham et al., "Resources for the design of CRISPR gene editing experiments," Genome Biology, Nov. 2015, 16(260):1-21.
Graindorge et al., "In-cell identification and measurement of RNA-protein interactions, " Nature Communication, Nov. 2019, 10(5317):1-11.
Gray et al., "Cardiac Hypertrophy: A tail of translational regulation," Elife, Jun. 2017, 6(e29104):1-4.
Hafner et al., "Transcriptome-wide Identification of RNA-Binding Protein and MicroRNA Target Sites by PAR-CLIP, " Cell, Apr. 2010, 141(1):129-141.
Hainzl et al., "Structural insights into SRP RNA: An induced fit mechanism for SRP assembly," RNA, May 2005, 11:1043-1050.
Hanson et al., "Translation elongation and mRNA stability are coupled through the ribosomal A-site, " RNA, 2018, 24:1377-1389.
Hockensmith et al., "Laser cross-linking of nucleic acids to proteins. Methodology and first applications to the phage T4 DNA replication system," Journal of Biological Chemistry, Mar. 1986, 261(8):3512-3518.
Hu et al., "A structural dissection of protein-RNA interactions based on different RNA base areas of interfaces, " RSC Advances, 2018, 8:10582-10592.
Hu et al., "Cpeb4-Mediated Translational Regulatory Circuitry Controls Terminal Erythroid Differentiation," Development Cell, Sep. 2014, 30(6):660-672.
International Preliminary Report on Patentability in International Appln. No. PCT/US2021/051952, mailed on Apr. 6, 2023, 9 pages.
International Search Report and Written Opinion in International Appln. No. PCT/US2021/051952, dated Jan. 18, 2022, 11 pages.
Jackson et al., "The mechanism of eukaryotic translation initiation and principles of its regulation," Nature Reviews Molecular Cell Biology, Feb. 2010, 11:113-127.

(56) References Cited

OTHER PUBLICATIONS

Julaton et al., "NANOS3 function in human germ cell development," Human Molecular Genetics, Jun. 2011, 20(11):2238-2250.
Kapeli et al., "Distinct and shared functions of ALS-associated proteins TDP-43, FUS and TAF15 revealed by multisystem analyses," Nature Communications, Jul. 2016, 7(12143):1-14.
Kazan et al., "RNAcontext: A New Method for Learning the Sequence and Structure Binding Preferences of RNA-Binding Proteins," PLoS Computational Biology, Jul. 2010, 6(7):e1000832.
Konig et al., "iCLIP reveals the function of hnRNP particles in splicing at individual nucleotide resolution," Nature Structural & Molecular Biology, Jul. 2010, 17(7):909-915.
Lackey et al., "Allele-specific SHAPE-MaP assessment of the effects of somatic variation and protein binding on mRNA structure," RNA, Jan. 2018, 24:513-528.
Le Quesne et al., "Derivation of a structural model for the c-myc IRES," Journal of Molecular Biology, Jun. 2001, 310(1):111-126.
Lee et al., "Advances in CLIP Technologies for Studies of Protein-RNA Interactions," Molecular Cell, Feb. 2018, 69(3):354-369.
Lee et al., "Integrative analysis reveals RNA G-quadruplexes in UTRs are selectively constrained and enriched for functional associations," Nature Communications, Jan. 2020, 11(527):1-12.
Leppek et al., "Functional 5' UTR mRNA structures in eukaryotic translation regulation and how to find them," Nature Reviews Molecular Cell Biology, 2018, 19:158-174.
Leulliot et al., "Current Topics in RNA—Protein Recognition: Control of Specificity and Biological Function through Induced Fit and Conformational Capture," Biochemistry, 2001, 40(27):7947-7956.
Levi et al., "Neurodegeneration with Brain Iron Accumulation Disorders: Valuable Models Aimed at Understanding the Pathogenesis of Iron Deposition," Pharmaceuticals, 2019, 12(1):27.
Li et al., "The Sequence Alignment/Map format and SAMtools," Bioinformatics, Aug. 2009, 25(16):2078-2079.
Liang et al., "Stepping Out of the Cytosol: AIMp1/p43 Potentiates the Link Between Innate and Adaptive Immunity," International Reviews of Immunology, Sep. 2015, 34(5):367-381.
Licatalosi et al., "HITS-CLIP yields genome-wide insights into brain alternative RNA processing," Nature, Nov. 2008, 456:464-469.
Liu et al., "Characterizing inactive ribosomes in translational profiling," Translation, 2016, 4(1):e1138018.
Lorenz et al., "ViennaRNA Package 2.0," Algorithms for Molecular Biology, Nov. 2011, 6(26):1-14.
Lotfi et al., "RNA secondary structure prediction based on SHAPE data in helix regions," Journal of Theoretical Biology, Sep. 2015, 380:178-182.
Loughlin et al., "The Solution Structure of FUS Bound to RNA Reveals a Bipartite Mode of RNA Recognition with Both Sequence and Shape Specificity," Molecular Cell, Feb. 2019, 73(3):490-504.e6.
Lovci et al., "Rbfox proteins regulate alternative mRNA splicing through evolutionarily conserved RNA bridges," Nature Structural & Molecular Biology, Nov. 2013, 20:1434-1442.
Love et al., "Moderated estimation of fold change and dispersion for RNA-seq data with DESeq2," Genome Biology, Dec. 2014, 15(550):1-21.
Low et al., "SHAPE-directed RNA secondary structure prediction," Methods, Oct. 2010, 52(2):150-158.
Lu et al., "RNA Duplex Map in Living Cells Reveals Higher-Order Transcriptome Structure," Cell, May 2016, 165(5):1267-1279.
Lukong et al., "RNA-binding proteins in human genetic disease," Trends in Genetics, Aug. 2008, 24(8):416-425.
Luna et al., "New clues to understand the role of THO and other functionally related factors in mRNP biogenesis," Biochimica et Biophysica Acta (BBA), Jun. 2012, 1819(6):514-520.
Luo et al., "Large-scale tethered function assays identify factors that regulate mRNA stability and translation," Nature Structural & Molecular Biology, Oct. 2020, 27(10):989-1000.
Lutz et al., "The snRNP-free U1A (Sf-A) complex(es): Identification of the largest subunit as PSF, the polypyrimidine-tract binding protein-associated splicing factor," RNA, Dec. 1998, 4(12):1493-1499.
Lykke-Andersen et al., "Recruitment and activation of mRNA decay enzymes by two ARE-mediated decay activation domains in the proteins TTP and BRF-1," Genes & Development, 2005, 19:351-361.
Maeda et al., "Arginine methylation of ubiquitin-associated protein 2-like is required for the accurate distribution of chromosomes," FASEB Journal, 2016, 30:312-323.
Markmiller et al., "Context-Dependent and Disease-Specific Diversity in Protein Interactions within Stress Granules," Cell, Jan. 2018, 172(3):590-604.
Martin et al., "Systematic reconstruction of RNA functional motifs with high-throughput microfluidics, " Nature Methods, 2012, 9(12):1192-1194.
Martin, "Cutadapt Removes Adapter Sequences From High-Throughput Sequencing Reads, " EMBnet.journal, 2011, 17(1):10-12.
Martinez et al., "Protein-RNA Networks Regulated by Normal and ALS-Associated Mutant HNRNPA2B1 in the Nervous System," Neuron, Nov. 2016, 92(4):780-795.
Maticzka et al., "GraphProt: modeling binding preferences of RNA-binding proteins," Genome Biology, Janauary 2014, 15(R17):1-18.
McDonald et al., "Satisfying Hydrogen Bonding Potential in Proteins," Journal of Molecular Biology, May 1994, 238(5):777-793.
McGinnis et al., "High-Throughput SHAPE and Hydroxyl Radical Analysis of RNA Structure and Ribonucleoprotein Assembly," Methods in Enzymology, 2009, 468:67-89.
Meng et al., "Cytoplasmic Metadherin (MTDH) Provides Survival Advantage under Conditions of Stress by Acting as RNA-binding Protein," Journal of Biological Chemistry, Feb. 2012, 287(7):4485-4491.
Meng et al., "Drug Resistance Mediated by AEG-1/MTDH/LYRIC," Advances in Cancer Research, 2013, 120:135-157.
Miyasaka et al., "Interaction of antiproliferative protein Tob with the CCR4-NOT deadenylase complex," Cancer Science, Apr. 2008, 99(4):755-761.
Moore et al., "Human Pumilio-2 is expressed in embryonic stem cells and germ cells and interacts with DAZ (Deleted in AZoospermia) and DAZ-like proteins, "Proceedings of the National Academy of Sciences (PNAS), Jan. 2003,100(2):538-543.
Mukhopadhyay et al., "The GAIT system: a gatekeeper of inflammatory gene expression," Trends in Biochemistry Sciences, Jul. 2009, 34(7):324-331.
Mustoe et al., "RNA base-pairing complexity in living cells visualized by correlated chemical probing," Proceedings of the National Academy of Sciences (PNAS), Nov. 2019, 116(49):24574-24582.
Natchiar et al., "Visualization of chemical modifications in the human 80S ribosome structure," Nature, Nov. 2017, 551:472-477.
Nelles et al., "Programmable RNA Tracking in Live Cells with CRISPR/Cas9," Cell, Apr. 2016, 165(2):488-496.
Nishimura et al., "The eIF4E-Binding Protein 4E-T Is a Component of the mRNA Decay Machinery that Bridges the 5' and 3' Termini of Target mRNAs," Cell Reports, Jun. 2015, 11(9):1425-1436.
O'Connell et al., "Programmable RNA recognition and cleavage by CRISPR/Cas9," Nature, Sep. 2014, 516:263-266.
Pan et al., "Prediction of RNA-protein sequence and structure binding preferences using deep convolutional and recurrent neural networks," BMC Genomics, Jul. 2018, 19(511): 1-11.
Popovic et al., "Iron accumulation and iron-regulatory protein activity in human hepatoma (HepG2) cells," Molecular and Cellular Biochemistry, Oct. 2004, 265:37-45.
Poria et al., "RNA-protein UV-crosslinking Assay," Bio-Protocol, Mar. 2017, 7(6):e2193.
Protter et al., "Principles and Properties of Stress Granules," Trends in Cell Biology, Sep. 2016, 26(9):668-679.
Punta et al., "The Pfam protein families database," Nucleic Acids Research, Jan. 2012, 40(D1):D290-D301.

(56) References Cited

OTHER PUBLICATIONS

Queiroz et al., "Comprehensive identification of RNA-protein interactions in any organism using orthogonal organic phase separation (OOPS)," Nature Biotechnology, Jan. 2019, 37:169-178.
Quinlan et al., "BEDTools: a flexible suite of utilities for comparing genomic features," Bioinformatics, Mar. 2010, 26(6):841-842.
Radhakrishnan et al., "Connections Underlying Translation and mRNA Stability," Journal of Molecular Biology, Sep. 2016, 428(18):3558-3564.
Ramachandran et al., "Statistical Analysis of SHAPE-Directed RNA Secondary Structure Modeling," Biochemistry, 2013, 52(4):596-599.
Rissland, "The organization and regulation of mRNA-protein complexes," Wiley Interdisciplinary Reviews RNA, 2017, 8:e1369.
Rosario et al., "RNA-binding proteins in human oogenesis: Balancing differentiation and self-renewal in the female fetal germline," Stem Cell Research, May 2017, 21:193-201.
Roy et al., "The intimate relationships of mRNA decay and translation," Trends in Genetics, Dec. 2013, 29(12):691-699.
Rual et al., "Human ORFeome Version 1.1: A Platform for Reverse Proteomics," Genome Research, 2004, 14:2128-2135.
Saria et al., "Discovering Deformable Motifs in Continuous Time Series Data," Proceedings of the Twenty-Second International Joint Conference on Artificial Intelligence, 2011, 2:1465-1471.
Schmidt et al., "SUnSET, a nonradioactive method to monitor protein synthesis," Nature Methods, 2009, 6:275-277.
Scotti et al., "RNA mis-splicing in disease," Nature Reviews Genetics, 2016, 17:19-32.
Siegfried et al., "RNA motif discovery by SHAPE and mutational profiling (SHAPE-MaP), " Nature Methods, Jul. 2014, 11:959-965.
Smith et al., "UMI-tools: modeling sequencing errors in Unique Molecular Identifiers to improve quantification accuracy," Genome Research, Jan. 2017, 27:491-499.
Smola et al., "Detection of RNA-Protein Interactions in Living Cells with SHAPE," Biochemistry, 2015, 54(46):6867-6875.
Smola et al., "In-cell RNA structure probing with SHAPE-MaP," Nature Protocols, 2018, 13(6):1181-1195.
Smola et al., "Selective 2'-hydroxyl acylation analyzed by primer extension and mutational profiling (SHAPE-MaP) for direct, versatile and accurate RNA structure analysis," Nature Protocols, Oct. 2015, 10(11):1643-1669.
Smola et al., "SHAPE reveals transcript-wide interactions, complex structural domains, and protein interactions across the Xist IncRNA in living cells," Proceedings of the National Academy of Sciences (PNAS), Aug. 2016, 113(37):10322-10327.
Spitale et al., "RNA SHAPE analysis in living cells," Nature Chemical Biology, Jan. 2013, 9:18-20.
Spitale et al., "Structural imprints in vivo decode RNA regulatory mechanisms," Nature, Mar. 2015, 519:486-490.
Stevens et al., "Two covariance models for iron-responsive elements," RNA Biology, 2011, 8(5):792-801.
Stys et al., "Iron Regulatory Protein 1 Outcompetes Iron Regulatory Protein 2 in Regulating Cellular Iron Homeostasis in Response to Nitric Oxide," Journal of Biological Chemistry, Jul. 2011, 286(26):22846-22854.
Sugimoto et al., "hiCLIP reveals the in vivo atlas of mRNA secondary structures recognized by Staufen 1," Nature, Mar. 2015, 519:491-494.
Sundararaman et al., "Resources for the Comprehensive Discovery of Functional RNA Elements," Molecular Cell, Mar. 2016, 61(6):903-913.
Tan et al., "Structure of Histone mRNA Stem-Loop, Human Stem-Loop Binding Protein, and 3'hExo Ternary Complex," Science, Jan. 2013, 339(6117):318-321.
The Gene Ontology Consortium, "Expansion of the Gene Ontology knowledgebase and resources," Nucleic Acids Research, Jan. 2017, 45(D1):D331-D338.
Tian et al., "Structural basis for piRNA 2'-O-methylated 3'-end recognition by Piwi PAZ (Piwi/Argonaute/Zwille) domains," Proceedings of the National Academy of Sciences (PNAS), Jan. 2011, 108(3):903-910.
Tijerina et al., "DMS footprinting of structured RNAs and RNA-protein complexes," Nature Protocols, Oct. 2007, 2:2608-2623.
Trendel et al., "The Human RNA-Binding Proteome and Its Dynamics during Translational Arrest," Cell, Jan. 2019, 176:391-403.
Ule et al., "An RNA map predicting Nova-dependent splicing regulation," Nature, Nov. 2006, 444:580-586.
Ule et al., "CLIP Identifies Nova-Regulated RNA Networks in the Brain," Science, Nov. 2003, 302(5648):1212-1215.
Urano et al., "Interaction of the conserved meiotic regulators, BOULE (BOL) and PUMILIO-2 (PUM2)," Molecular Reproduction & Development, Apr. 2005, 71(3):290-298.
Urdaneta et al., "Purification of cross-linked RNA-protein complexes by phenol-toluol extraction," Nature Communications, Mar. 2019, 10(990):1-17.
Van Nostrand et al., "A large-scale binding and functional map of human RNA-binding proteins, " Nature, Jul. 2020, 583:711-719.
Van Nostrand et al., "Experimental and Computational Considerations in the Study of RNA-Binding Protein-RNA Interactions," Advances in Experimental Medicine and Biology, 2016, 907:1-28.
Van Nostrand et al., "Principles of RNA processing from analysis of enhanced CLIP maps for 150 RNA binding proteins," Genome Biology, Apr. 2020, 21(90):1-26.
Van Nostrand et al., "Robust transcriptome-wide discovery of RNA-binding protein binding sites with enhanced CLIP (eCLIP)," Nature Methods, Mar. 2016, 13(6):508-514.
Vicens et al., "Revisiting the Closed-Loop Model and the Nature of mRNA 5'-3' Communication," Molecular Cell, Dec. 2018, 72(5):805-812.
Walden et al., "Accommodating variety in iron-responsive elements: Crystal structure of transferrin receptor 1 B Ire bound to iron regulatory protein 1," FEBS Letters, Jan. 2012, 586(1):32-35.
Walden et al., "Structure of Dual Function Iron Regulatory Protein 1 Complexed with Ferritin IRE-RNA," Science, Dec. 2006, 314(5807):1903-1908.
Wang et al., "Mechanistic studies of a small-molecule modulator of SMN2 splicing," Proceedings of the National Academy of Sciences (PNAS), May 2018, 115(20):E4606-E4612.
Wang et al., "N6-methyladenosine-dependent regulation of messenger RNA stability," Nature, 2014, 505:117-120.
Wheeler et al., "Advances and challenges in the detection of transcriptome-wide protein-RNA interactions," Wiley Interdisciplinary Reviews RNA, 2018, 9:e1436.
Wilkinson et al., "Selective 2'-hydroxyl acylation analyzed by primer extension (SHAPE): quantitative RNA structure analysis at single nucleotide resolution," Nature Protocols, Nov. 2006, 1(3):1610-1616.
Williams et al., "Structural insights into E1 recognition and the ubiquitin-conjugating activity of the E2 enzyme Cdc34," Nature Communications, Jul. 2019, 10(3296):1-15.
Yang et al., "Solution structure of the LicT-RNA antitermination complex: CAT clamping RAT," The EMBO Journal, Apr. 2002, 21(8):1987-1997.
Youn et al., "High-Density Proximity Mapping Reveals the Subcellular Organization of mRNA-Associated Granules and Bodies," Molecular Cell, Feb. 2018, 69(3):517-532.
Zubradt et al., "DMS-MaPseq for genome-wide or targeted RNA structure probing in vivo," Nature Methods, 2017, 14:75-82.
Burmistrz et al., "RNA-Targeting CRISPR-Cas Systems and Their Applications," International Journal of Molecular Sciences, Feb. 7, 2020, 21(3):1122.

* cited by examiner

Normalize -protein to +protein = 'fSHAPE' reactivity profile in protein binding sites.

fSHAPE

| Model | AUC | θ (A) |
| --- | --- | --- |
| BaseP < θ AND BaseR >= θ | 0.823 | 3.0 |
| BaseP < θ | 0.681 | 4.1 |
| BaseP < θ AND SugarP < θ | 0.648 | 2.9 |
| (BaseP < θ OR SugarP < θ) AND BaseR >= θ | 0.768 | 3.0 |
| BaseP < θ AND BaseP < θ AND BaseR >= θ | 0.843 | 4.1 |

SLBP binding site validation

| Dataset | % histone mRNAs | % overlap with ENCODE | Random % overlap with ENCODE |
|---|---|---|---|
| ENCODE | 80.36 | --- | --- |
| SHAPE-eCLIP (DMS) | 90.55 | 77.20 | 0.08+0.07 |
| SHAPE-eCLIP (NAI) | 53.48 | 38.90 | 0.07-0.08 |
| fSHAPE-eCLIP | 72.97 | 54.10 | 0.08+0.09 |

Stem Loop

AAAGGCUCUYUUM eCLIP Crosslink Rate (%*10)

fSHAPE

Histone mRNAs

Average

Position around SL motif

FIG.6B

METHODS OF IDENTIFYING PROTEIN BINDING SITES ON RNA

CROSS-REFERENCE TO RELATED APPLICATION

This application is a National Stage Application under 35 U.S.C. § 371 and claims the benefit of International Application No. PCT/US2021/051952, filed Sep. 24, 2021, which claims priority to U.S. Application No. 63/083,393, filed Sep. 25, 2020, the disclosure of which is incorporated herein by reference.

BACKGROUND

Understanding the interaction mechanism and location of RNA binding proteins (RBPs) on RNA is critical for understanding gene expression regulation. However, identification of precise nucleobases of RNA that hydrogen bond with protein in a transcriptome-wide manner remains technically challenging.

SUMMARY

The present disclosure is based, at least in part, on identifying RNA nucleobases that hydrogen bond with a protein.

Provided herein are methods of identifying an RNA nucleobase that interacts with an RNA binding protein (RBP), the method comprising: crosslinking the RNA binding protein to an RNA fragment in a biological sample; detecting an RNA-RBP complex, wherein the RNA-RBP complex comprises the RNA fragment bound by the RNA binding protein; isolating the RNA fragment of the RNA-RBP complex; and profiling the isolated RNA fragment bound by the RNA binding protein, thereby identifying the RNA nucleobase of the RNA fragment that interacts with the RNA binding protein. In some embodiments, the RNA nucleobase interacts with the RNA binding protein via hydrogen bond. In some embodiments, the crosslinking comprises formaldehyde crosslinking, UV crosslinking, psoralen crosslinking, or combinations thereof. In some embodiments, the biological sample comprises: a first plurality of cells, wherein the first plurality of cells is contacted with a RNA structure probing reagent prior to the crosslinking step; and a second plurality of cells, wherein the second plurality of cells is contacted with the RNA structure probing reagent after the isolating step. In some embodiments, the detecting step further comprises contacting the RNA-RBP complex with an RBP specific antibody, and immunoprecipitating the RNA-RBP complex with the RBP specific antibody. In some embodiments, the isolating step further comprises treating the immunoprecipitated RNA-RBP complex with a protease. In some embodiments, the profiling step further comprises sequencing all or a part of a sequence of the isolated RNA fragment or a complement thereof. In some embodiments, the sequencing comprises high-throughput sequencing. In some embodiments, the RNA structure probing reagent comprises 2-methylnicotinic acid imidazolide (NAI), dimethyl sulfate (DMS), 1-methyl-7-nitroisatoic anhydride (1M7), 1-methyl-6-nitroisatoic anhydride (1M6), N-methylisatoic anhydride (NMIA), 2-methylnicotinic acid imidazolide-azide (NAI-N3), Nicotinoyl azide (NaZ), Nicotinoyl azide (NaZ-N3), 2-aminopyridine-3-carboxylic acid imidazolide (2A3), Carbodiimide N-cyclohexyl-N'-(2-morpholinoethyl)carbodiimide metho-p-toluenesulfonate (CMC), Isoquinoline-6-carboxylic acid imidazolide (I6), Indoline-5-carboxylic acid imidazolide (I5), 1-Methylimidazole-4-carboxylic acid imidazolide (1M4), 6-Aminopyridine-3-carboxylic acid imidazolide (6A3), Benzotriazole-5-carboxylic acid imidazolide (B5), Nicotinic acid imidazolide (NIC), 3-Azaisatoic anhydride (3AIA), 2-methyl-3-furoic acid imidazolide (FAI), 2-methyl-3-furoic acid imidazolide-azide (FAI-N3), N-propanone isatoic anhydride (NPIA), 5-nitroisatoic anhydride (5NIA), azido-kethoxal (N3-kethoxal), Glyoxal, Methylglyoxal, Phenylglyoxal, 1-ethyl-3-(3-dimethylaminopropyl) carbodiimide (EDC), 4'-aminomethyltrioxalen (AMT), Psoralen-triethylene glycol azide, or Amotosalen. In some embodiments, the RNA structure probing reagent comprises 2-methylnicotinic acid imidazolide (NAI). In some embodiments, the biological sample comprises a tissue, a tissue section, an organ, an organism, an organoid, or a cell culture sample. In some embodiments, the biological sample comprises live cells from a cell culture. In some embodiments, the biological sample comprises a frozen tissue sample.

Further provided herein are methods of identifying an RNA nucleobase that interacts with an RNA binding protein (RBP), the method comprising: providing a biological sample, wherein the biological sample comprises a first plurality of cells and a second plurality of cells; contacting the first plurality of cells with an RNA structure probing agent; crosslinking the RNA binding protein to an RNA fragment in the biological sample; detecting an RNA-RBP complex, wherein the RNA-RBP complex comprises the RNA fragment bound by the RNA binding protein; isolating the RNA fragment of the RNA-RBP complex; contacting the RNA fragment from the second plurality of cells with the RNA structure probing agent; and profiling (i) the RNA fragment bound by the RNA binding protein from the first plurality of cells and (ii) the RNA fragment bound by the RNA binding protein from second plurality of cells, thereby identifying the RNA nucleobase of the RNA fragment that interacts with the RNA binding protein. In some embodiments, the RNA nucleobase interacts with the RNA binding protein via hydrogen bond. In some embodiments, the crosslinking comprises formaldehyde crosslinking, UV crosslinking, psoralen crosslinking, or combinations thereof. In some embodiments, the detecting step further comprises contacting the RNA-RBP complex with an RBP specific antibody, and immunoprecipitating the RNA-RBP complex using the RBP specific antibody. In some embodiments, the isolating step further comprises treating the immunoprecipitated RNA-RBP complex with a protease. In some embodiments, the profiling step further comprises sequencing all or a part of a sequence of the isolated RNA fragment or a complement thereof. In some embodiments, the sequencing comprises high-throughput sequencing. In some embodiments, the RNA structure probing reagent comprises 2-methylnicotinic acid imidazolide (NAI), dimethyl sulfate (DMS), 1-methyl-7-nitroisatoic anhydride (1M7), 1-methyl-6-nitroisatoic anhydride (1M6), N-methylisatoic anhydride (NMIA), 2-methylnicotinic acid imidazolide-azide (NAI-N3), Nicotinoyl azide (NaZ), Nicotinoyl azide (NaZ-N3), 2-aminopyridine-3-carboxylic acid imidazolide (2A3), Carbodiimide N-cyclohexyl-N'-(2-morpholinoethyl)carbodiimide metho-p-toluenesulfonate (CMC), Isoquinoline-6-carboxylic acid imidazolide (I6), Indoline-5-carboxylic acid imidazolide (I5), 1-Methylimidazole-4-carboxylic acid imidazolide (1M4), 6-Aminopyridine-3-carboxylic acid imidazolide (6A3), Benzotriazole-5-carboxylic acid imidazolide (B5), Nicotinic acid imidazolide (NIC), 3-Azaisatoic anhydride (3AIA), 2-methyl-3-furoic acid imidazolide (FAI), 2-methyl-3-furoic acid imidazolide-azide (FAI-N3), N-propanone isatoic anhydride (NPIA), 5-nitroisatoic anhydride (5NIA), azido-kethoxal (N3-kethoxal), Glyoxal, Methylglyoxal, Phenylglyoxal, 1-ethyl-3-(3-dimethylaminopropyl) carbodiimide (EDC), 4'-aminomethyltrioxalen (AMT), Psoralen-triethylene glycol azide, or Amotosalen. In some embodiments, the RNA structure probing reagent is 2-methylnicotinic acid imidazolide (NAI). In some embodiments, the biological sample comprises a tissue, a tissue section, an organ, an organism, an organoid, or a cell culture sample. In some embodiments, the biological sample comprises live cells from a cell culture. In some embodiments, the biological sample comprises a frozen tissue sample.

Further provided herein are methods of identifying hydrogen bond interactions between an RNA molecule and an RNA binding protein (RBP), the method comprising: crosslinking the RNA binding protein to an RNA fragment in a biological sample; detecting an RNA-RBP complex, wherein the RNA-RBP complex comprises the RNA fragment bound by the RNA binding protein; isolating the RNA fragment of the RNA-RBP complex; and profiling the isolated RNA fragment bound by the RNA binding protein, thereby identifying a hydrogen bond interaction between an RNA nucleobase and the RNA binding protein. In some embodiments, the RNA nucleobase interacts with the RNA binding protein via hydrogen bond. In some embodiments, the crosslinking comprises formaldehyde crosslinking, UV crosslinking, psoralen crosslinking, or combinations thereof. In some embodiments, the biological sample comprises: a first plurality of cells, wherein the first plurality of cells is contacted with a RNA structure probing reagent prior to the crosslinking step; and a second plurality of cells, wherein the second plurality of cells is contacted with the RNA structure probing reagent after the isolating step. In some embodiments, the detecting step further comprises contacting the RNA-RBP complex with an RBP specific antibody, and immunoprecipitating the RNA-RBP complex with the RBP specific antibody. In some embodiments, the isolating step further comprises treating the immunoprecipitated RNA-RBP complex with a protease. In some embodiments, the profiling step further comprises sequencing all or a part of a sequence of the isolated RNA fragment or a complement thereof. In some embodiments, the sequencing comprises high-throughput sequencing. In some embodiments, the RNA structure probing reagent comprises 2-methylnicotinic acid imidazolide (NAI), dimethyl sulfate (DMS), 1-methyl-7-nitroisatoic anhydride (1M7), 1-methyl-6-nitroisatoic anhydride (1M6), N-methylisatoic anhydride (NMIA), 2-methylnicotinic acid imidazolide-azide (NAI-N3), Nicotinoyl azide (NaZ), Nicotinoyl azide (NaZ-N3), 2-aminopyridine-3-carboxylic acid imidazolide (2A3), Carbodiimide N-cyclohexyl-N'-(2-morpholinoethyl)carbodiimide metho-p-toluenesulfonate (CMC), Isoquinoline-6-carboxylic acid imidazolide (I6), Indoline-5-carboxylic acid imidazolide (I5), 1-Methylimidazole-4-carboxylic acid imidazolide (IM4), 6-Aminopyridine-3-carboxylic acid imidazolide (6A3), Benzotriazole-5-carboxylic acid imidazolide (B5), Nicotinic acid imidazolide (NIC), 3-Azaisatoic anhydride (3AIA), 2-methyl-3-furoic acid imidazolide (FAI), 2-methyl-3-furoic acid imidazolide-azide (FAI-N3), N-propanone isatoic anhydride (NPIA), 5-nitroisatoic anhydride (5NIA), azido-kethoxal (N3-kethoxal), Glyoxal, Methylglyoxal, Phenylglyoxal, 1-ethyl-3-( 3-dimethylaminopropyl)carbodiimide (EDC), 4'-aminomethyltrioxalen (AMT), Psoralen-triethylene glycol azide, or Amotosalen. In some embodiments, the RNA structure probing reagent comprises 2-methylnicotinic acid imidazolide (NAD. In some embodiments, the biological sample comprises a tissue, a tissue section, an organ, an organism, an organoid, or a cell culture sample. In some embodiments, the biological sample comprises live cells from a cell culture. In some embodiments, the biological sample comprises a frozen tissue sample.

Further provided herein are kits comprising: an RBP specific antibody, wherein the RBP specific antibody binds to an RNA binding protein bound to an RNA fragment in a biological sample, thereby facilitating immunoprecipitation of an RNA-RBP complex using the RBP specific antibody, wherein the RNA-RBP complex comprises the RNA fragment bound by the RNA binding protein; an RNA structure probing agent; a protease, and instructions to use the kit to identify an RNA nucleobase that interacts with the RNA binding protein. In some embodiments, the instructions comprise instructions to crosslink the RNA binding protein to the RNA fragment in the biological sample, thereby producing the RNA-RBP complex. In some embodiments, the crosslinking comprises formaldehyde crosslinking, UV crosslinking, psoralen crosslinking, or combinations thereof. In some embodiments, the RNA structure probing reagent comprises 2-methylnicotinic acid imidazolide (NAI), dimethyl sulfate (DMS), 1-methyl-7-nitroisatoic anhydride (1M7), 1-methyl-6-nitroisatoic anhydride (1M6), N-methylisatoic anhydride (NMIA), 2-methylnicotinic acid imidazolide-azide (NAI-N3), Nicotinoyl azide (NaZ), Nicotinoyl azide (NaZ-N3), 2-aminopyridine-3-carboxylic acid imidazolide (2A3), Carbodiimide N-cyclohexyl-N'-(2-morpholinoethyl)carbodiimide metho-p-toluenesulfonate (CMC), Isoquinoline-6-carboxylic acid imidazolide (I6), Indoline-5-carboxylic acid imidazolide (I5), 1-Methylimidazole-4-carboxylic acid imidazolide (1M4), 6-Aminopyridine-3-carboxylic acid imidazolide (6A3), Benzotriazole-5-carboxylic acid imidazolide (B5), Nicotinic acid imidazolide (NIC), 3-Azaisatoic anhydride (3AIA), 2-methyl-3-furoic acid imidazolide (FAI), 2-methyl-3-furoic acid imidazolide-azide (FAI-N3), N-propanone isatoic anhydride (NPIA), 5-nitroisatoic anhydride (5NIA), azido-kethoxal (N3-kethoxal), Glyoxal, Methylglyoxal, Phenylglyoxal, 1-ethyl-3-(3-dimethylaminopropyl)carbodiimide (EDC), 4'-aminomethyltrioxalen (AMT), Psoralen-triethylene glycol azide, or Amotosalen. In some embodiments, the RNA structure probing agent is 2-methylnicotinic acid imidazolide (NAI).

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

26 Å in length with protein and do not form hydrogen bonds with other RNA moieties within 3.0 Å.

Figures 3A, 3B, 3C:
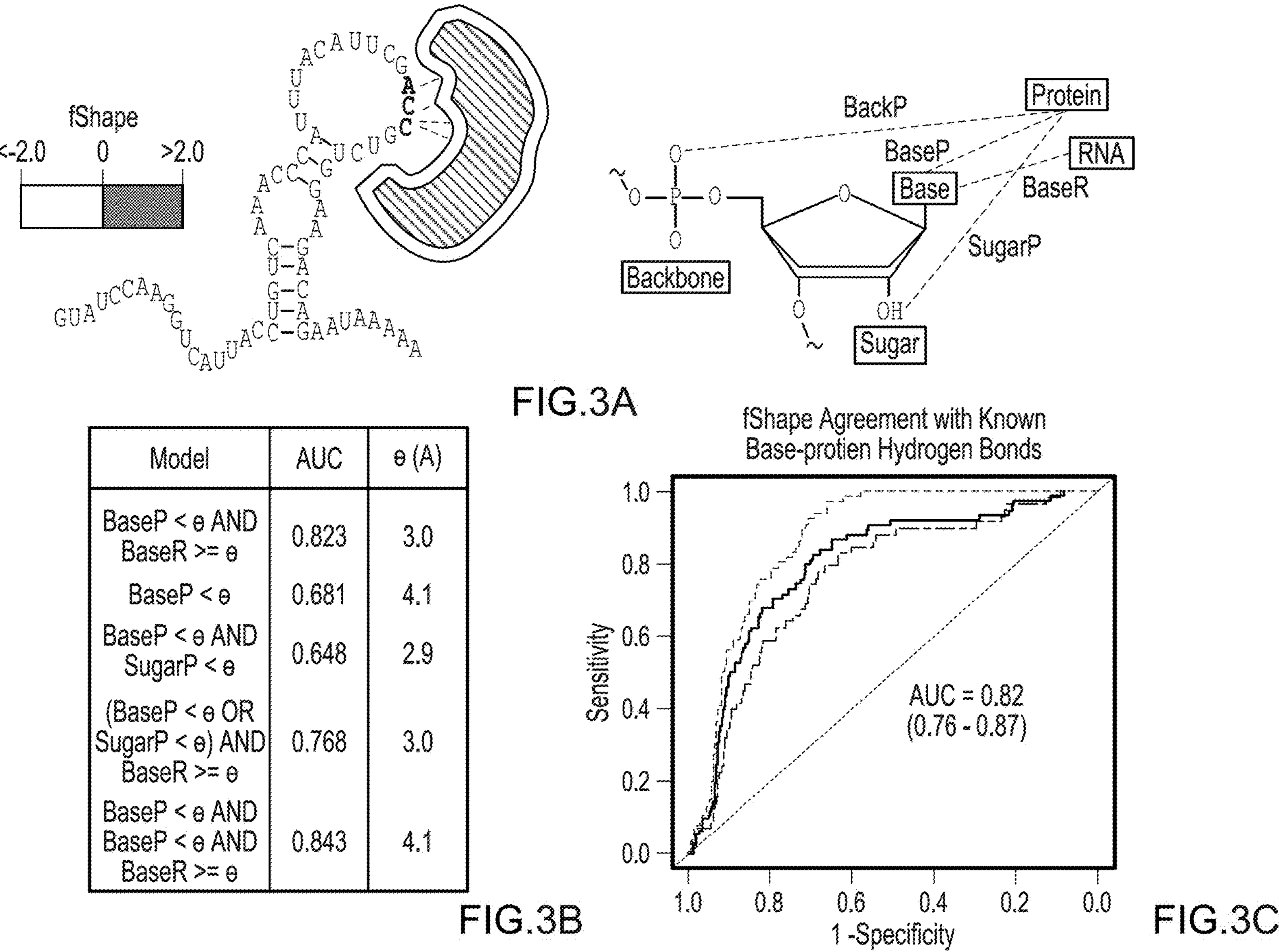
FIG. 3A shows an exemplary schematic of nucleotides known to interact with protein, wherein the nucleotides tend to correlate with high fSHAPE reactivities, likely determined by the combination of protein hydrogen bonds (dashed lines) with the backbone, base, and 2'-OH RNA moieties as well as pairing between RNA bases. This set of hydrogen bonds can be quantified in RNA-protein crystal structures as hydrogen bond lengths "BackP", "BaseP", "SugarP", and "BaseR", respectively.
FIG. 3B shows models made up of combinations of hydrogen bonds lengths were constructed to describe each nucleotide in human RNA-protein crystal structures and bond length threshold (q) was adjusted to maximize models' fit to corresponding fSHAPE reactivities. Models were fit to fSHAPE with receiver operator characteristic (ROC) curves; maximum area under the curve (AUC) and corresponding q in angstroms (A) shown for each model. The best model indicates excellent agreement between high fSHAPE reactivities and nucleotides whose base moieties form hydrogen bonds under 3.0

FIG. 3C shows the ROC curve of the model with best agreement between fSHAPE reactivities and crystal structure hydrogen bonds and bounding ROC curves from cross-validation. AUC of each curve indicated.

Figure 4A:
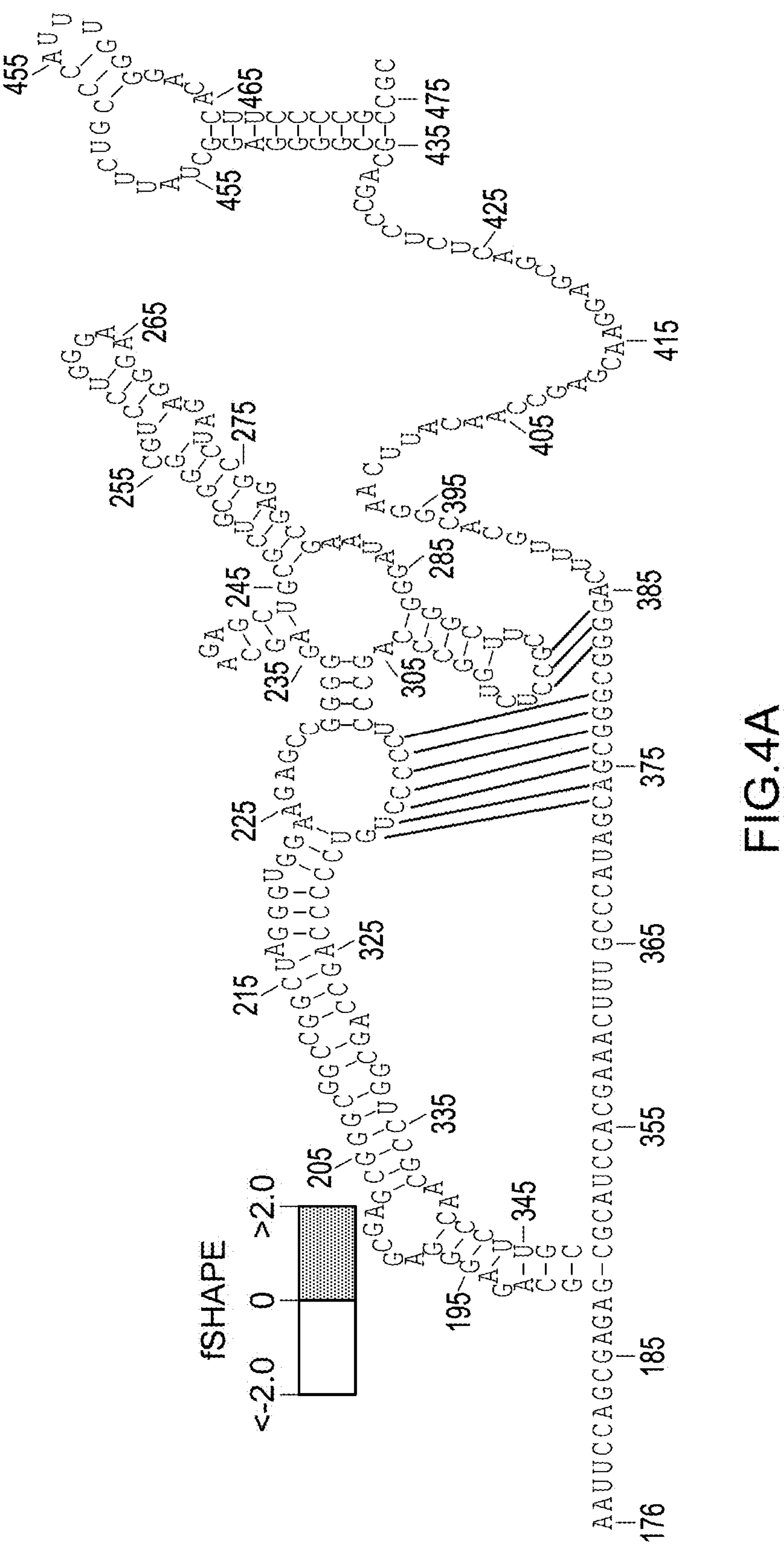

FIG. 4A shows an exemplary schematic of a functional RNA structure, the internal ribosome entry site (IRES) of human MYC (c-myc), overlaid with corresponding fSHAPE reactivities in K562 cells. Nucleotides numbered by position in MYC transcript NM_002467.

Figures 4B, 4C:
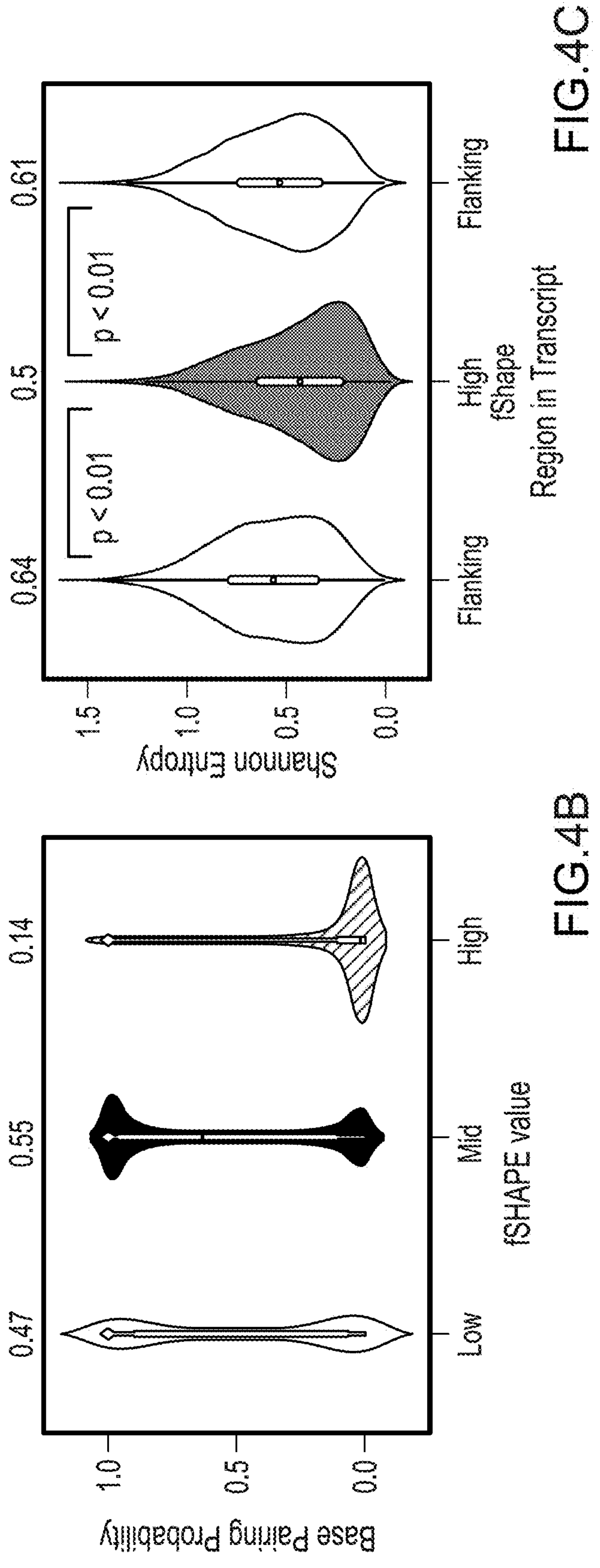

FIG. 4B shows predicted base pairing probability densities for nucleotides grouped by low, medium, and high fSHAPE reactivities. Median and interquartile range displayed in white. Average base pairing probability indicated above each group.

FIG. 4C shows Shannon entropy values predicted for 50-nucleotide regions containing high fSHAPE reactivities compared to 50-nucleotide flanking regions show a downward shift in Shannon entropy ($p<0.01$). Average Shannon entropy indicated above each type of region.

Figure 5A:
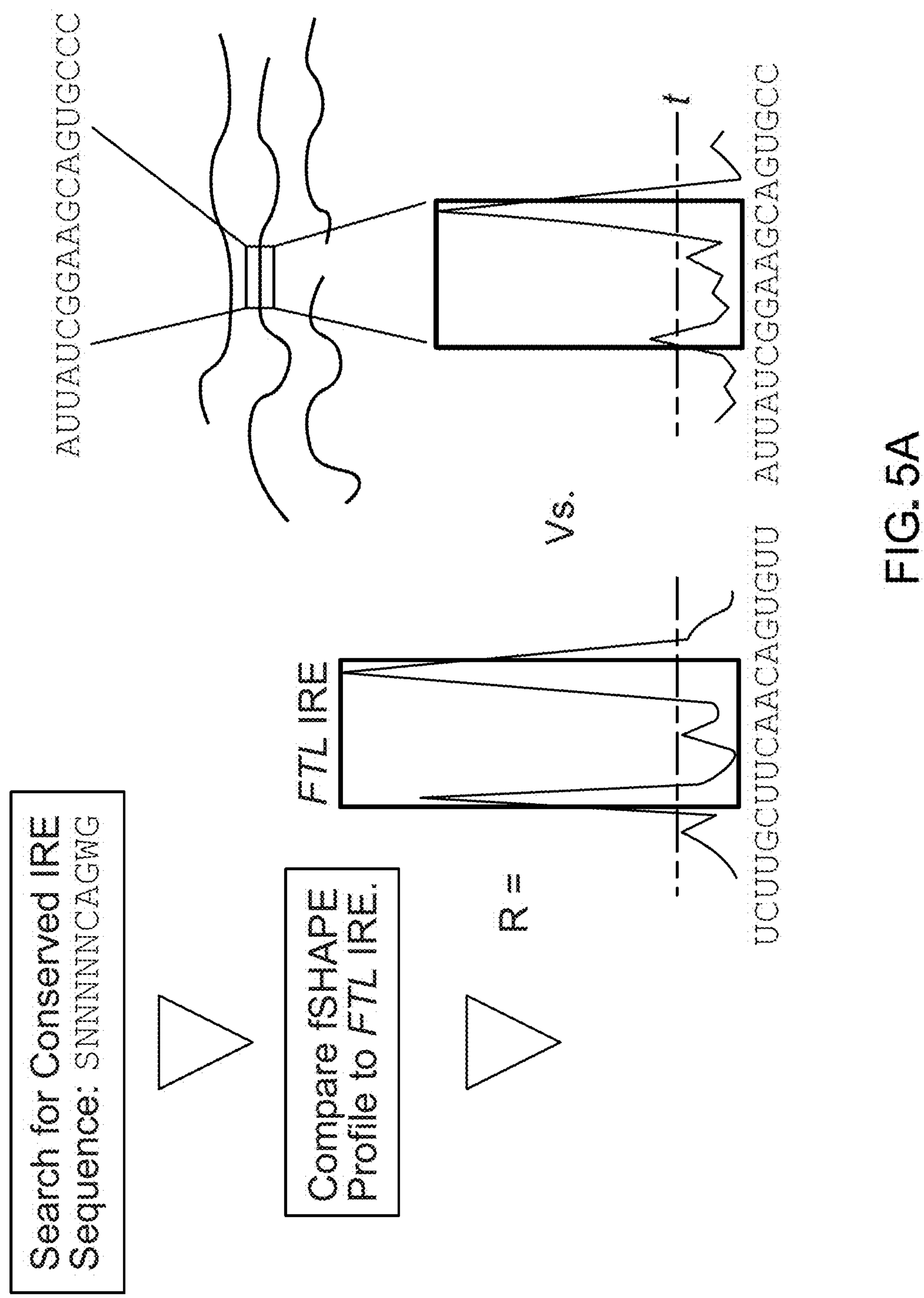

FIG. 5A shows an exemplary simple workflow for discovering new IREs. Transcript sequences that match the conserved IRE sequence and have fSHAPE data are compared to the FTL IRE's fSHAPE profile via correlation coefficient (R). R above 0.8 and fSHAPE reactivities at key positions above threshold t (dashed line) are selected as candidate IREs.

Figure 5B:
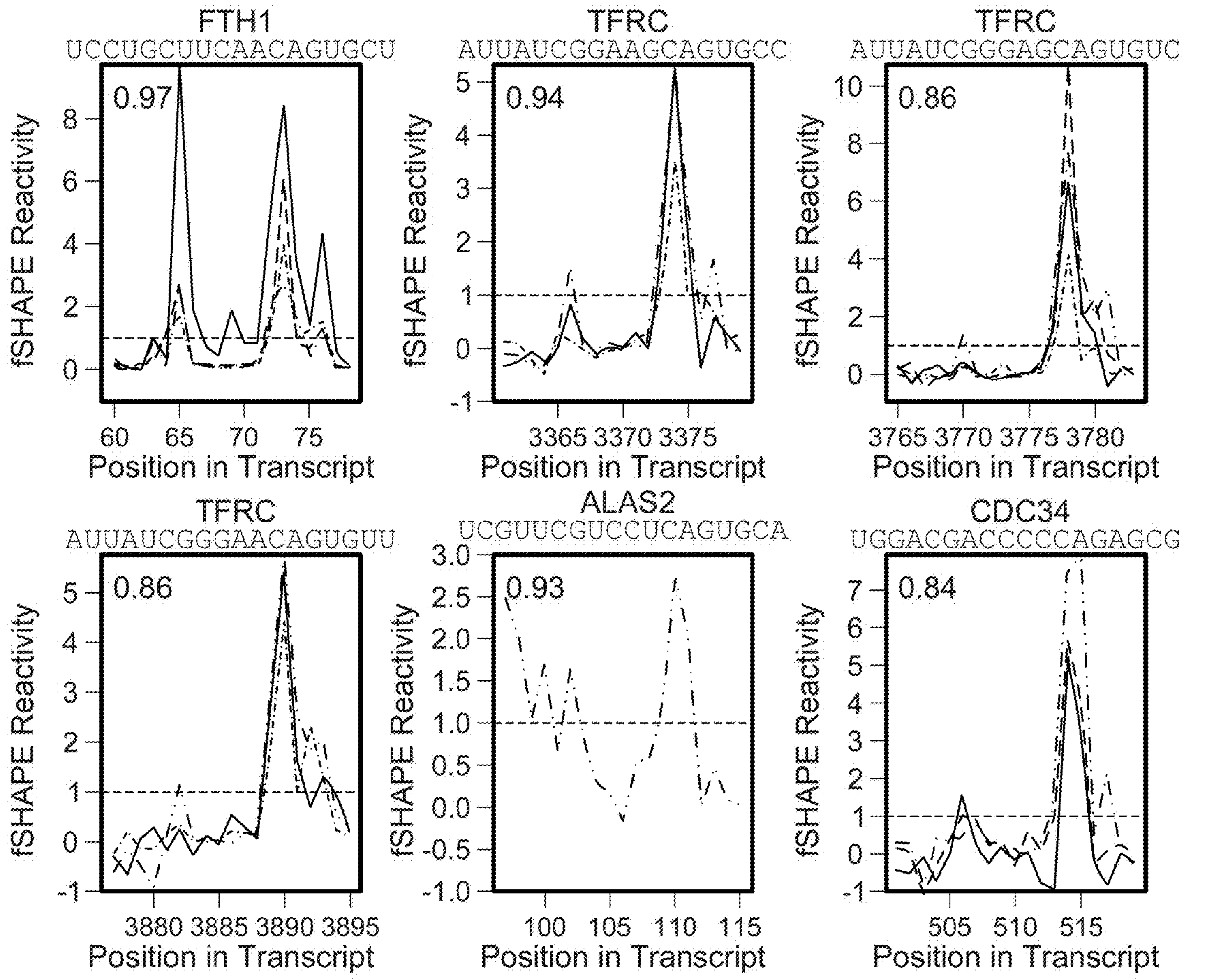
Figure 5B:
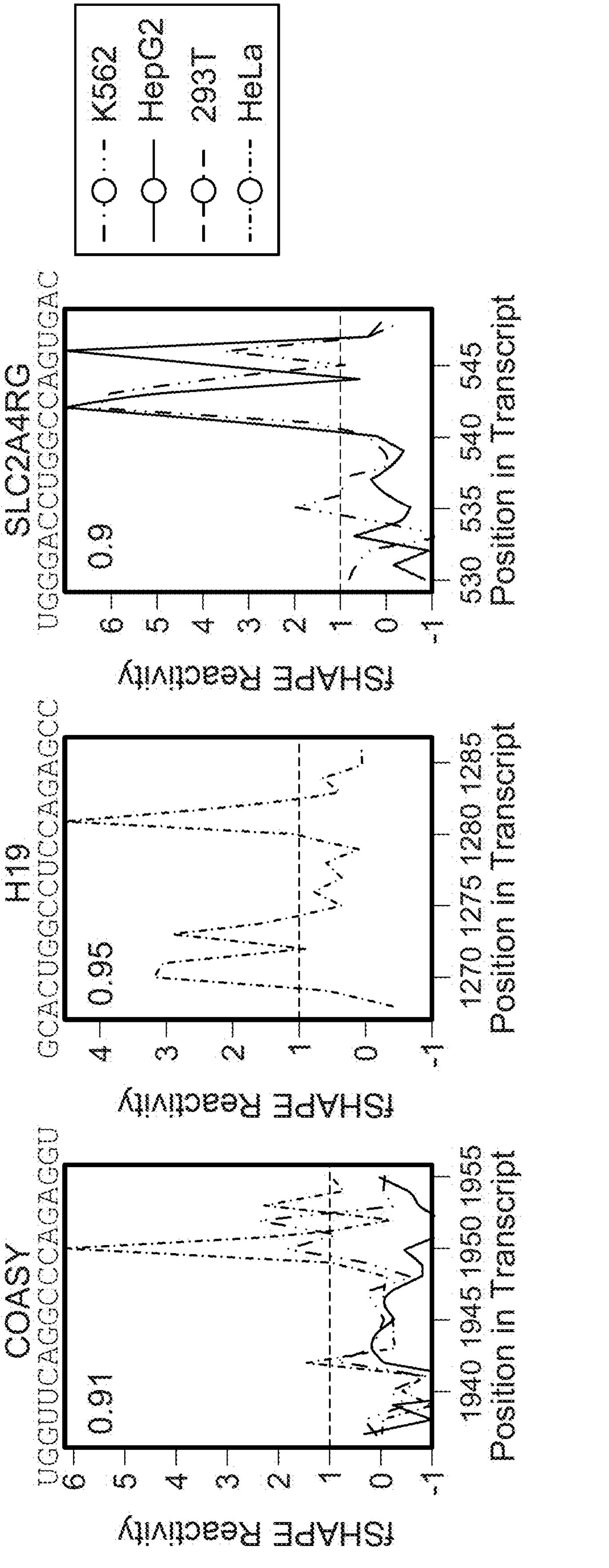

FIG. 5B shows selected fSHAPE profiles of IREs predicted by the workflow. Pearson correlation compared to FTL is indicated in top left corner, gene name and sequence indicated above each plot. IREs in FTH1, TFRC, and ALAS2 (top row) have been previously verified; predicted IREs in CDC34, COASY, H19, and SLC2A4RG (bottom row) are novel. Threshold (t) indicated with dashed line.

Figure 5C:
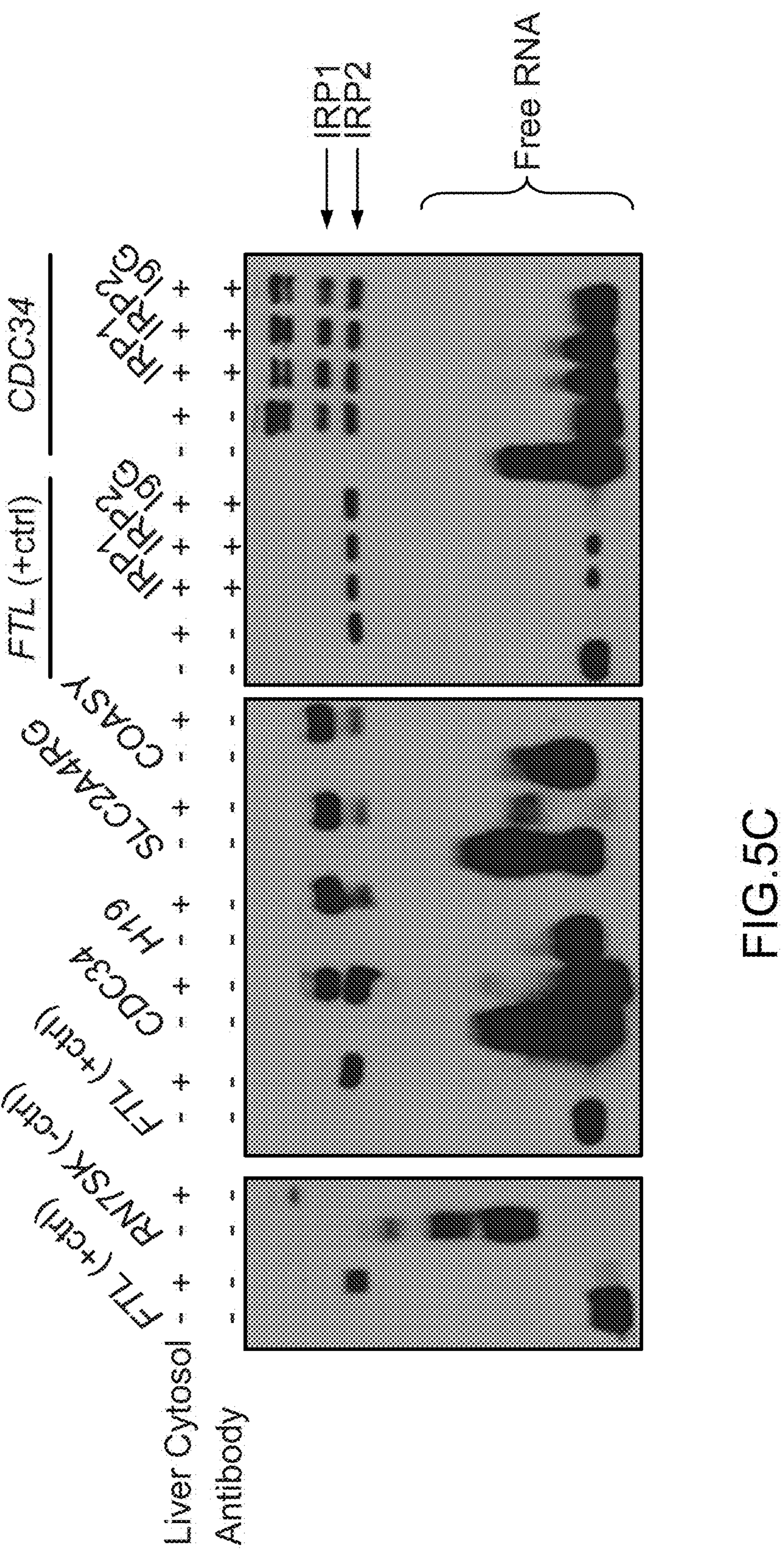

FIG. 5C shows results from electromobility shift assays testing predicted IREs for binding to IRP1 1/2. Biotin-labeled RNA is shown alone, incubated with liver cytosolic extract, or with antibodies to IRP1, IRP2, or Immunoglobulin G (IgG; negative control). FTL IRE, which tightly binds IRP proteins, is shown as a positive control; h3 stem loop of RN7SK shown as a negative control. Shifted bands in the presence of liver cytosol indicate RNA binding to protein. The release of RNA in the presence of antibodies indicates disruption of RNA-protein binding.

Figures 6A, 6C, 6D:
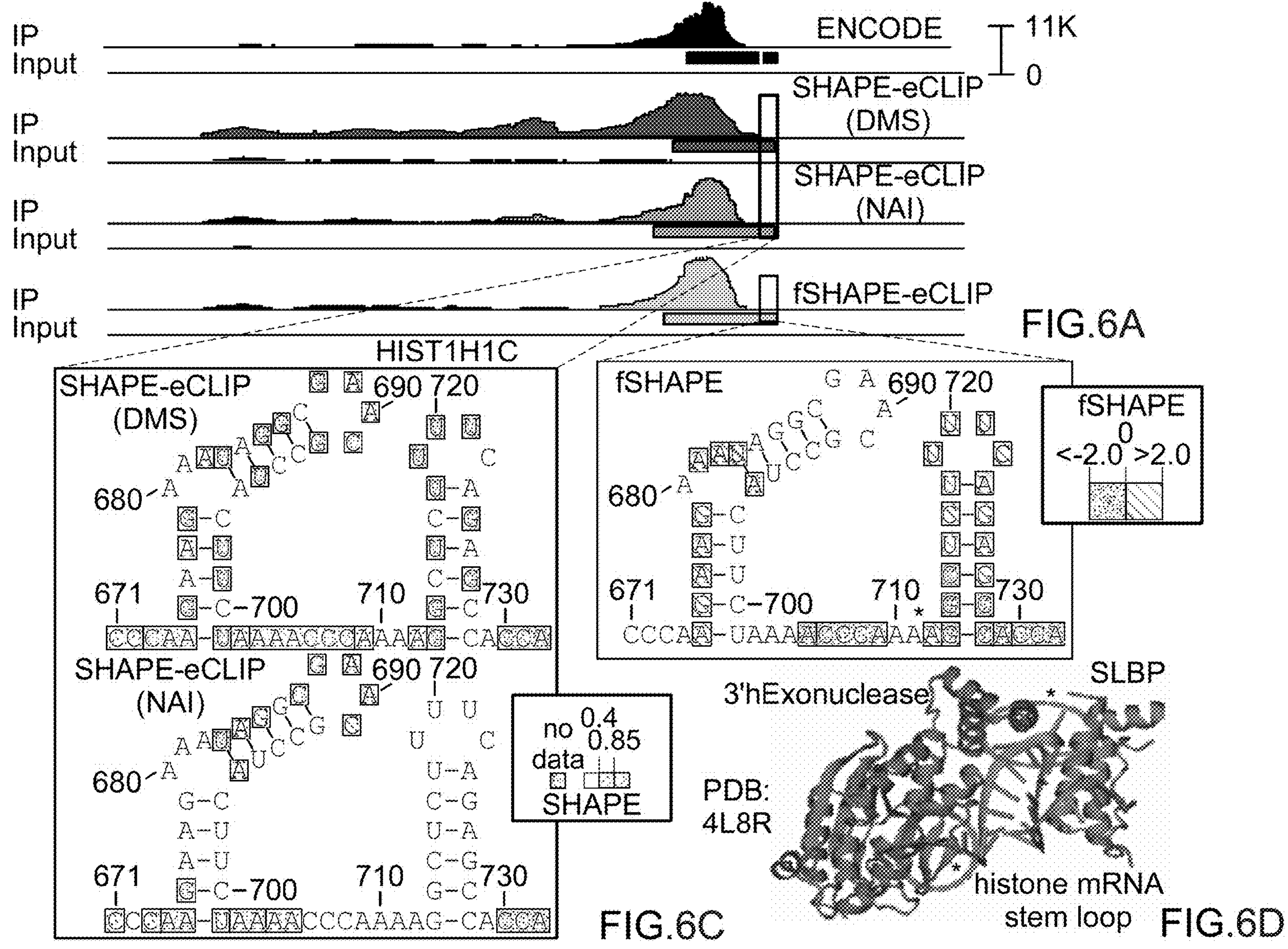

FIG. 6A shows read densities mapped to histone mRNA HIST1H1C for published eCLIP datasets (ENCODE). SHAPE-eCLIP under two probing reagent conditions (DMS and NAI), and fSHAPE-eCLIP. Each eCLIP dataset includes an immunoprecipitated sample (IP) and a non-immunoprecipitated negative control (Input). Binding sites inferred in each dataset are indicated as rectangles under read densities.

FIG. 6B shows percent of binding sites inferred in each eCLIP dataset that occur in histone transcripts and compared to previously published (ENCODE) SLBP binding sites. The percent overlap with ENCODE of an equivalent number of randomized binding sites is also shown for each dataset as a negative control.

FIG. 6C shows the predicted structure and overlaid SHAPE reactivities from two SHAPE-eCLIP datasets for the stem loop motif of HIST1H1C. Nucleotides numbered by position in transcript.

FIG. 6D shows the predicted structure and overlaid fSHAPE reactivities from fSHAPE-eCLIP dataset for the stem loop motif of HIST1H1C. Nucleotides numbered by position in transcript. Higher reactivities indicate bases that hydrogen bond with protein. The crystal structure of SLBP and 3'hExonuclease with canonical stem loop motif (PDBID: 4L8R). Bases known to hydrogen bond with either SLBP or 3'hExonuclease are circled. FIG. 6E shows average crosslinking rates (percent*10 for scale) in published SLBP eCLIP datasets in multiple histone transcripts aligned by stem loop motif (Upper panel); and fSHAPE reactivity profiles from fSHAPE-eCLIP in multiple histone transcripts aligned by stem loop motif (Lower panel). Average of profiles shown as dashed line. Stars indicate bases that are known to hydrogen bond with protein.

Figure 7:
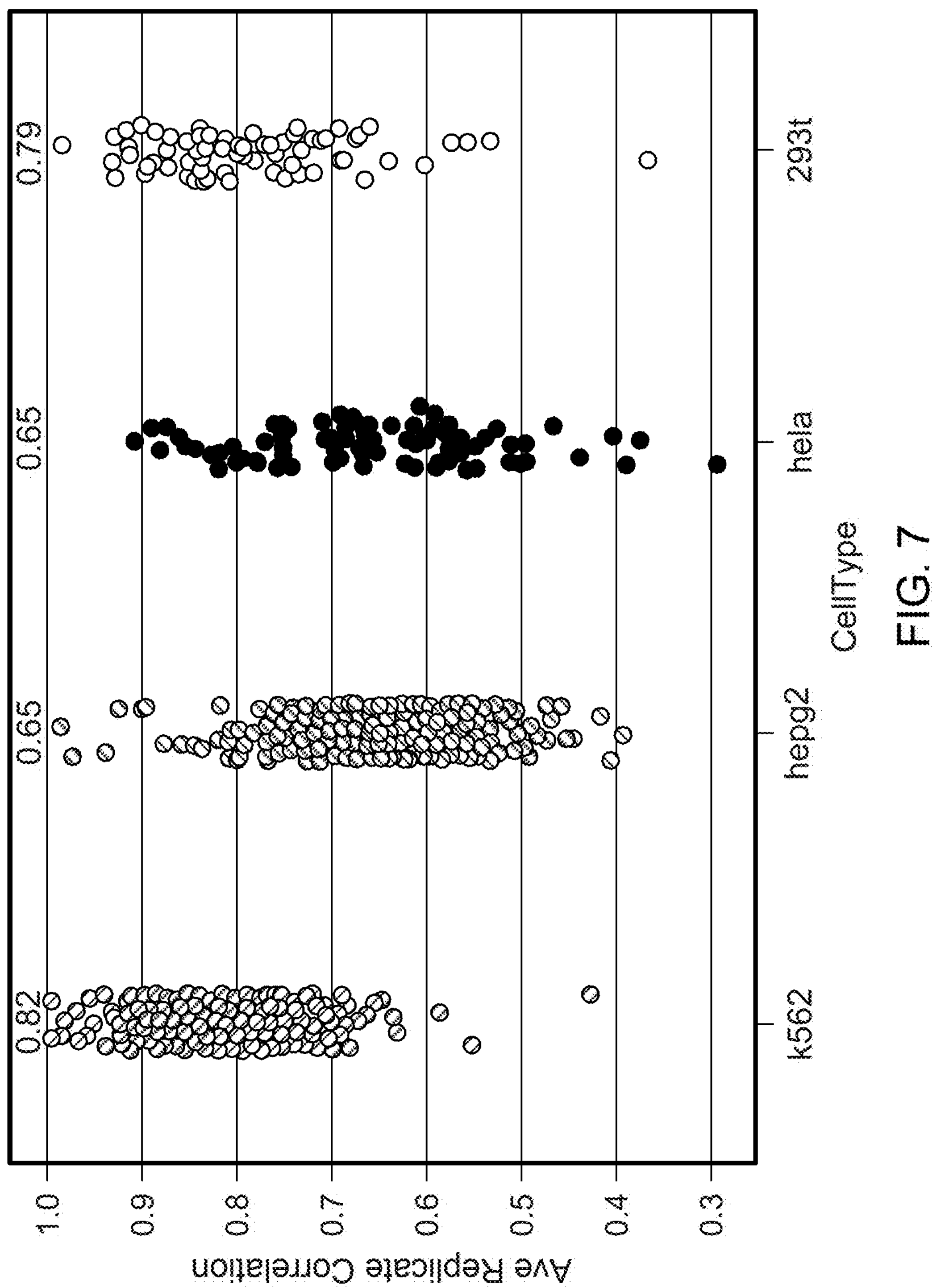

FIG. 7 shows average fSHAPE replicate Pearson correlations across transcripts in four cell lines. Overall averages indicated above each cell line.

Figure 8:
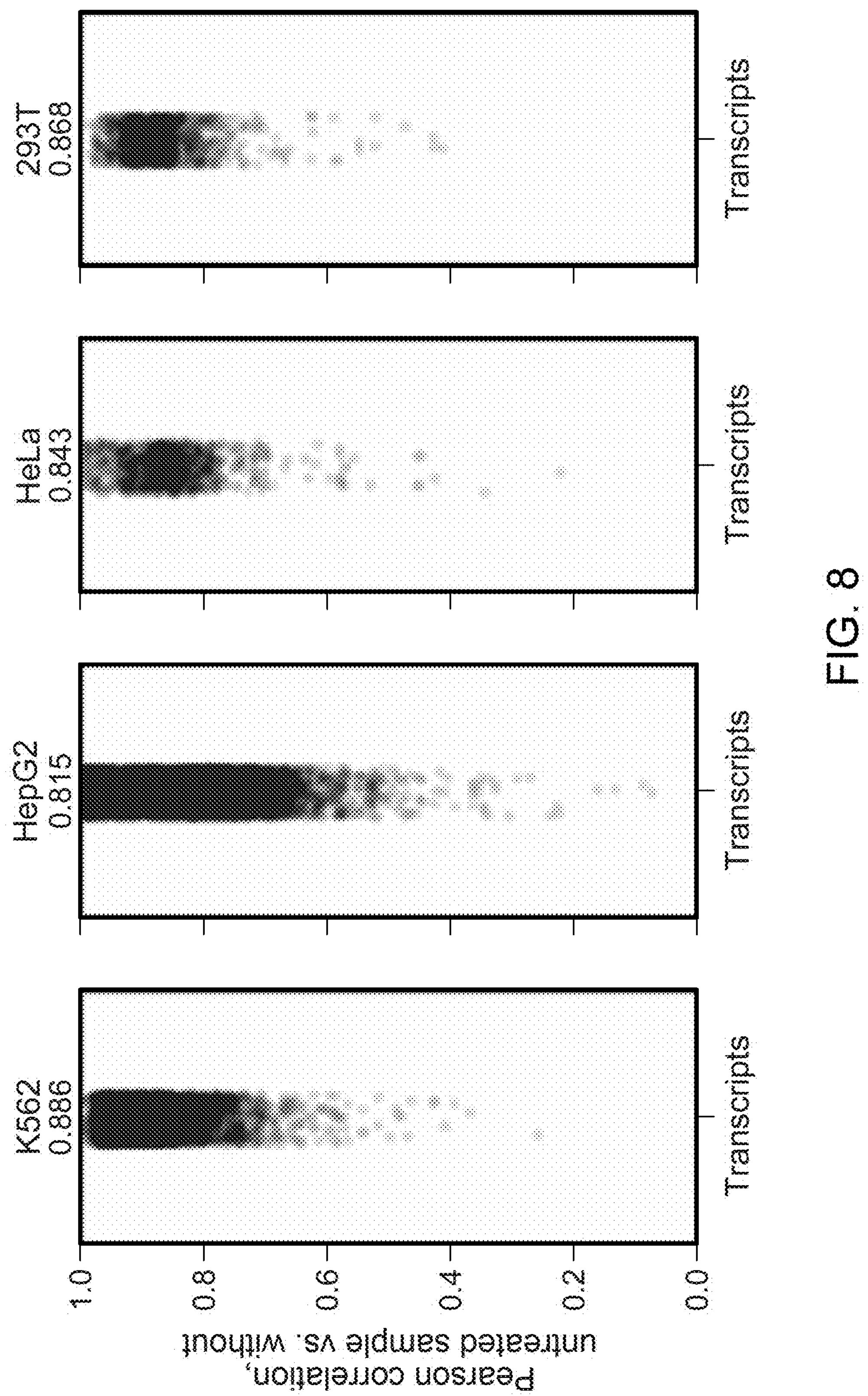

FIG. 8 shows average Pearson correlations across transcripts comparing fSHAPE reactivities calculated normalizing both −protein and +protein samples to an untreated sample versus fSHAPE reactivities calculated by simply normalizing the −protein sample to the +protein sample. Overall average correlation indicated at the top of each plot for data from each cell line.

Figure 9:
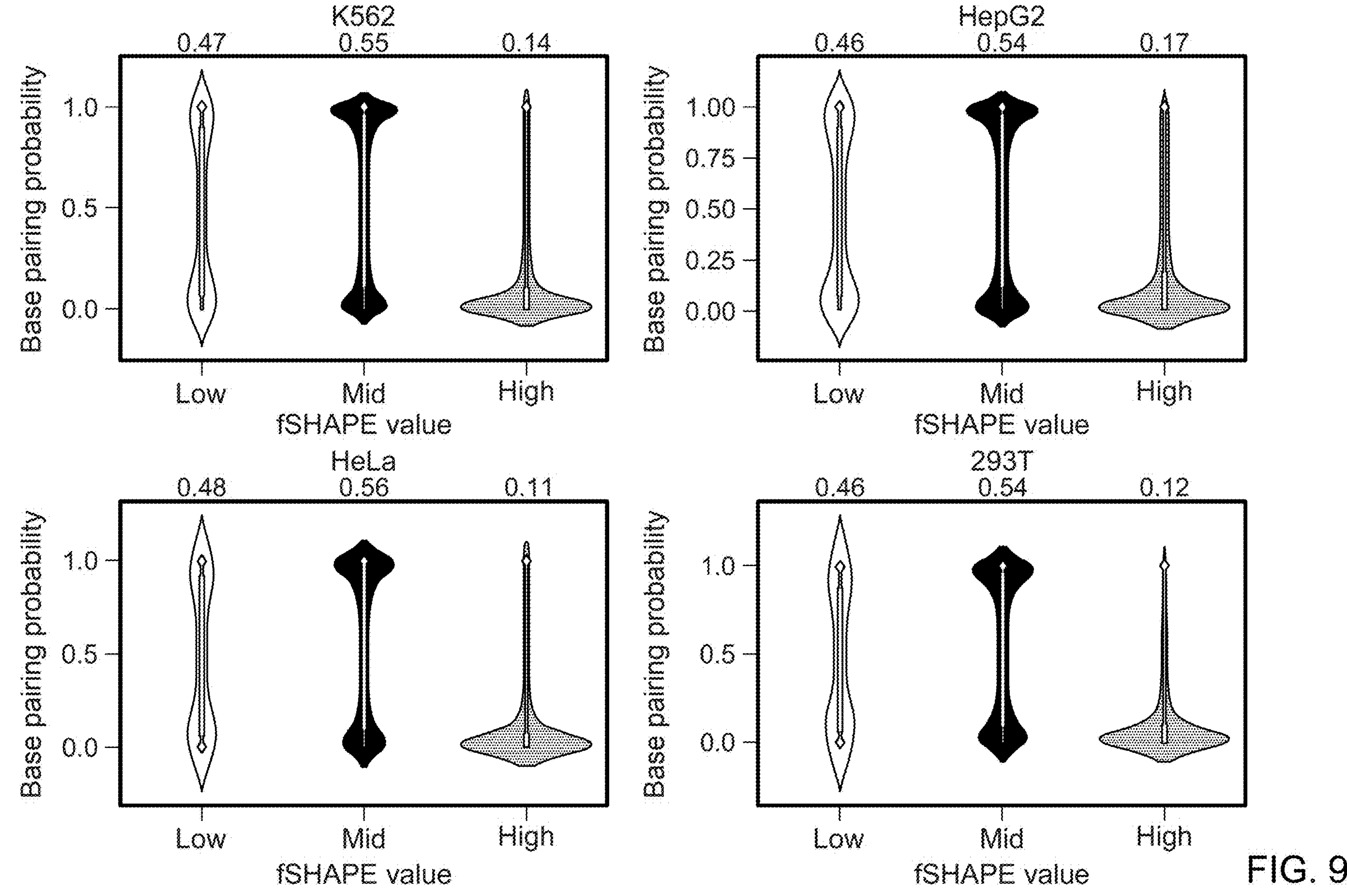

FIG. 9 shows predicted base pairing probability densities for nucleotides grouped by low, medium, and high fSHAPE reactivities in four cell lines. Average base pairing probability indicated above each group.

Figure 10:
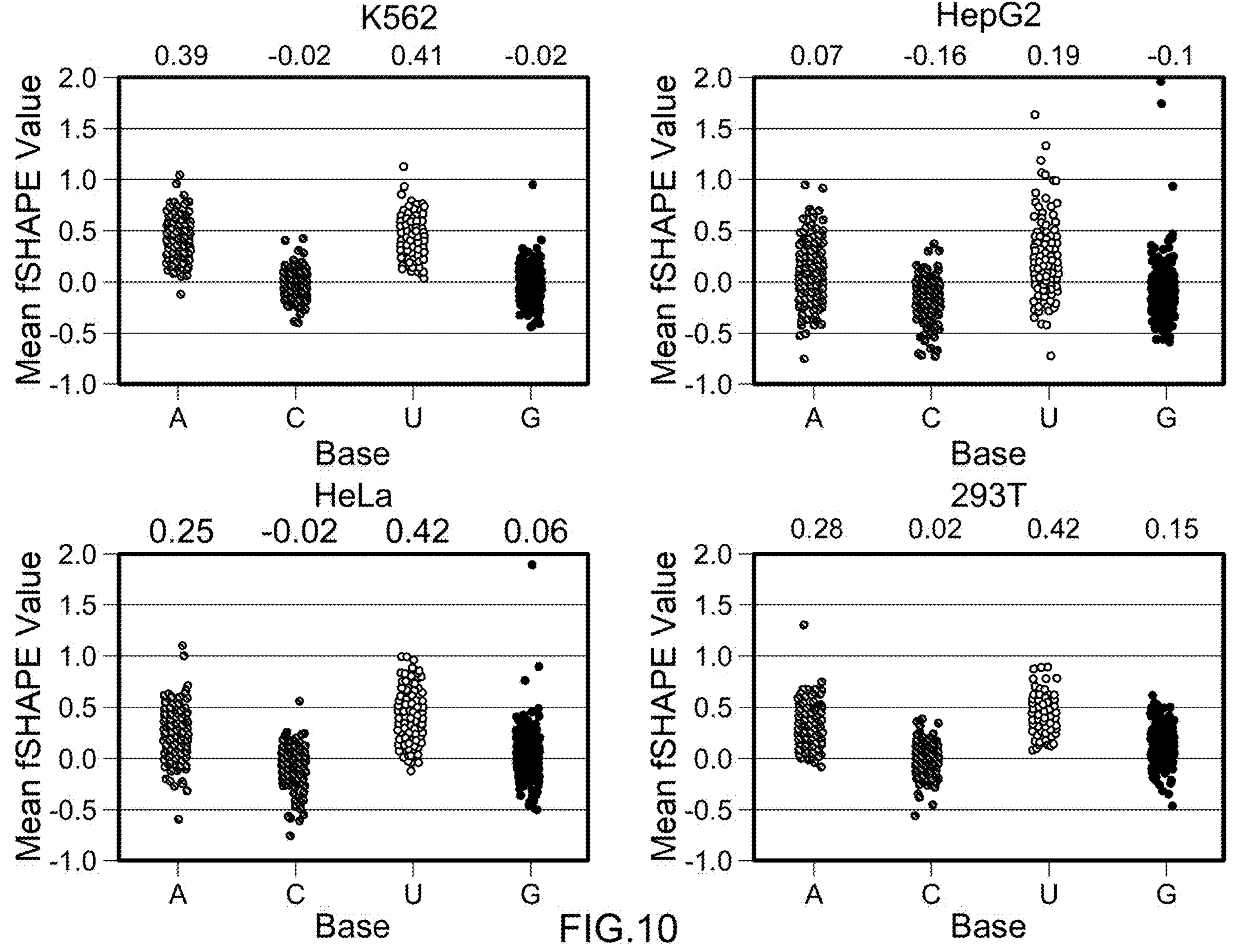

FIG. 10 show average nucleotide fSHAPE reactivities across transcripts for each cell line. Average indicated above each nucleotide.

Figure 11:
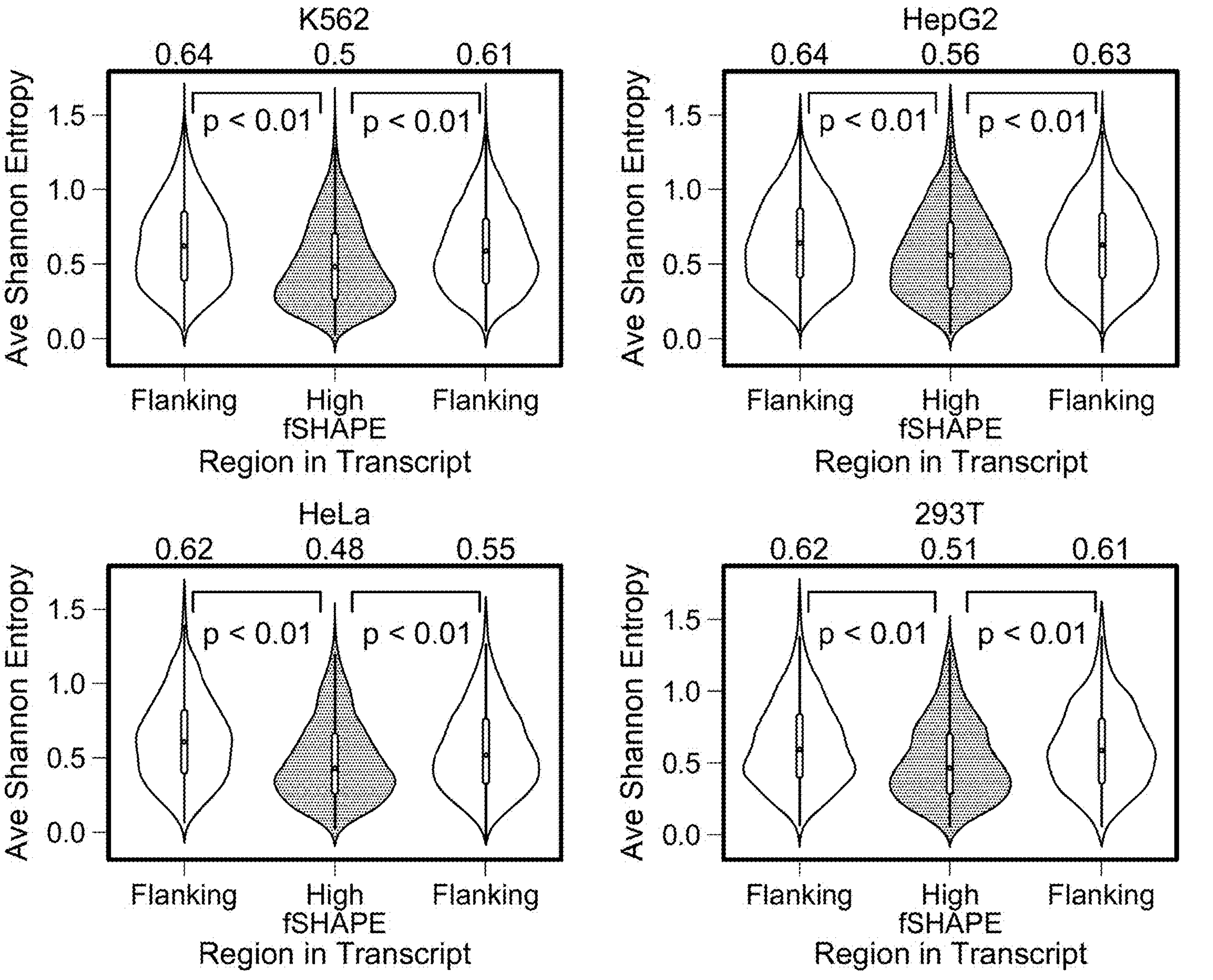

FIG. 11 shows Shannon entropy values predicted for 50-nucleotide regions containing high fSHAPE reactivities compared to 50-nucleotide flanking regions, for four cell lines. Average Shannon entropy indicated above each type of region.

Figure 12A:
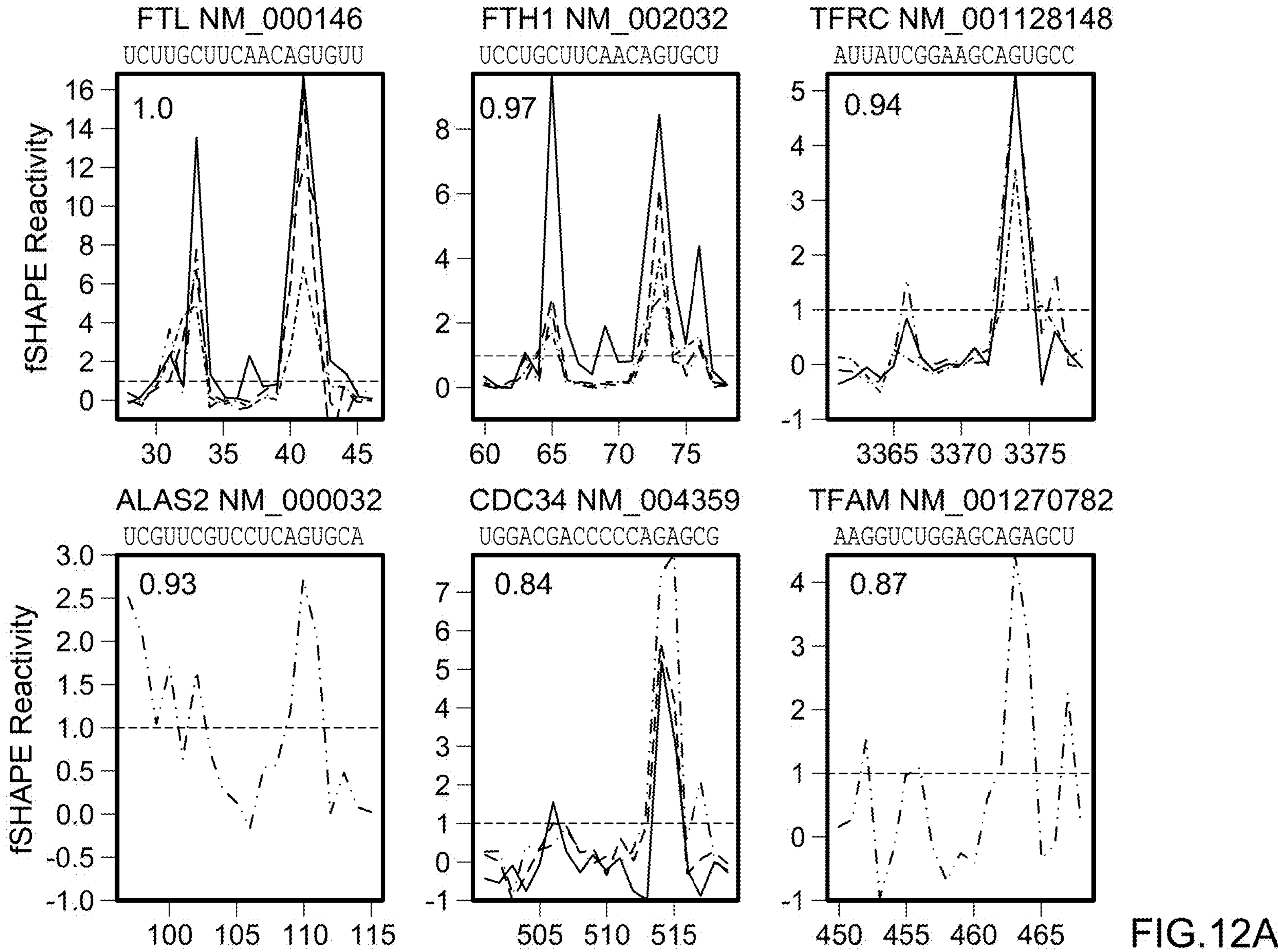
Figure 12A:
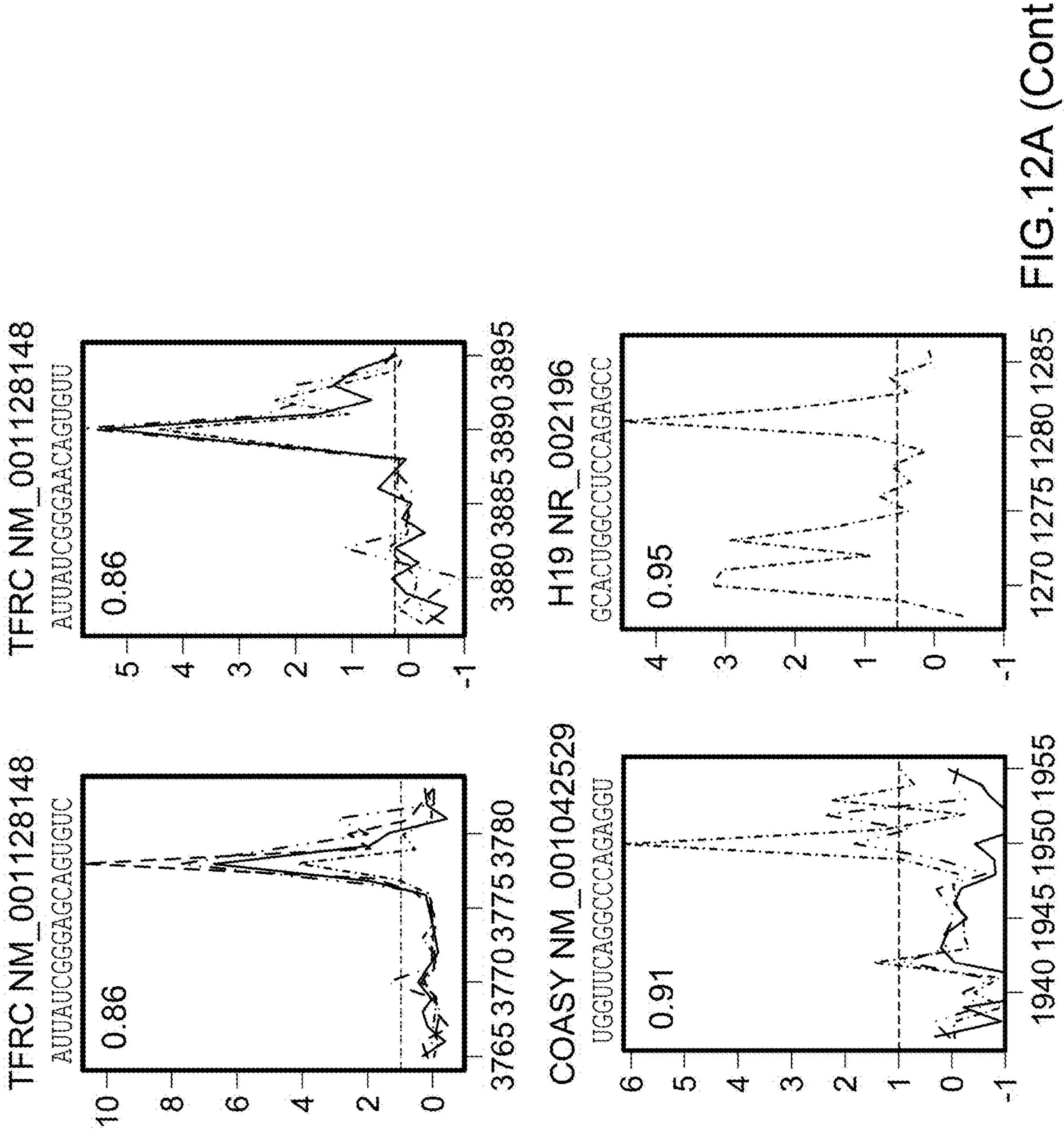

FIG. 12A shows fSHAPE reactivity profiles in multiple cell lines of predicted iron response elements (IREs) in transcripts. Pearson correlation compared to FTL is indicated in top left corner; best value shown, if fSHAPE data available in multiple cell lines. Gene name, transcript ID (NCBI), and sequence indicated above each plot. IREs in (FTL), FTH1, TFRC (multiple), and ALAS2 (top row) have been previously verified, the remainder are novel.

Figure 12B:
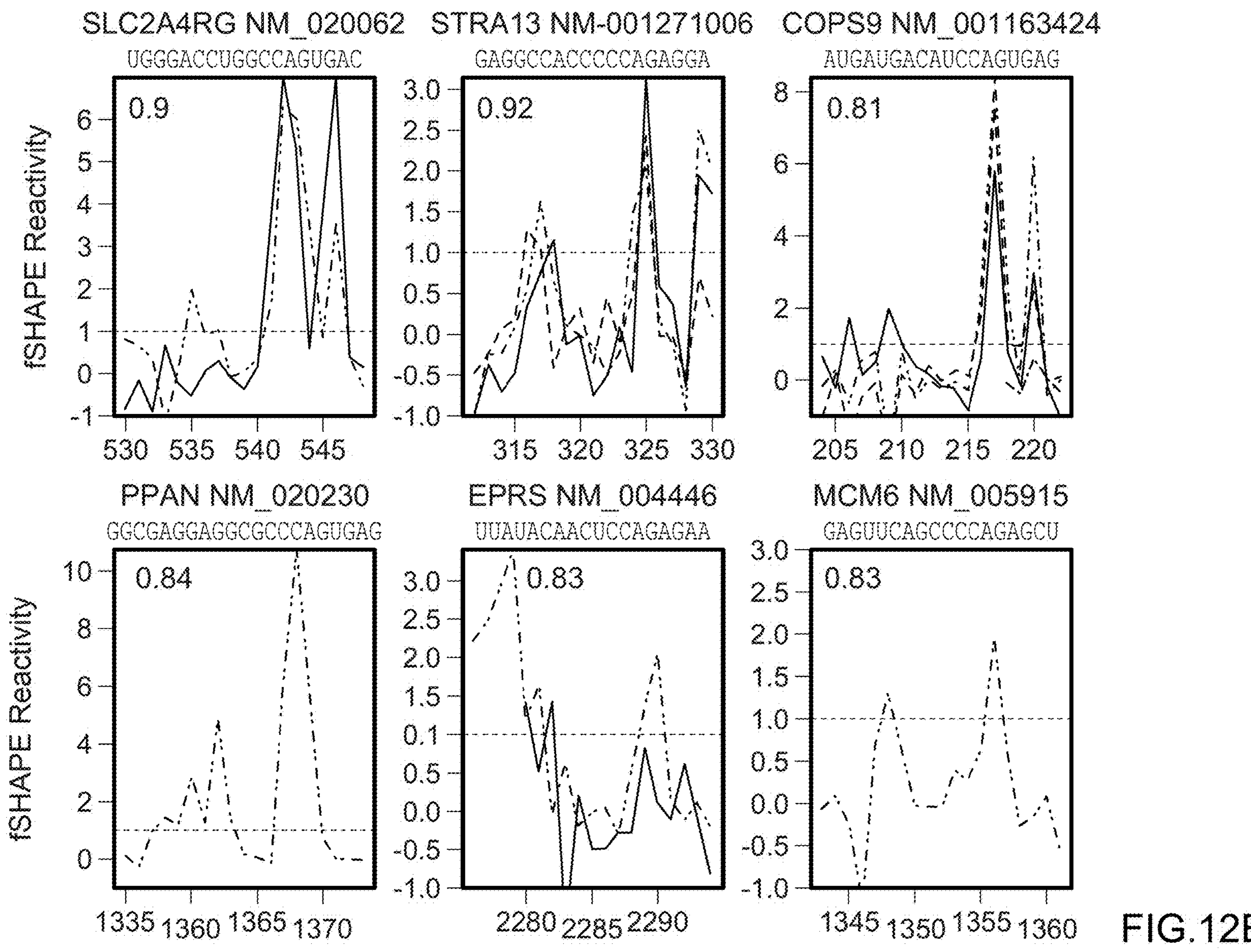
Figure 12B:
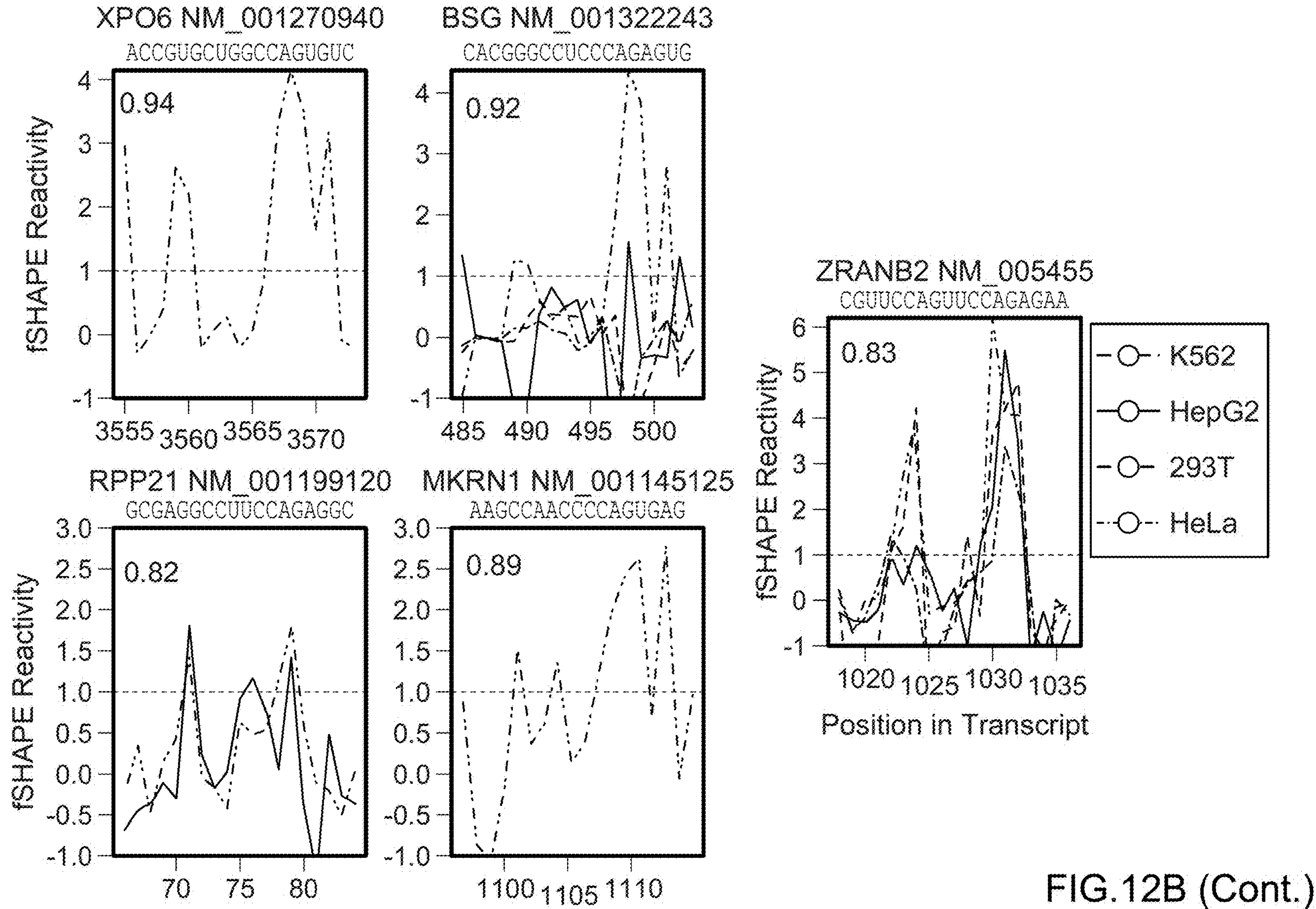

FIG. 12B shows fSHAPE reactivity profiles in multiple cell lines of predicted iron response elements (IREs) in transcripts. Gene name, transcript ID (NCBI), and sequence indicated above each plot. IREs in (FTL), FTH1, TFRC (multiple), and ALAS2 have been previously verified, the remainder are novel.

Figure 12C:
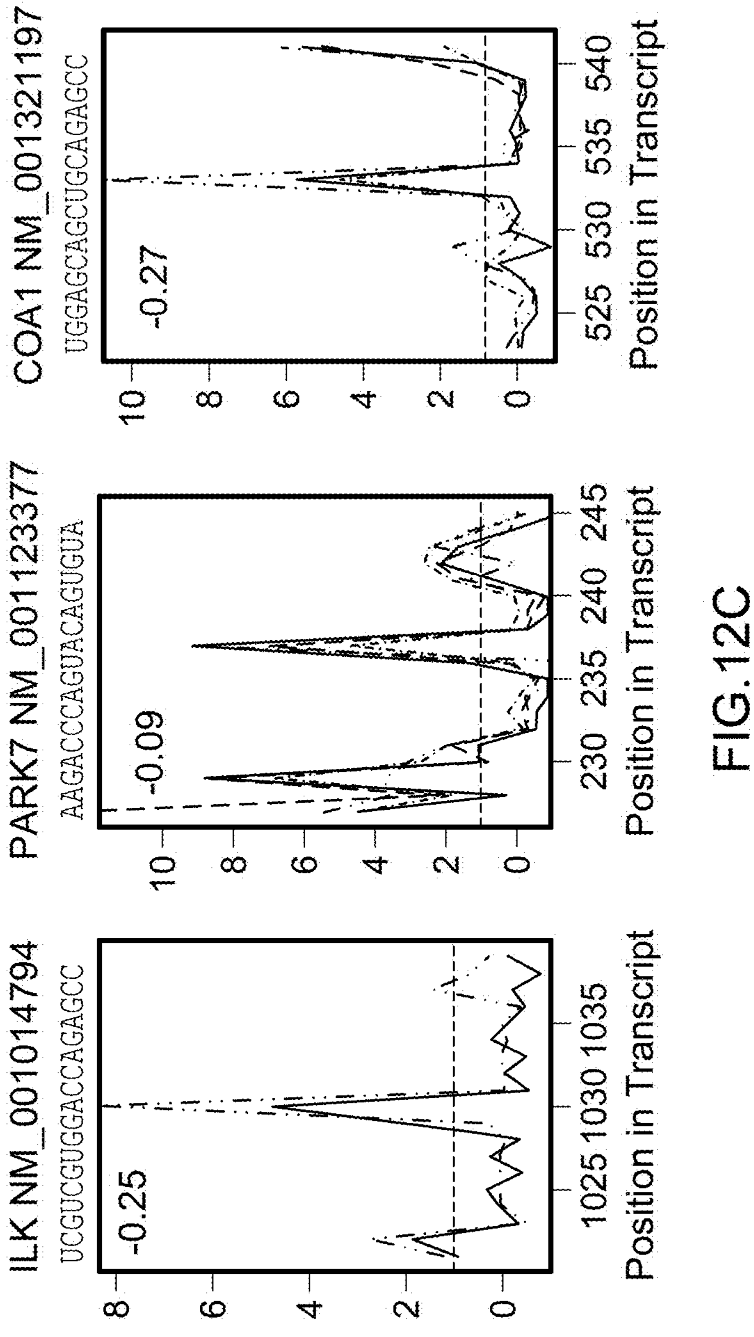

FIG. 12C shows example negative IRE matches. fSHAPE reactivity profiles of sequence matches to the iron response element whose fSHAPE reactivities do not match the FTL IRE.

Figure 13:
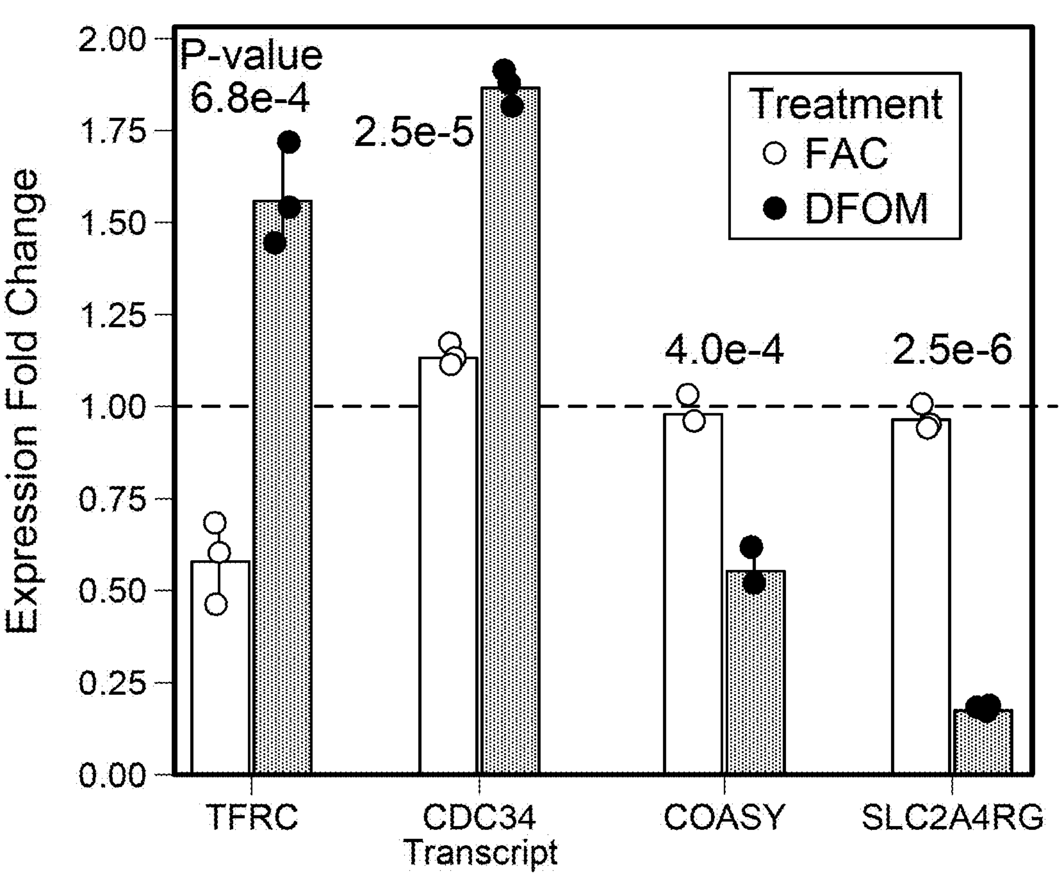

FIG. 13 shows quantitative PCR results for candidate IRE-containing transcripts in response to high iron (FAC) and low iron (DFOM) conditions. TFRC is the positive control and is expected to increase in response to lower cellular iron levels. Expression fold change is relative to transcripts' expression in untreated samples.

Figure 14A:
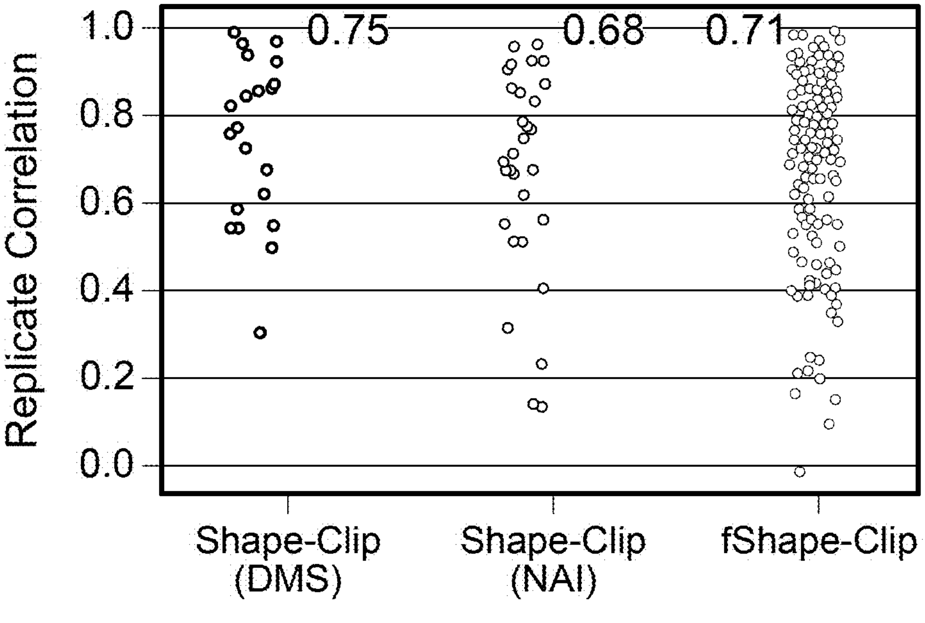

FIG. 14A shows the average Pearson correlations between transcripts in replicate SHAPE-CLIP (DMS or NAI) or fSHAPE-CLIP experiments. Overall averages indicated above each group.

Figure 14B:
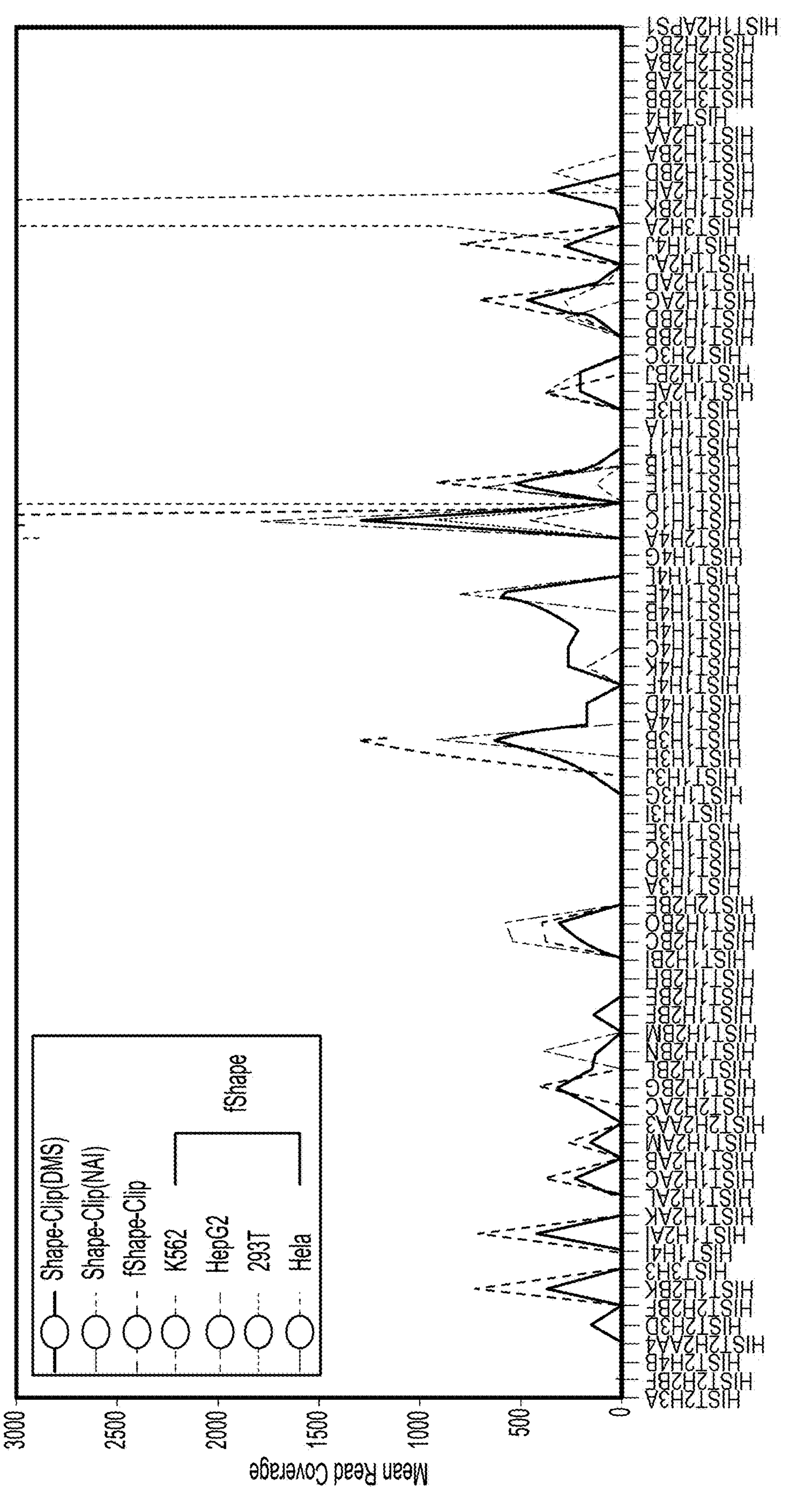

FIG. 14B shows mean read coverage at the 3' ends of histone transcripts in all fSHAPE datasets (K562 predominates) compared to SHAPE-CLIP and fSHAPE-CLIP experiments.

Figure 14C:
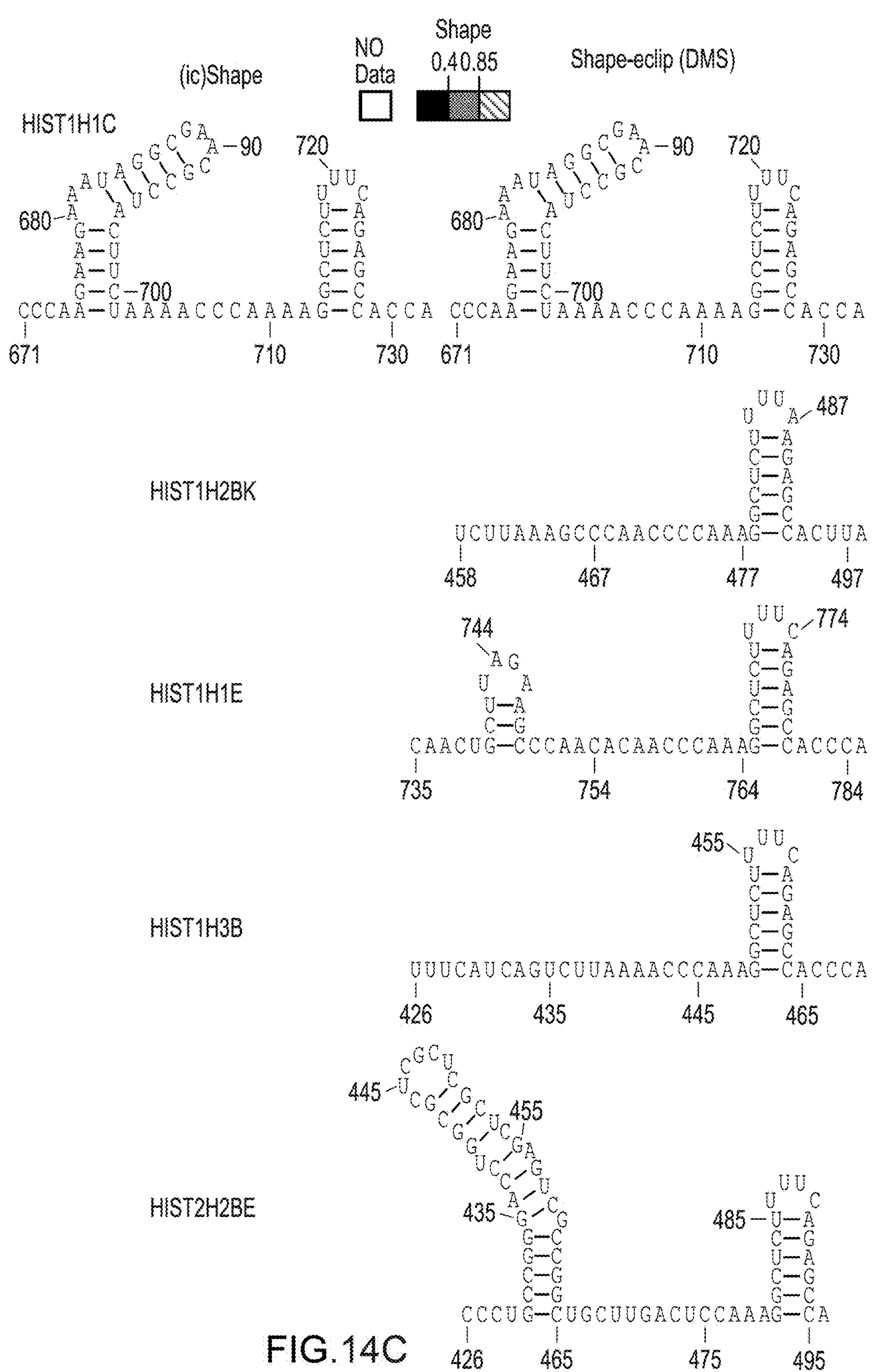
Figure 14C:
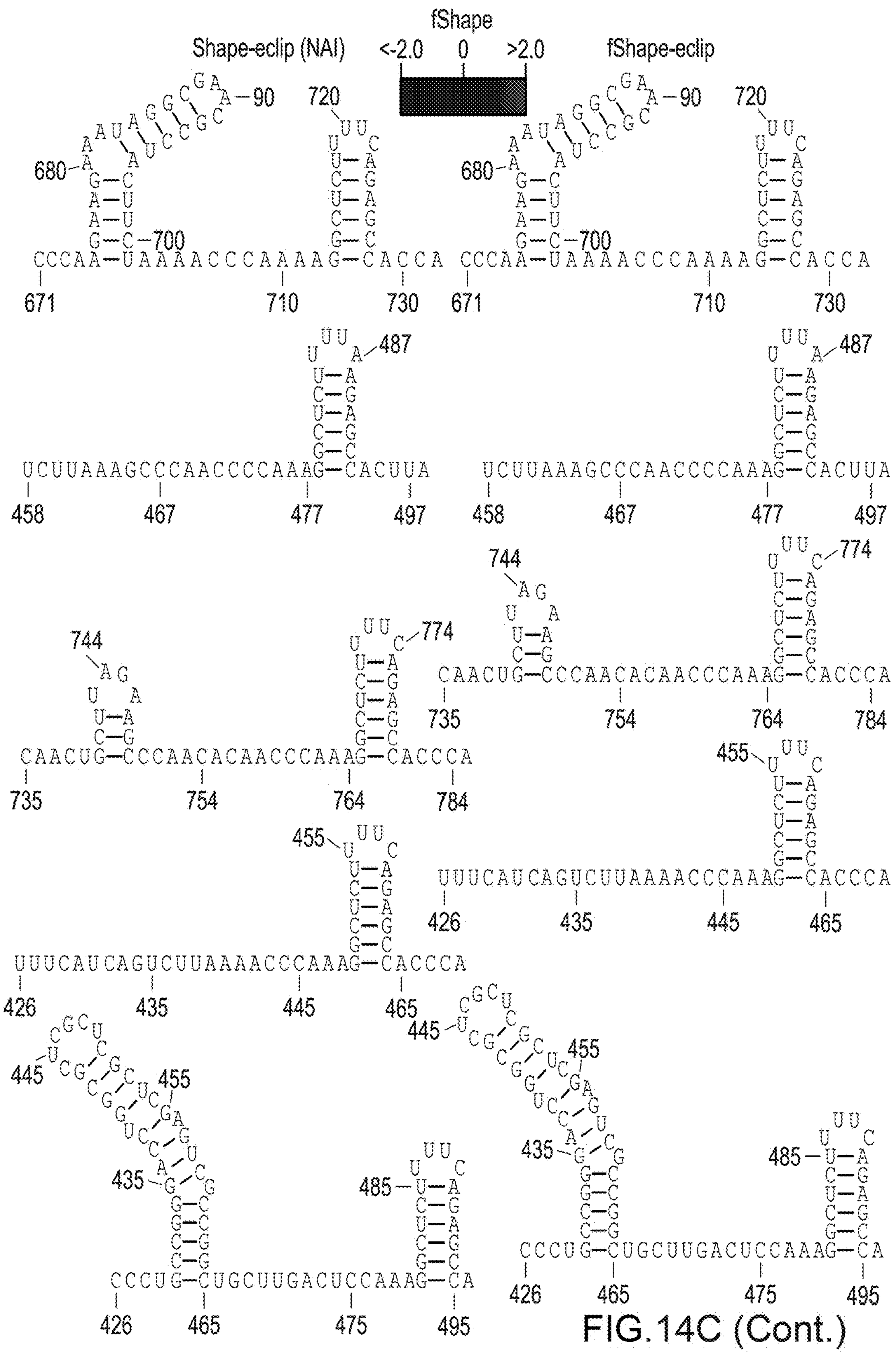

FIG. 14C shows predicted stem loop structures in histone transcripts overlaid with their SHAPE-eCLIP (DMS or NAI datasets) or fSHAPE-eCLIP reactivities, or icSHAPE reactivities where available. Bases are numbered by relative position in each transcript.

Figures 15A, 15B:
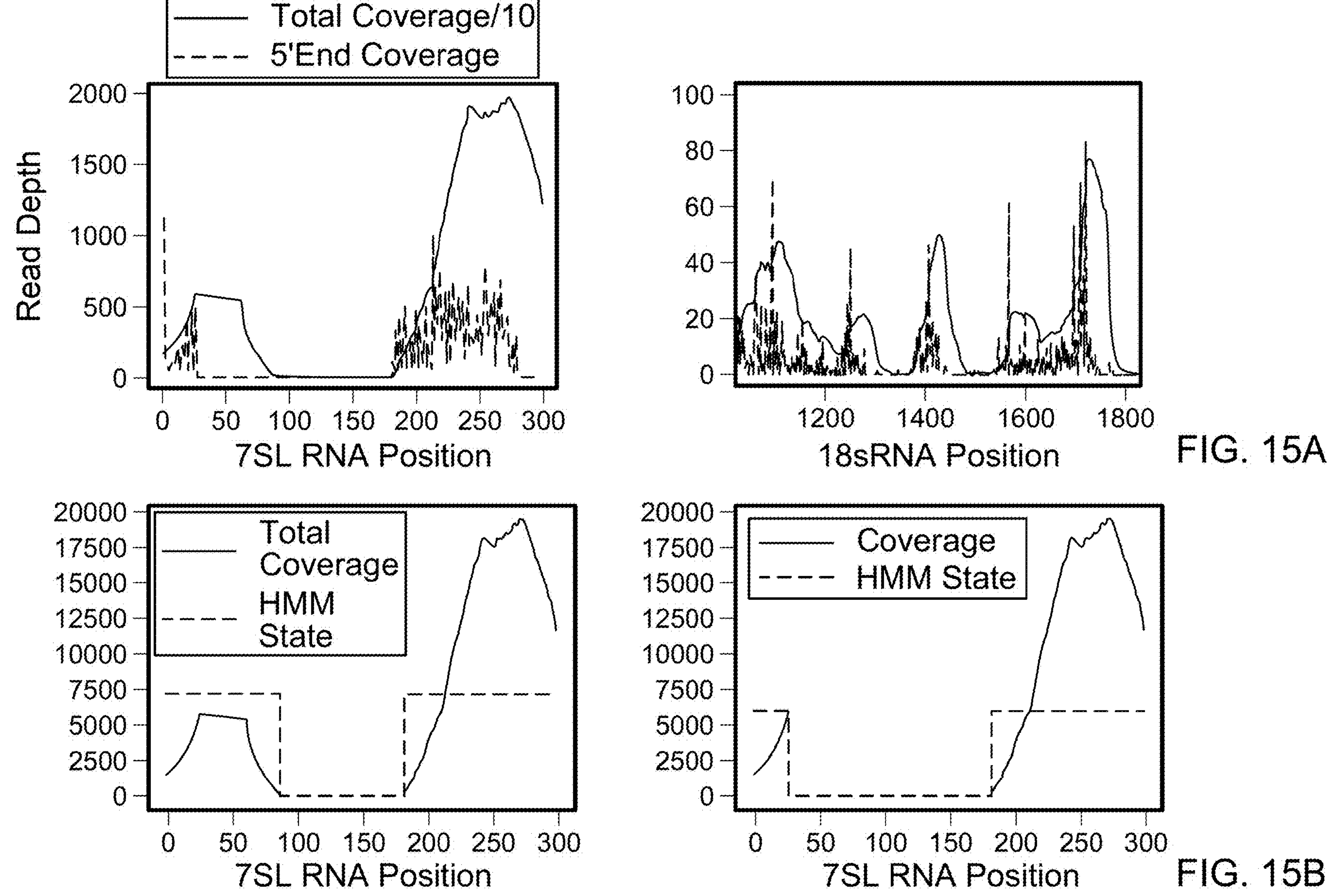

FIG. 15A shows that read coverage is often uneven across transcripts, where coverages occasionally drop to zero or negligible reads. RTstop based SHAPE methods rely on total coverage counts compared to the 5' end coverage counts to calculate RT-stop frequencies (5'end counts/total counts) at each nucleotide. In regions where total coverage drops to negligible densities, the 5'end coverage will always drop to zero counts before the drop in total coverage. These zero-valued 5'end coverage counts will be calculated as RT-stop frequencies of zero (0/total counts=0), when in fact they should be calculated as "no data."

FIG. 15B shows a two-state HMM was used to define regions of "gapped" total coverage" in the sequencing data, which were then extended to include the upstream positions where the 5'end coverage gap begins, and these regions were set to "no data" RT-stop frequencies.

Figure 16:
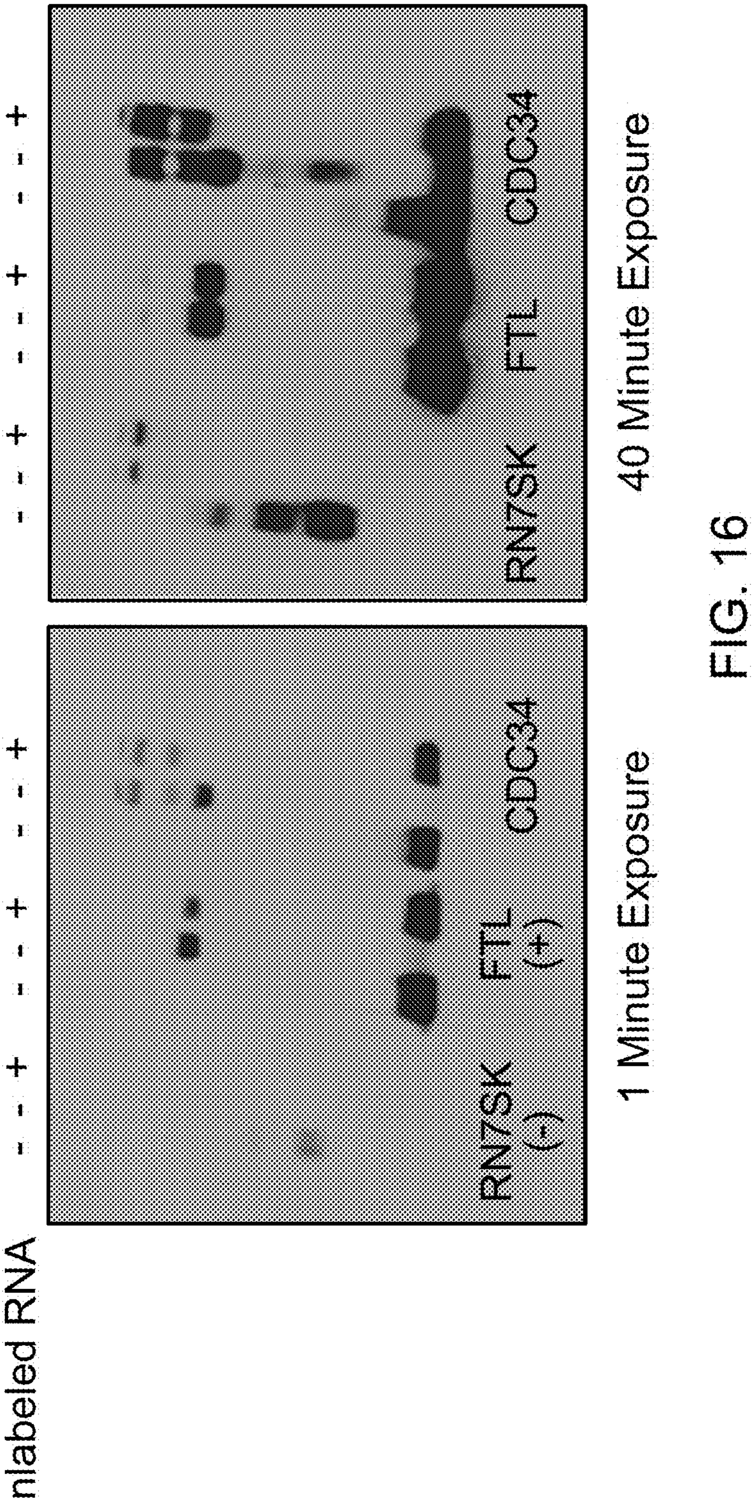

FIG. 16 shows full uncropped gel images for FIG. 5C.

Figure 17:
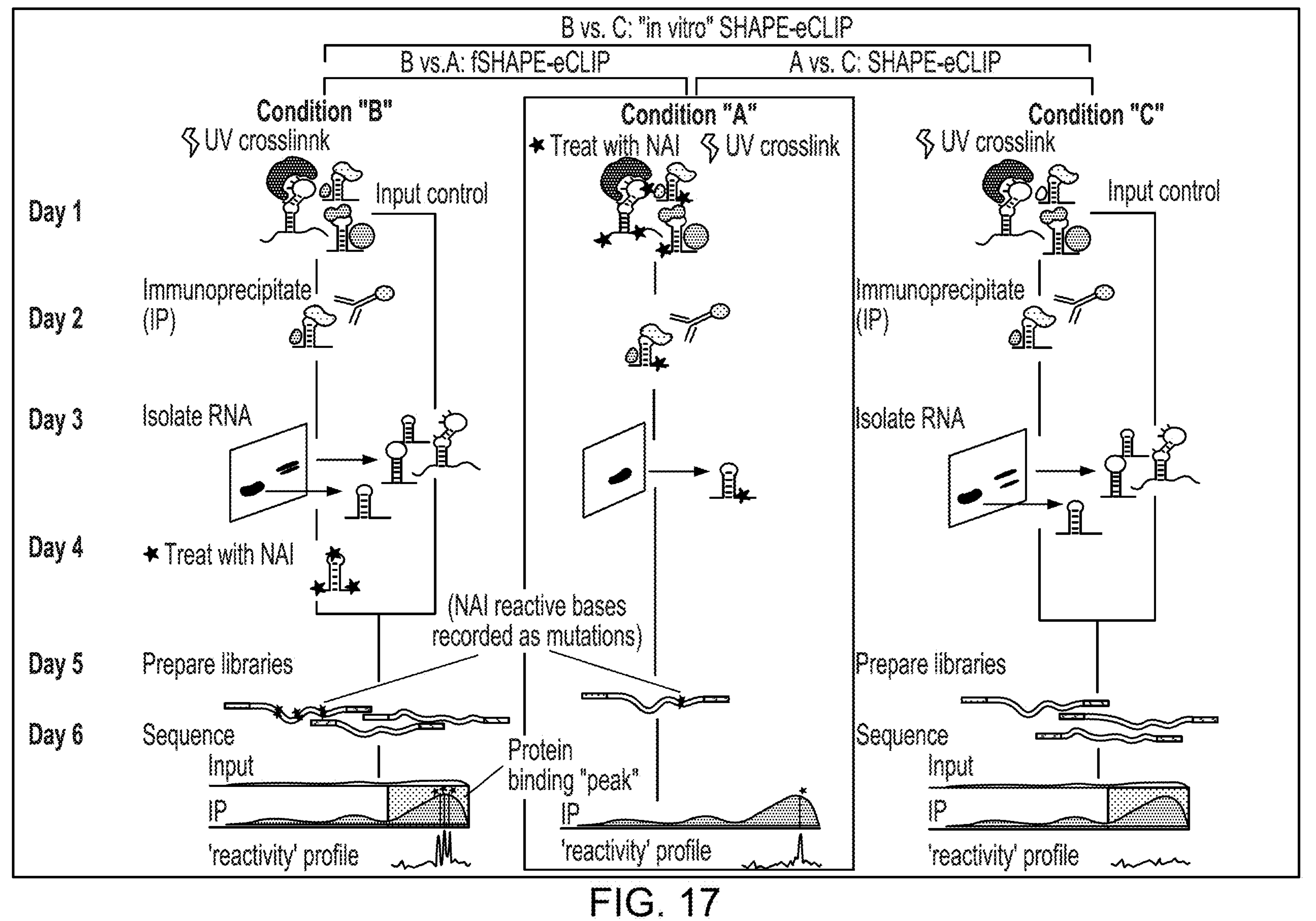

FIG. 17 shows exemplary schematics of workflows wherein selective 2'-hydroxyl acylation analyzed by primer extension (SHAPE) structure probing techniques characterize the secondary structure of RNA molecules, which influence their functions and interactions. A variation of SHAPE, footprinting SHAPE (fSHAPE), probes RNA in the presence and absence of protein to identify RNA bases that hydrogen-bond with protein. SHAPE or fSHAPE coupled with enhanced crosslinking and immunoprecipitation (SHAPE-eCLIP or (SHAPE-eCLIP) pulls down RNAs bound by any protein of interest and returns their structure or protein interaction information, respectively.

DETAILED DESCRIPTION

Detailed herein are methods for identifying a RNA nucleobase that interacts with an RNA binding protein (RBP). For example, a method can include (a) crosslinking the RNA binding protein to an RNA fragment in a biological sample; (b) detecting an RNA-RBP complex, wherein the RNA-RBP complex includes the RNA fragment bound by the RNA binding protein; (c) isolating the RNA fragment of the RNA-RBP complex; and (d) profiling the isolated RNA fragment bound by the RNA binding protein, thereby identifying the RNA nucleobase of the RNA fragment that interacts with the RNA binding protein. In some embodiments, a nucleobase interacts with an RNA binding protein via hydrogen bond within a cell.

Various non-limiting aspects of these methods are described herein, and can be used in any combination without limitation. Additional aspects of various components of methods for identifying an RNA nucleobase that interacts with an RBP, or methods of identifying hydrogen bond interactions between an RNA molecule and an RBP are known in the art.

It must be noted that, as used in the specification and the appended claims, the singular forms "a," "an" and "the" include plural referents unless the context clearly dictates otherwise.

As used herein, "biological sample" can refer to a sample generally including cells and/or other biological material. A biological sample can be obtained from non-mammalian organisms (e.g., a plants, an insect, an arachnid, a nematode), a fungi, an amphibian, or a fish (e.g., zebrafish). A biological sample can be obtained from a prokaryote such as a bacterium, e.g., *Escherichia coli, Staphylococci* or *Mycoplasma pneumoniae*; an archaea; a virus such as Hepatitis C virus or human immunodeficiency virus; or a viroid. A biological sample can be obtained from a eukaryote, for example a mammal such as such as a human or other primate, pig, hamster, mouse, rat, cow, horse, cat, dog, sheep, or goat. In some embodiments, a biological sample can be a cancer cell derived from any of the biological material described herein. In a non-limiting example, biological sample can be a patient derived organoid (PDO) or patient derived xenograft (PDX). Biological samples can be derived from a homogeneous culture or population of organisms or alternatively from a collection of several different organisms, for example, in a community or ecosystem.

The biological sample can include any number of macromolecules, for example, cellular macromolecules and organelles (e.g., mitochondria and nuclei). The biological sample can be a nucleic acid sample and/or protein sample. The biological sample can be a carbohydrate sample or a lipid sample. The biological sample can be obtained as a tissue sample, such as a tissue section, biopsy, a core biopsy, needle aspirate, or fine needle aspirate. The sample can be a fluid sample, such as a blood sample, urine sample, or saliva sample. The sample can be a skin sample, a colon sample, a cheek swab, a histology sample, a histopathology sample, a plasma or serum sample, a tumor sample, living cells, cultured cells, a clinical sample such as, for example, whole blood or blood-derived products, blood cells, or cultured tissues or cells, including cell suspensions.

In some embodiments, the biological sample comprises a tissue, a tissue section, an organ, an organism, an organoid, or a cell culture sample. In some embodiments, the biological sample comprises live cells from a cell culture. In some embodiments, the biological sample comprises a frozen tissue sample.

As used herein, "detecting" can refer to a method used to discover, determine, or confirm the existence or presence of a compound and/or substance (e.g., DNA, RNA, a protein). In some embodiments, a detecting method can be used to detect a protein. In some embodiments, a detecting method can be used to detect an RNA binding protein bound to an RNA fragment. In some embodiments, detecting can include chemiluminescence or fluorescence techniques. In some embodiments, detecting can include immunological-based methods (e.g., quantitative enzyme-linked immunosorbent assays (ELISA), Western blotting, or dot blotting) wherein antibodies are used to react specifically with entire proteins or specific epitopes of a protein. In some embodiments, detecting can include immunoprecipitation of the protein.

As used herein, the term "hydrogen bond" or "hydrogen bonding" can refer to an electrostatic force of attraction between a hydrogen (H) atom and the hydrogen bond acceptor (Ac). In some embodiments, a protein can interact with an RNA molecule via hydrogen bonds. In some embodiments, an amino acid of a protein can form a hydrogen bond with a nucleotide of an RNA molecule. In some embodiments, a protein and an RNA molecule can form a protein-RNA complex via a hydrogen bond, wherein the protein-RNA complex includes a single hydrogen bond. In some embodiments, the protein-RNA complex can include two or more hydrogen bonds.

As used herein, "immunoprecipitation" is the technique of precipitating a protein antigen out of solution using an antibody that specifically bind to that particular protein. In some embodiments, the solution containing the protein antigen is in the form of a crude lysate of an animal tissue. Immunoprecipitation can be used to isolate and concentrate a particular protein from a sample containing many different proteins. Also, this technique requires that the antibody be coupled to a solid substrate (e.g., immunoprecipitation beads) while preforming the procedure.

As used herein, "isolating" can refer to a method in which a biomolecule (e.g., a protein, a protein-RNA complex) is separated from a complex sample mixture (e.g., a cell culture, cell or tissue lysate). In some embodiments, a protein can be isolated by using differences in protein size, physico-chemical properties, binding affinity, and biological activity. In some embodiments, a protein can be isolated by using immunoprecipitation, wherein the specificity of antibodies to a target protein is used to isolate the target protein out of a sample mixture.

As used herein, "nucleic acid" is used to include any compound and/or substance that comprise a polymer of nucleotides. In some embodiments, a polymer of nucleotides are referred to as polynucleotides. Exemplary nucleic acids or polynucleotides can include, but are not limited to, ribonucleic acids (RNAs), deoxyribonucleic acids (DNAs), threose nucleic acids (TNAs), glycol nucleic acids (GNAs), peptide nucleic acids (PNAs), locked nucleic acids (LNAs, including LNA having a β-D-ribo configuration, α-LNA having an α-L-ribo configuration (a diastereomer of LNA), 2'-amino-LNA having a 2'-amino functionalization, and 2'-amino-α-LNA having a 2'-amino functionalization) or hybrids thereof. Naturally-occurring nucleic acids generally have a deoxyribose sugar (e.g., found in deoxyribonucleic acid (DNA)) or a ribose sugar (e.g., found in ribonucleic acid (RNA)). In some embodiments, a nucleic acid can be a fragment of a larger nucleic acid (e.g., an RNA fragment or DNA fragment).

A nucleic acid can contain nucleotides having any of a variety of analogs of these sugar moieties that are known in the art. A deoxyribonucleic acid (DNA) can have one or more bases selected from the group consisting of adenine (A), thymine (T), cytosine (C), or guanine (G), and a ribonucleic acid (RNA) can have one or more bases selected from the group consisting of uracil (U), adenine (A), cytosine (C), or guanine (G).

As used herein, "nucleoside" is used to include nucleotides without a phosphate group. A nucleoside comprises a nucleobase (e.g., nitrogenous base) and a five-carbon sugar ribose, and a nucleotide comprises a nucleobase, a five-carbon sugar, and one or more phosphate groups. For example, a nucleoside can be a cytidine, uridine, guanosine, thymidine, or inosine. A "nucleobase" can refer to a nitrogen-containing biological compound that forms the nucleosides, which, in turn, are components of nucleotides. Nucleobases have the ability to form base pairs and to stack one upon another, leading to long-chain helical structures such as ribonucleic acid (RNA) and deoxyribonucleic acid (DNA). There are five nucleobases, adenine (A), cytosine (C), guanine (G), thymine (T), and uracil (U), that function as the fundamental units of the genetic code, with the bases A, G, C, and T being found in DNA while A, G, C, and U are found in RNA.

As used herein, "profiling" can refer to a method used to understand the genetic information related to an individual subject or specific cell type and the way their genes interact with each other and with the environment. Profiling can include assessing genomic molecules (e.g., DNA molecules, RNA molecules) to detect or identify genomic alterations (e.g., mutations, base substitutions, insertions and deletions, copy number alterations, rearrangements, or fusions) within the genomic molecules. In some embodiments, profiling can include sequencing a genomic molecule (e.g., high-throughput sequencing, next-generation sequencing (NGS)) wherein the mutational profile includes information of interaction sites on the genomic molecule that interact with specific proteins.

As used herein, a "protease" can refer to an enzyme capable of degrading a protein or a peptide. In some embodiments, a biological sample can be treated with a protease to degrade or break down proteins in the biological sample. In some embodiments, a protease can break down a protein of a protein-RNA complex, wherein the protein is bound to an RNA molecule, thereby removing the protein from the RNA molecule. In some embodiments, a protease can include a serine protease, an aspartyl protease, pepsin, proteinase K, or a lysosomal protease.

RNA Binding Protein (RBP)

As used herein, "RNA binding protein" can refer to a protein that interacts with the double or single stranded RNA in cells and participate in forming ribonucleoprotein complexes. RNA binding proteins (RBPs) play a major role in post-transcriptional control of RNAs (e.g., splicing, polyadenylation, mRNA stabilization, mRNA localization, and translation). The term "RNA binding protein" can refer to a protein that interacts with RNA molecules (e.g., mRNA) from synthesis to decay to affect their metabolism, localization, stability, and translation.

In some embodiments, an RBP is a nuclear protein. In some embodiments, RBPs can include, but are not limited to, splicing factors, RNA stability factors, histone stem-loop binding proteins, or ribosomes. For example, a eukaryotic ribosome can include a collection of RBPs that can interact directly with mRNA coding sequences. In some embodiments, an RBP is a cytoplasmic protein. In some embodiments, an RNA binding protein comprises a ribosomal protein, wherein the ribosomal protein binds to a ribosome and an mRNA during translation. In some embodiments, an RNA binding protein comprises a ribosomal protein, wherein the ribosomal protein binds to a ribosome or an mRNA during translation. In some embodiments, the RNA binding protein comprises at least one of: SLTM, ZGPAT, PPARGC1B, PELP1, DCP2, CSTF3, TRA2B, ZNF638, SRSF9, LUC7L2, PTBP3, SF3B3, VCP, HNRNPA2B1, PTBP1, PCBP2, LSM14A, LSM12, DHX15, DDX27, DDX17, DDX21, IPO5, RPL22L1, RPL35, RPSA, MRPS34, NIFK, THUMPD1, RPUSD3, RRBP1, EEFSEC, UBAP2L, PUS7L, EIF4ENIF1, BICC1, EIF4E2, DARS2, TRDMT1, UPF3B, ZFP36L2, YTHDF2, EDC3, HNRNPR, UPF3A, ELAVL1, RBM27, XRN1, FUS, EXOSC7, PSPC1, CNOT7, CNOT6, CNOT4, CNOT3, AGO2, ENDOU, RBFOX1 (A2BP1), RBFOX2 (RBM9), RBFOX3 (NeuN), SLBP, RBM5, RBM6, PRBP1, ACO1, Adat1, PCBP1, PCBP3, PCBP4, RBM3, RBM4, APOBEC1, BTG1, CNOT2, CPSF5, DDX6, EWSR1, FUBP1, hnRNPA0, hnRNPC1/2, MEX3C, NANOS1, NANOS2, NOP56, PARN, PRR3, RBM14, RBM7, RPS6, SAMD4A, SNRPA, SRSF11, TOB1, TOB2, UTP11L, ZC3H18, ZCCHC11, ZFP36, ZFP36L1, ABT1, AC004381.6, AIMP1, ALDH18A1, ANXA2 , APOBEC3F, ASCC1, ATP5C1, BCCIP, BOLL, BYSL, BZW1, CELF5, CLK1, CLK2, CPSF1, DAZ2, DAZ3, DAZ4, DCN, DDX1, DDX19B, DDX20, DDX39A, DMPK, EEF1A1, EIF3G, ERAL1, XOSC4, FAM46A, FAM98A, FKBP3, FXR2, G3BP2, GLTSCR2, GSPT2, GTF2F1, GTPBP10, HADHB, HDGF, hnRNPE1, HNRPDL, HSPB1, KIAA1324, LARP1, LARP4, LARP4B, LIN28A, LUC7L, MAK16, MATR3, MBNL2, MEPCE, MRPL39, MTDH, NDUFV3, NUFIP2, NUSAP1, PABPC1, PABPC5, PCBP4, PEG10, PPAN, PPIL4, PRPF3, PRPF31, PRRC2B, PTRH1, PUS7, RBM33, RBM38, RBMX2, RPL10A, RPL14, RPL15, RPLP0, RPS20, RPUSD3, RPUSD4, RTN4, SERBP1, SF3A3, SFRS10, SFRS13A, SFRS2IP, SLC7A9, SMN1, SPATS2L, SRSF5, SRSF8, THOC1, TRA2A, TRIM39, TUFM, UBAP2L, UTP23, XPO5, XRN1, YWHAE, or ZRANB2.

RNA-binding proteins (RBPs) have roles in controlling the fate of RNAs including the modulation of pre-mRNA splicing, RNA modification, translation, stability, and localization. RBPs are a group of proteins that interact with RNA using an array of strategies from well-defined RNA-binding domains to disordered regions that recognize RNA sequence and/or secondary structures.

As used herein, "RNA-RBP complex" can refer to a ribonucleoprotein complex comprising an RNA-binding protein (RBP) bound to a double or single stranded RNA in a cell. In some embodiments, the RNA-binding protein is bound to a single stranded RNA in a cell. In some embodiments, an RNA-RBP complex is produced by crosslinking an RNA binding protein to an RNA fragment in a biological sample.

RNA Structure Probing Reagent

As used herein, an "RNA structure probing reagent" can refer to a reagent used to determine or assay the structure of nucleic acids (e.g., DNA, RNA). When a structured RNA is reacted with a probing reagent, the probing reagent can form a covalent adduct on the RNA at the site of reaction. In some embodiments, the position of the adduct on the RNA can be used to determine the structure profile along the structured RNA.

In some embodiments, the RNA structure probing reagent comprises 2-methylnicotinic acid imidazolide (NAI), dimethyl sulfate (DMS), 1-methyl-7-nitroisatoic anhydride (1M7), 1-methyl-6-nitroisatoic anhydride (1M6), N-methylisatoic anhydride (NMIA), 2-methylnicotinic acid imidazolide-azide (NAI-N3), Nicotinoyl azide (NaZ), Nicotinoyl azide (NaZ-N3), 2-aminopyridine-3-carboxylic acid imidazolide (2A3), Carbodiimide N-cyclohexyl-N'-(2-morpholinoethyl)carbodiimide metho-p-toluenesulfonate (CMC), Isoquinoline-6-carboxylic acid imidazolide (I6), Indoline-5-carboxylic acid imidazolide (I5), 1-Methylimidazole-4-carboxylic acid imidazolide (1M4), 6-Aminopyridine-3-carboxylic acid imidazolide (6A3), Benzotriazole-5-carboxylic acid imidazolide (B5), Nicotinic acid imidazolide (NIC), 3-Azaisatoic anhydride (3AIA), 2-methyl-3-furoic acid imidazolide (FAI), 2-methyl-3-furoic acid imidazolide-azide (FAI-N3), N-propanone isatoic anhydride (NPIA), 5-nitroisatoic anhydride (5NIA), azido-kethoxal (N3-kethoxal), Glyoxal, Methylglyoxal, Phenylglyoxal, 1-ethyl-3-(3-dimethylaminopropyl)carbodiimide (EDC), 4'-aminomethyltrioxalen (AMT), Psoralen-triethylene glycol azide, or Amotosalen. In some embodiments, the RNA structure probing reagent is 2-methylnicotinic acid imidazolide (NAI). In some embodiments, the RNA structure probing reagent is dimethyl sulfate (DMS).

SHAPE, CLIP and Variations Thereof

As used herein, "RNA footprinting" is a technique of identifying specific RNA nucleotides that interact with protein. In some embodiments, RNA footprinting uses RNA-reactive reagents in the absence of protein to identify nucleotides that interact with protein residues.

Selective 2-hydroxyl acylation analyzed by primer extension (SHAPE) is a method that can be used to interrogate RNA structure at single-nucleotide resolution using structure probing reagents that react with 2'-hydroxyl groups on the RNA. Similar to footprinting, an RNA structure probing technique, in vivo click selective 2-hydroxyl acylation analyzed by primer extension (icSHAPE) can be used to demonstrate differences in structure probing data transcriptome-wide between in vivo and in vitro samples.

Footprinting selective 2-hydroxyl acylation analyzed by primer extension (fSHAPE) is a method that compares protein-absent and protein-present conditions to identify transcriptome-wide footprints on RNA. In some embodiments, fSHAPE can be used for in vivo footprinting and extract RNA-protein footprints transcriptome-wide. In some embodiments, fSHAPE can be used in human cell lines. In some embodiments, the human cell lines can include K562, HepG2, 293T, and HeLa cell lines. In some embodiments, fSHAPE can detect nucleobases that are hydrogen bonded to proteins with high specificity and sensitivity. In some embodiments, fSHAPE can be used to identify specific RNA-protein complexes and detecting known RNA elements. However, fSHAPE can usually only produce high quality data across the most highly abundant transcripts in the cell. fSHAPE can require much higher read coverages compared to typical RNA-sequencing assays in order to produce accurate data, thereby presenting technical challenges when collecting data for non-abundant transcripts. Therefore fSHAPE, like many transcriptome-wide RNA-sequencing techniques, suffer from poor data collection of transcripts that are not highly abundant in a cell.

Existing crosslinking and immunoprecipitation (CLIP) methods also identify RNA nucleotides that bind proteins of interest. This technique only identifies an approximate binding site of a given protein, which may be hundreds of nucleotides in length. Enhanced crosslinking and immunoprecipitation (eCLIP) is a modified method of mapping binding sites of RNA binding proteins (RBPs). eCLIP is an antibody-based technique that uses UV radiation to crosslink RNA binding proteins to a target RNA that they are bound to. In some embodiments, eCLIP can be used as a method for high-throughput mapping of protein-RNA binding sites, but the resolution remains poor.

CLIP methods generally require proteins of interest to be present in the sample, while fSHAPE methods require using a protein-removed sample. In some embodiments, the use of structure probing agents in fSHAPE methods presents technical challenges for eCLIP methods. In some embodiments, the crosslinking required in eCLIP presents a technical challenge with producing accurate results by fSHAPE methods. Therefore identifying specific nucleotides where RNA and RBP interact with high specificity while strategically enriching data for transcripts bound by the RBP using these methods was not obvious.

Methods of Identifying a Nucleobase on RNA that Interacts with an RBP

Provided herein are methods of identifying an RNA nucleobase that interacts with an RNA binding protein (RBP) including (a) crosslinking the RNA binding protein to an RNA fragment in a biological sample; (b) detecting an RNA-RBP complex, wherein the RNA-RBP complex comprises the RNA fragment bound by the RNA binding protein; (c) isolating the RNA fragment of the RNA-RBP complex; and (d) profiling the isolated RNA fragment bound by the RNA binding protein.

In some embodiments, the biological sample includes (i) a first plurality of cells, wherein the first plurality of cells is contacted with a RNA structure probing reagent prior to the crosslinking step (a); and a second plurality of cells, wherein the second plurality of cells is contacted with the RNA structure probing reagent after the isolating step (c). In some embodiments, the detecting step (b) further comprises contacting the RNA-RBP complex with an RBP specific antibody, and immunoprecipitating the RNA-RBP complex with the RBP specific antibody. In some embodiments, the isolating step (c) further comprises treating the immunoprecipitated RNA-RBP complex with a protease. In some embodiments, the profiling step (c) further comprises sequencing all or a part of a sequence of the isolated RNA fragment or a complement thereof.

Also provided herein are methods of identifying an RNA nucleobase that interacts with an RNA binding protein (RBP) including (a) providing a biological sample, wherein the biological sample comprises a first plurality of cells and a second plurality of cells; (b) contacting the first plurality of cells with an RNA structure probing agent; (c) crosslinking the RNA binding protein to an RNA fragment in the biological sample; (d) detecting an RNA-RBP complex, wherein the RNA-RBP complex comprises the RNA fragment bound by the RNA binding protein; (e) isolating the RNA fragment of the RNA-RBP complex; (f) contacting the RNA fragment from the second plurality of cells with the RNA structure probing agent; and (g) profiling (i) the RNA fragment bound by the RNA binding protein from the first plurality of cells and (ii) the RNA fragment bound by the RNA binding protein from second plurality of cells, thereby identifying the RNA nucleobase of the RNA fragment that interacts with the RNA binding protein.

In some embodiments, the detecting step (d) further comprises contacting the RNA-RBP complex with an RBP specific antibody, and immunoprecipitating the RNA-RBP complex using the RBP specific antibody. In some embodiments, the isolating step (e) further comprises treating the immunoprecipitated RNA-RBP complex with a protease. In some embodiments, the profiling step (g) further comprises sequencing all or a part of a sequence of the isolated RNA fragment or a complement thereof.

Also provided herein are methods of identifying hydrogen bond interactions between an RNA molecule and an RNA binding protein (RBP) including (a) crosslinking the RNA binding protein to an RNA fragment in a biological sample; (b) detecting an RNA-RBP complex, wherein the RNA-RBP complex comprises the RNA fragment bound by the RNA binding protein; (c) isolating the RNA fragment of the RNA-RBP complex; and (d) profiling the isolated RNA fragment bound by the RNA binding protein, thereby identifying a hydrogen bond interaction between an RNA nucleobase and the RNA binding protein.

In some embodiments, the biological sample includes (i) a first plurality of cells, wherein the first plurality of cells is contacted with a RNA structure probing reagent prior to the crosslinking step (a); and (ii) a second plurality of cells, wherein the second plurality of cells is contacted with the RNA structure probing reagent after the isolating step (c). In some embodiments, the detecting step (b) further comprises contacting the RNA-RBP complex with an RBP specific antibody, and immunoprecipitating the RNA-RBP complex with the RBP specific antibody. In some embodiments, the isolating step (c) further comprises treating the immunoprecipitated RNA-RBP complex with a protease. In some embodiments, the profiling step (c) further comprises sequencing all or a part of a sequence of the isolated RNA fragment or a complement thereof.

In some embodiments, the RNA nucleobase interacts with the RNA binding protein via hydrogen bond. In some embodiments, the crosslinking can include thermal crosslinking, chemical crosslinking, physical crosslinking, ionic crosslinking, photo-crosslinking, free-radical initiation crosslinking, an addition reaction, condensation reaction, water-soluble crosslinking reactions, oxidative crosslinking, irradiative crosslinking (e.g., x-ray, electron beam), or combinations thereof. In some embodiments, the crosslinking comprises formaldehyde crosslinking, UV crosslinking, or psoralen crosslinking. In some embodiments, ethanol is not included in the structure probing workflow. In some embodiments, beta-mercaptoethanol (i.e., 2-mercaptoethanol, BME, 2BME, 2-ME) is included in the structure probing workflow.

Sequencing of polynucleotides (e.g., an RNA fragment) can be performed by various commercial systems. More generally, sequencing can be performed using nucleic acid amplification, polymerase chain reaction (PCR) (e.g., digital PCR and droplet digital PCR (ddPCR), quantitative PCR, real time PCR, multiplex PCR, PCR-based singleplex methods, emulsion PCR), and/or isothermal amplification. Other examples of methods for sequencing genetic material include, but are not limited to, DNA hybridization methods (e.g., Southern blotting), restriction enzyme digestion methods, Sanger sequencing methods, next-generation sequencing methods (e.g., single-molecule real-time sequencing, nanopore sequencing, and Polony sequencing), ligation methods, and microarray methods. Additional examples of sequencing methods that can be used include targeted sequencing, single molecule real-time sequencing, exon sequencing, electron microscopy-based sequencing, panel sequencing, transistor-mediated sequencing, direct sequencing, random shotgun sequencing, Sanger dideoxy termination sequencing, whole-genome sequencing, sequencing by hybridization, pyrosequencing, capillary electrophoresis, gel electrophoresis, duplex sequencing, cycle sequencing, single-base extension sequencing, solid-phase sequencing, high-throughput sequencing, massively parallel signature sequencing, co-amplification at lower denaturation temperature-PCR (COLD-PCR), sequencing by reversible dye terminator, paired-end sequencing, near-term sequencing, exonuclease sequencing, sequencing by ligation, short-read sequencing, single-molecule sequencing, sequencing-by-synthesis, real-time sequencing, reverse-terminator sequencing, nanopore sequencing, MS-PET sequencing, and any combinations thereof. In some embodiments, the sequencing comprises high-throughput sequencing.

In some embodiments, the methods described herein can precisely detect nucleobases that hydrogen bond with protein and predict binding sites of known RBPs. In some embodiments, the methods can enable assessment of less abundant RNA-protein complexes by integrating SHAPE and fSHAPE with crosslinking and immunoprecipitation (eCLIP) of desired RBPs. In some embodiments, the methods described herein can also be referred to as fSHAPE-eCLIP. In some embodiments, the methods described herein can also be referred to as SHAPE-eCLIP. In some embodiments, the methods described herein can also be referred to as fSHAPE-CLIP. In some embodiments, the methods can be used for in vivo footprinting and extract RNA-protein footprints transcriptome-wide. In some embodiments, the methods can be used to detect hydrogen bonding in human cell lines. In some embodiments, the human cell lines can include K562, HepG2, 293T, and HeLa cell lines. In some embodiments, the methods can detect nucleobases that are hydrogen bonded to proteins with high specificity and sensitivity. In some embodiments, the methods can be used to identify specific RNA-protein complexes and detecting known RNA elements.

The methods described herein (e.g., footprinting SHAPE-eCLIP (fSHAPE-eCLIP)), can be used to identify the interaction mechanism and location of RBPs on RNA and understand specific cellular RNA interactions in protein-RNA complexes. The methods described herein (e.g., footprinting SHAPE-eCLIP (fSHAPE-eCLIP)) applies selective 2'-hydroxyl acylation analyzed by primer extension (SHAPE) on in vivo transcripts compared to protein absent transcripts to identify transcriptome-wide footprints (fSHAPE) on RNA. As presented herein, fSHAPE precisely detects nucleobases that hydrogen bond with protein and that fSHAPE patterns can predict binding sites of known RBPs. Furthermore, fSHAPE-eCLIP enables assessment of less abundant RNA-protein complexes by integrating SHAPE and (SHAPE with crosslinking and immunoprecipitation (eCLIP) of desired RBPs. fSHAPE-eCLIP also enables more precise detection of the nucleobases that interact with desired RBPs than does eCLIP alone, due to its detection of RNA-protein hydrogen bonds at nucleotide-resolution. In some embodiments, fSHAPE-eCLIP combines the concept of RNA footprinting with existing SHAPE (icSHAPE or SHAPE-MaP) techniques to enable footprinting of thousands of in vivo transcripts. In some embodiments, fSHAPE-eCLIP modifies the data collection and analysis of icSHAPE to specialize in identifying protein-interacting nucleotides.

Kits

A "kit," as used herein, typically includes a package or an assembly including one or more of the compositions or devices of the invention, and/or other compositions or devices associated with the invention, as previously described. Each of the compositions of the kit, if present, may be provided in liquid form (e.g., in solution), or in solid form (e.g., a dried powder). In certain embodiments, one or more of the compositions may be constitutable or otherwise processable (e.g., to an active form), for example, by the addition of a suitable solvent or other species, which may or may not be provided with the kit. A kit may further include other compositions or components associated with the invention include, but are not limited to, solvents, surfactants, diluents, salts, buffers, emulsifiers, chelating agents, fillers, antioxidants, binding agents, bulking agents, preservatives, drying agents, packaging materials, tubes, bottles, filters, containers, tapes, or adhesives. A kit may include instructions in any form that are provided in connection with the compositions of the invention in such a manner that one of ordinary skill in the art would recognize that the instructions are to be associated with the compositions of the invention. The instructions may be provided in any form recognizable by one of ordinary skill in the art as a suitable vehicle for containing such instructions. For example, written or published, verbal, audible (e.g., telephonic), digital, optical, visual (e.g., videotape, DVD, etc.) or electronic communications (including Internet or web-based communications), provided in any manner.

Provided herein are kits including (a) an RBP specific antibody, wherein the RBP specific antibody interacts to an RNA binding protein bound to an RNA fragment in a biological sample, thereby facilitating immunoprecipitation of an RNA-RBP complex using the RBP specific antibody, wherein the RNA-RBP complex comprises the RNA fragment bound by the RNA binding protein; (b) an RNA structure probing agent; (c) a protease, and (d) instructions to use the kit to identify an RNA nucleobase that interacts with the RNA binding protein.

In some embodiments, the instructions comprise instructions to crosslink the RNA binding protein to the RNA fragment in the biological sample, thereby producing the RNA-RBP complex. In some embodiments, the crosslinking comprises formaldehyde crosslinking, UV crosslinking, or psoralen crosslinking. In some embodiments, a crosslinking agent, for example formaldehyde or psoralen, is included in the kit. In some embodiments, the instructions indicate that ethanol is not included in the structure probing workflow. In some embodiments, the instructions indicate beta-mercaptoethanol (i.e., 2-mercaptoethanol, BME, 2BME, 2-ME) is included in the structure probing workflow.

In some embodiments, the kit includes an RNA structure probing reagent. In some embodiments, the RNA structure probing reagent comprises 2-methylnicotinic acid imidazolide (NAI), dimethyl sulfate (DMS), 1-methyl-7-nitroisatoic anhydride (1M7), 1-methyl-6-nitroisatoic anhydride (1M6), or N-methylisatoic anhydride (NMIA). In some embodiments, the RNA structure probing agent is 2-methylnicotinic acid imidazolide (NAI), 2-methylnicotinic acid imidazolide-azide (NAI-N3), Nicotinoyl azide (NaZ), Nicotinoyl azide (NaZ-N3), 2-aminopyridine-3-carboxylic acid imidazolide (2A3), Carbodiimide N-cyclohexyl-N'-(2-morpholinoethyl)carbodiimide metho-p-toluenesulfonate (CMC), Isoquinoline-6-carboxylic acid imidazolide (I6), Indoline-5-carboxylic acid imidazolide (I5), 1-Methylimidazole-4-carboxylic acid imidazolide (1M4), 6-Aminopyridine-3-carboxylic acid imidazolide (6A3), Benzotriazole-5-carboxylic acid imidazolide (B5), Nicotinic acid imidazolide (NIC), 3-Azaisatoic anhydride (3AIA), 2-methyl-3-furoic acid imidazolide (FAI), 2-methyl-3-furoic acid imidazolide-azide (FAI-N3), N-propanone isatoic anhydride (NPIA), 5-nitroisatoic anhydride (SNIA), azido-kethoxal (N3-kethoxal), Glyoxal, Methylglyoxal, Phenylglyoxal, 1-ethyl-3-(3-dimethylaminopropyl)carbodiimide (EDC), 4'-aminomethyltrioxalen (AMT), Psoralen-triethylene glycol azide, or Amotosalen.

EXAMPLES

The disclosure is further described in the following examples, which do not limit the scope of the disclosure described in the claims.

Cell Culture

Human K562, Hepg2, and HeLa cells were acquired from ATCC. K562 cells were cultured in RPMI 1640 medium (Gibco) with 10% FBS (Corning) and 1% penicillin/streptomycin (Gibco). HepG2 and HeLa cells were cultured in DMEM media (Gibco) with 10% FBS 1% penicillin/streptomycin. All cells were grown at 37° C. in 5% CO2 and routinely tested with MycoAlert PLUS (Lonza) for mycoplasma contamination.

fSHAPE

In vivo click selective 2-hydroxyl acylation and profiling experiment (icSHAPE) was performed on cells from K562, HepG2, and HeLa cell lines under both +protein ("in vivo") and −protein ("in vitro") conditions. Briefly, in the +protein condition, 20 million cells were treated with 100 mM NAI-N3 at 37° C. for 5 minutes. Cells were centrifuged and supernatant removed to stop the reaction. RNA was extracted from cells with a standard Trizol extraction. Ethanol was added to the aqueous phase, which was isolated and column-purified (Zymo). In the −protein condition, RNA was Trizol extracted from cells as above and column-purified, leaving RNA purified from protein. Purified RNA was heated in water to 95° C. for 2 minutes, then flash-cooled on ice. Denatured RNA was added to SHAPE folding buffer (333 mM HEPES, pH 8.0, 20 mM MgCl2, 333 mM NaCl) and RNA allowed to re-fold at 37° C. for 10 min. Re-folded −protein RNA was probed with 100 mM NAI-N3 for 10 minutes, Reaction was stopped with the addition of buffer RLT (Qiagen) and ethanol, followed by column purification. Treated RNA from +protein and −protein conditions were poly(A)+ selected twice, then biotin-labeled on NAI-N3 adducts via click reaction with DIBO-biotin (Molecular Probes). RNA was fragmented and end repaired, followed by 3' end ligation with RNA linker and size selection. RNA underwent reverse transcription and magnetic streptavidin bead selection for biotin-labeled RNA: cDNA hybrids. cDNA was circularized, amplified, and size-selected. Libraries were sequenced to a depth of approximately 200 million reads. Untreated samples were also prepared for each cell line as above, in which cells were treated with DMSO rather than NAI-N3 and RNA ligated to a biotin-conjugated RNA linker to facilitate RNA pull-down in the absence the click reaction with DBO-biotin.

fSHAPE Data Analysis

Reads were barcode trimmed with cutadapt 1.14, mapped to GRCh38 with Star aligner version 2.4.0i (parameters: —outSAMstrandField intronMotif—outFilterIntronMotifs RemoveNoncanonical), and de-duplicated with UMItools 0.5.0. Aligned, unique reads were separated based on chromosome and strand (genome build GrCh38). To calculate the frequency of reverse transcription-induced truncation events, 5' end read coverage (truncation events) and total read coverage at each position across the genome was counted via bedtools 2.25.0 (parameters: genomcov-5-strand-dz and genomcov-split-strand-dz, respectively). Script bedReactivities.py (github.com/meracorley/fSHAPE) was used to calculate normalized drop-off frequencies (fSHAPE reactivities) at each nucleotide in every transcript (NCBI RefSeq Hg38). Special normalization procedures were implemented to handle the artifact of drop-off events dropping to 0 immediately 5' to a gap in total read coverage (FIGS. 15A-15B), which erroneously reports these regions' drop-off frequencies as 0 rather than "no data." To address the "5' drop-off" artifact, a Hidden Markov Model was trained on K562 "−protein" SHAPE total coverage data from several transcripts with high coverage interrupted by gaps. Each nucleotide was categorized as state '0' if its coverage was below 200, and state '1' otherwise, 200 being the previously determined cutoff of coverage that produces acceptable reproducibility between replicates. States were used to train a two-state multinomial Hidden Markov Model with hmmlearn 0.2.1 in scikit-learn, which labels regions as "1" (covered) or "0" (no coverage). Total read coverage tends to be monotonic, such that when total read coverage drops to 0 it tends to do so gradually. It was found that the 5' drop-off artifacts tended to occur where the total coverage peaked before a gap in total coverage. Thus, once total coverage regions are categorized via the Hidden Markov Model, the local maxima of total coverage occurring before any 'no coverage' regions is set as the "true" starting point of the coverage gap and the drop-off rate is assessed as "no data."

fSHAPE reactivities are calculated as the drop-off frequency in the +protein sample minus drop-off rate in the −protein sample for each nucleotide, divided by a normalization factor based on all the raw reactivities in the given region as in the ShapeMapper 2.0 pipeline. Briefly, the normalization factor for each transcript is calculated as the average of the top 10% of values below a cutoff—either the highest 10% of values or 1.5*(the value at the top of the third quartile minus the value at the top of the first quartile), whichever includes fewer values. Final fSHAPE reactivities are output in the form of .map and .rx files for each transcript in the human reference transcriptome (NCBI RefSeq Hg38), GEO access https://www.ncbi.nlm.nih.gov/geo/query/acc.cgi?acc=GSE149767. Files denote the fSHAPE reactivity at each nucleotide for each replicate (.rx format) or the nucleotide number, average reactivity, variance, and base identity (.map format). Nucleotides without reactivity data are denoted as "−999."

Correlations between Replicates

Correlation coefficients between fSHAPE replicates were calculated for transcripts within each cell sample as follows. Transcript per million (TPM) expression was calculated for each transcript in each cell line (K562, HepG2, HeLa, 293T) with Sailfish 0.10.0. For each gene, a single transcript with highest TPM was selected. If TPM>150 and the transcript contained data across >30% of its length, the correlation coefficient between the cell sample's replicates was taken in rolling 50 nucleotide windows across the transcript and averaged. Similarly for SHAPE7 eCLIP and fSHAPE-eCLIP replicates, correlation coefficients were calculated in rolling 50 nucleotide windows between all transcripts with data covering >30% of their length.

Hydrogen Bond Analyses 10 human RNA-protein x-ray crystallography structures were selected for their representations of portions of human transcripts (rather than random RNA fragments) that also have fSHAPE reactivity data in at least one cell line. Structures were downloaded from the protein databank (PDB) and matched to 12 regions in transcripts that are represented by the RNA fragments in the structures. fSHAPE reactivities from all four cell lines were extracted for the matching transcript regions and re-normalized by region and outliers removed. Hydrogen bonds in PDB files were assessed by HBPLUS, which outputs all detected hydrogen bonds between any two moieties, including water molecules (parameters: −d 3.35 −h 2.7). RNA-protein and RNA-RNA hydrogen bonds occurring with each moiety (backbone, 2'-OH, or base) of each nucleotide in RNA-protein structures were compiled and quantified by bond length (q) (script: process_hb2.py from github.com/meracorley/hbplus_tools, parameters: −R). For a given model of hydrogen bonds (FIG. 2B), nucleotides in each structure were labeled as "cases" if their set of hydrogen bonds fulfilled the model and "controls" if not. fSHAPE reactivities corresponding to cases and controls were assessed with receiver operator characteristic (ROC) curves (R package pROC 1.14.0; expect controls<cases), modulating q to maximize the area under each curve.

Base-Pairing Probabilities and Shannon Entropy

High quality transcripts were selected as above (correlations between replicates). Nucleotides with fSHAPE reactivities above 4.0 (top 1%) were selected and 200 base regions around them were defined. Sequences in the 200 base regions were extracted and their base pairing probability matrix predicted with RNAfold 2.4.14 (parameters: −p), supported by icSHAPE reactivities calculated with "−protein" samples normalized to untreated samples in each cell line (available in GEO, GSE149767). Base pairing probabilities and Shannon entropies were calculated for each nucleotide (script: shannonEntropy_mafold.py from github.com/meracorley/RNAstructure_tools) in these transcript regions using the predicted base pairing probability matrices. The central 50 bases around the high fSHAPE-valued base(s) were taken as the "high fSHAPE region" while the flanking 50 base regions were taken as "flanking regions," and Shannon entropies were averaged in each of these sub-regions for each transcript and plotted. Similarly, the base pairing probability matrices for the above 200 base transcript regions were used to calculate the sum of base pairing probabilities for each nucleotide (script: getBPprobs_mafold.py from github.com/meracorley/RNAstructure_tools). Bases were grouped by high (fSHAPE>2.5), medium (−2.0 <fSHAPE<2.0), or low fSHAPE (fSHAPE<−2.5) reactivity and plotted according to base pairing probability.

Predicting New Iron Response Elements (IREs)

Sequence matches to the IRE motif were searched transcriptome-wide. For multiple matching transcript isoforms per gene, the transcript with the highest expression was selected. Sequence matches with fSHAPE data were compared to the FTL IRE fSHAPE profile in the form of a Pearson correlation coefficient. Matches that exceeded a correlation coefficient of 0.8 and whose fSHAPE values at positions 1 and 7, 8, or 9 of the sequences motif were greater than 1.0 were selected as candidate IREs. Minimum free energy structures for each candidate IRE were predicted with RNAfold 2.4.14 using default settings to further select for candidates for electromobility shift assays.

Electromobility Shift Assays

To test for putative iron response element (IRE) binding to IRP1, RNA oligonucleotides were obtained for four predicted IREs, CDC34, COASY, SLC2A4RG, H19.

RNA oligonucleotides were 3' biotinylated (Fisher Scientific cat #20160MI) at 16° C. for 2 hours and purified (Zymo Research cat #1080). The labeled RNA control from biotin labeling kit (Fisher Scientific cat #20160MI), which is the FTL IRE, was used as the positive control RNA. The "Hairpin 3" from RN7SK (Diribarne and Bensaude, 2009) served as a negative control: the DNA oligonucleotide was in vitro transcribed (NEB T7 cat #E2040S), purified and size selected with 6% urea-PAGE, then biotin labeled and purified as above. IRP1 protein was supplied in the form of human liver cytosolic extract (Life Technologies cat #HMCYPL). Conditions for all 20 uL EMSA binding reactions, 2 uL 10×"RNA EMSA" buffer (100 mM HEPES, pH=7.3, 200 mM KCl, 10 mM MgCl2, 10 mM DTT), 2 uL 50% glycerol. Each RNA was tested under two conditions: biotin-labeled RNA alone, and biotin-labeled RNA plus cytosolic liver extract. The FTL positive control reactions contained 125 fmol biotin-labeled FTL IRE RNA and 2 ug cytosolic liver extract, RN7SK negative control contained 100 fmol and 2 ug liver cytosol. 650 fmol CDC34 and COASY with 2 ug liver cytosol, 650 fmol SLC2A4RG and H19 biotin-labeled RNA with 40 ug liver cytosol. Supershift assays were performed on FTL and CDC34 IREs, where 125 fmol and 650 fmol of biotin-labeled RNA was incubated alone or with 0.5 ug and 20 ug liver cytosol, respectively.

Reactions were assembled and incubated at 25° C. for 30 minutes. 2 ug of either IRP1 (SCBT E-12 lot #H0117), IRP2 (SCBT 4G11 lot #F317), or Immunoglobulin G antibodies (mouse) were added to FTL and CDC34 samples and incubated for 10 minutes further. All assays were then loaded onto a 6% native TBE gel with TBE loading buffer (Life Technologies cat #LC6678) and run at 100V for 40 minutes in 0.5×TBE buffer. Gel was subsequently transferred to nylon membrane (Amersham Hybond -XL GE Healthcare) via standard transfer setup in cold 0.5×TBE buffer at 35V for 30 minutes. RNA was crosslinked to membrane with UV light at 120 mJ/cm2 for 1 minute. Membrane was processed with chemiluminescent nucleic acid detection module (Thermo Fisher cat #89880) followed by exposure to film.

Quantification of Candidate IRE-Containing Transcripts in Response to Iron

K562 cells were grown in RPMI 1640 medium supplemented with 10% fetal bovine serum. At a density of 5×105 per mL, 1.25M cells were treated for 24 hr, in biological triplicates, with 20 mg/ml ammonium iron(III) citrate (FAC, Acros Organics) or 0.1 mM deferoxamine mesylate (DFOM, Sigma-Aldrich). K562 cells were collected, centrifuged at 300×g for 3 min, washed with DPBS, and centrifuged again. Cell pellets were resuspended in TRIzol Reagent (Invitrogen) and RNA was extracted using the Direct-zol RNA Miniprep Kit (Zymo Research).

Concentrations of purified RNA were determined using a Nanodrop spectrophotometer. Equal amounts of cDNA were synthesized using the SuperScript III First-Strand Synthesis System (Invitrogen) and 25 pmol oligo-dT and 25 ng random hexamer primers. qPCR was performed, in technical triplicates, using a cDNA equivalent of approximately 25 ng of total RNA, 10 uM each of gene-specific forward and reverse primers (see Table S4), 1 and Power SYBR Green Master Mix (Applied Biosystems). Quantitative PCR was performed at 95° C. for 10 min and 40 cycles of 95° C. for 15 s and 60° C. for 1 min. Treatment-dependent target gene fold expression change was calculated using the ΔΔCt method by first normalizing technical triplicates to a housekeeping gene, RPL4, then normalizing treated to untreated technical triplicates. The resulting ΔΔCt values were averaged and used to calculate fold change in expression (2^(−ΔΔCt)) for each set of technical triplicates. These were subsequently averaged to calculate fold expression change for each gene target and in each treatment condition. Significance was calculated using a paired t-test.

SHAPE-e CLIP 40 million K562 cells per sample were resuspended in 4 mL RPMI media (Gibco) in 10 cm plates. Cells were injected with 100 uL pure DMS (treated samples) or left untreated, mixed, and incubated at 37 C for 3 minutes. Cells were placed on chilled metal plate and crosslinked (lids removed) with UV-C light at 4000 U for 2 minutes. All samples were treated with 2 mL 40% 2-mercaptoethanol to quench excess DMS. (SHAPE-eCLIP samples treated with NAI rather than DMS used the same starting material and volumes, but were treated with 200 uL 2M NAI in DMSO (Neta biosciences) or 200 uL DMSO, mixed, and incubated at 37° C. for 10 minutes, then crosslinked as above.) Crosslinked cells were spun down, supernatant removed, and resuspended in cold phosphate buffered saline (PBS). PBS wash was repeated twice; cell pellets were flash frozen on dry ice and stored at −80° C. Cell pellets from treated and untreated samples were used as the starting point for single-end enhanced crosslinking and immunoprecipitation on SLBP, with modifications. Briefly, cells lysates were sonicated and briefly RNase treated to select for RBP protected RNA fragments, then immunoprecipitated overnight with SLBP antibody (MBLI) and anti-rabbit secondary antibody-conjugated magnetic beads. 2% of each immunoprecipitated (IP) sample was saved as Input control. (Input controls are not needed for both reagent treated and untreated IP samples; one set is sufficient). IP samples were washed on magnet and underwent alkaline phosphatase and polynuceotide kinase treatment followed by RNA 3' linker ligation (InvRiL19). IP samples were decoupled from beads both IP and Input samples run on a 4-12% Bis-Tris gel. Samples were transferred from gel to nitrocellulose membrane at 4° C. Bands at the appropriate SLBP protein size plus 75 kDa above were cut from the nitrocellulose membrane. RNA was eluted and protein removed with proteinase K treatment and RNA spin column clean-up (Zymo). Input samples then underwent alkaline phosphatase and polynuceotide kinase treatment followed by RNA 3' linker ligation. Both IP and Input samples then underwent cDNA synthesis. Importantly, RNA reverse transcription was modified to perform mutational profiling of the DMS-probed transcripts. Specifically, 9 uL of each RNA sample was added to 1 uL of 5 uM reverse primer (InvAR17) and 1 uL of 10 mM dNTPs, heated to 65° C. for 2 minutes, then placed on ice. 5.56 uL water, 2 uL 10× SHAPE buffer (500 mM Tris-HCl, pH 8.0, 750 mM KCl), 1 uL 0.1 M DTT, 0.2 uL RNase inhibitor, 1 uL Superscript II, and 0.24 uL 500 mM manganese chloride (to a concentration of 6 mM) was added to each sample and incubated at a temperature of 45° C. for 3 hours. cDNA was cleaned with Silane beads, ligated to a 5' Illumina compatible linker (InvRand3Tr3), and quantified via qPCR. Libraries were PCR amplified with barcoded Illumina compatible primers based on individual qPCR quantification, cleaned with Ampure xP beads, and size selected to a final size of 180-350 nucleotides with a 3% low melting temperature agarose gel (NuSieve GTG, cat #50080). Each sample library was sequenced to a depth of approximately 40 million reads.

SHAPE-eCLIP 40 million K562 cells per sample were resuspended in 4 mL RPMI media (Gibco) in 10 cm plates. Cells were injected with 200 uL 2M NAI in DMSO (Neta biosciences) for the "+protein" sample or 200 uL DMSO for the "−protein" sample, mixed, and incubated at 37° C. for 10 minutes. Cells were placed on chilled metal plate and crosslinked (lids removed) with UV light at 4000 U for 2 minutes. Crosslinked cells were spun down, supernatant removed, and resuspended in cold PBS. PBS wash was repeated twice; cell pellets were flash frozen on dry ice and stored at −80° C. Cell pellets from NAI-treated and untreated samples were used as the starting point for single-end enhanced crosslinking and immunoprecipitation on SLBP and ACO1 combined with structure probing. Cells lysates were sonicated and briefly RNase treated to select for RBP protected RNA fragments, then immunoprecipitated overnight with SLBP antibody (MBLI) and anti-rabbit secondary antibody-conjugated magnetic beads. 4% of each immunoprecipitated (IP) sample was saved as Input control. (Technically Input controls are not needed for both +protein and −protein IP samples; one set is sufficient). IP samples were washed on magnet. 20% of each IP sample and 50% of each Input control was saved for test western blot confirming successful pull-down of protein. The remainder of each sample was treated with proteinase K to remove protein, and the resulting RNA was column purified (Zymo). +protein samples treated with NAI at the cell stage were set aside. Samples that were not treated with NAI are the "−protein" samples, and were refolded and probed with NAI. In detail, 11.4 uL "in vitro" samples were heated to 95° C. for 2 minutes, placed on ice to cool, then added to 6.6 uL 3.3×SHAPE folding buffer (333 mM HEPES, pH 8.0, 20 mM MgCl2, 333 mM NaCl), with 1 uL RNase inhibitor and folded at 37° C. for 5 minutes. 1 uL 2M NAI was added, and samples were further incubated at 37° C. for 10 minutes. Samples were cleaned with a Zymo column to remove excess NAI. As in eCLIP, both "+protein" and "−protein" RNA was then FastAP and PNK treated, followed by Zymo column purification. Samples underwent 3' RNA linker ligation (InvRiL19), followed by denaturation at 65 C for 3 minutes in RNA running buffer and purification on a 6% TBE Urea gel (180V for 40 minutes). Each sample was spaced with a low-range RNA ladder (NEB). Gel was stained for 5 minutes in a SYBR Gold solution. Samples were cut from the gel in the range of 50-200 bases, and RNA was isolated using a Zymo small RNA PAGE recovery kit. RNA was reverse transcribed according to the mutational profiling method. Specifically, 9 uL of each RNA sample was added to 1 uL of 5 uM reverse primer (InvAR17) and 1 uL of 10 mM dNTPs, heated to 65 C for 2 minutes, then placed on ice. 5.56 uL water, 2 uL 10×SHAPE buffer [500 mM Tris-HCl, pH 8.0, 750 mM KCl], 1 uL 0.1 M DTT, 0.2 uL RNase inhibitor, 1 uL Superscript II, and (importantly) 0.24 uL 500 mM manganese chloride (to a concentration of 6 mM) was added to each sample and incubated at a temperature of 45° C. for 3 hours. cDNA was cleaned with Silane beads, ligated to a 5' Illumina compatible linker (InvRand3Tr3), and quantified via qPCR. Libraries were PCR amplified with barcoded Illumina compatible primers based on individual qPCR quantification, cleaned with Ampure xP beads, and size selected to a final size of 180-350 nucleotides with a 3% low melting temperature agarose gel (NuSieve GTG, cat #50080). Each sample library was sequenced to a depth of approximately 40 million reads.

SHAPE-eCLIP and fSHAPE-eCLIP Data Analysis

SHAPE-eCLIP. IP and Input sample reads from SHAPE-eCLIP and fSHAPE-eCLIP were trimmed, mapped to the human genome (GrCh37, converted to GrCh38), and deduplicated with the eCLIP pipeline (available at github.com/YeoLab/eclip), which also calls RBP binding peaks in IP samples given the background of Input samples. De-duplicated reads mapped by the eCLIP pipeline from IP samples in SHAPE-eCLIP or fSHAPE-eCLIP were the starting point for SHAPE or fSHAPE data analysis. Total read coverage and mutation events were counted across the genome using sorted, uniquely mapped reads (script countMutationsBam.py), and stored by chromosome. Mutation events indicate nucleotides that formed an adduct with the probing reagent (DMS or NAI). Mutation frequencies at each nucleotide across transcripts were calculated as in fSHAPE analysis, except the hmmlearn adjustment was not necessary and G and U bases are ignored for DMS-treated samples (script bedReactivities.py). Among SHAPE-eCLIP experiments, the untreated sample mutation rates are subtracted from treated mutation rates and normalized to produce SHAPE reactivities. For the fSHAPE-eCLIP experiment, the +protein sample mutation rates are subtracted from −protein mutations rates and normalized to produce fSHAPE reactivities at each nucleotide. Final reactivities are output in the form of .map and .rx files for each transcript in the human reference transcriptome (NCBI RefSeq Hg38), GEO access https://www.ncbi.nlm.nih.gov/geo/query/acc.cgi?acc=GSE149767. Files denote the (f)SHAPE reactivity at each nucleotide for each replicate (.rx format) or the nucleotide number, average reactivity, variance, and base identity (.map format). Nucleotides without reactivity data are denoted as "−999."

Crosslinking Rates in SLBP Binding Sites

5' end coverage and total read coverage at each nucleotide across histone transcripts was calculated (bedtools, parameters: genomcov-5 -strand-dz and genomcov-split-strand-dz, respectively) from mapped SLBP eCLIP reads from the ENCODE project. 5' ends represent RT drop-off (truncation) events and occur more frequently at nucleotides crosslinked to protein (analogous to SHAPE probing). Crosslinking rate at each nucleotide was calculated as the 5' end coverage divided by total coverage and averaged across eCLIP replicates.

Example 1 fSHAPE-eCLIP, SHAPE-eCLIP, or In Vitro SHAPE-eCLIP

Cells were treated with the structure probing reagent NAI or mock treated with DMSO, followed by UV crosslinking to covalently link RNA binding proteins to bound RNA molecules. The following steps were completed for all protocol types: fSHAPE-eCLIP, SHAPE-eCLIP, or "in vitro" SHAPE-eCLIP (FIG. 17).

Cells were grown to ~30-40 million cells per sample. Cells were split into two samples for each treatment condition and each cell sample volume was reduced to 2 mL in plain media. The cells were then UV crosslinked and washed by spinning down, removing supernatant, resuspending the cells in PBS. The cells were lysed to release protein-bound RNA from the cells and a monoclonal antibody was coupled to magnetic beads (Dynabeads M-280) to pull down RNA bound to the protein of interest. Lysed samples were sonicated (Biorupter), thereby assisting cell lysis, shearing chromatin and aiding release of RNA-protein complexes. The antibody beads were then washed and RNA bound by the protein of interest was immunoprecipitated.

For SHAPE-eCLIP samples, RNA was treated and ligated with an adapter, later used for reverse transcription. Non-immunoprecipitated sample controls were referred to as "input" samples, while the remainder of the samples were referred to as immunoprecipitated (IP) samples. The antibody-bound beads were washed with High Salt Wash Buffer, resuspended with FastAP Buffer and then placed on ice. RNA beads were treated with FastAP master mix and PNK master mix. The beads were then washed with cold Wash Buffer and 3' RNA ligation master mix was added to the bead samples to ligate the 3' RNA adapter.

The efficacy of the antibody was verified with a Western blot and RNA from IP and input samples was isolated with gel transfer, for all (fSHAPE-eCLIP, SHAPE-eCLIP, and in vitro SHAPE-eCLIP) samples. The bead samples were washed and the IP and input samples were prepared for gel separation with SDS-PAGE gels. An aliquot from supernatant from the IP bead sample was used in the Western blot, while the remaining supernatant was used for the RNA transfer. Once the protein band appears on Western blot and it indicates the expected size for the given protein being immunoprecipitated, RNA from nitrocellulose membrane after RNA transfer was extracted for all IP and input samples. RNA is extracted from the membrane by adding proteinase K mixture. Then, RNA binding buffer is added to each sample and each sample was transferred to a spin column and centrifuged to purify the RNA. IP samples from either fSHAPE-eCLIP or in vitro SHAPE-eCLIP were then treated with structure probing reagent NAI for in vitro RNA treatment. The isolated RNA was treated with NAI and heated to 37° C. for 5 minutes to re-fold RNA. The treated RNA was then purified with RNA Clean and Concentrator Kit column cleanup, wherein the sample was loaded onto a spin column and centrifuged as the flow-through contained the purified RNA. RNA from input samples for the SHAPE-eCLIP protocol, and all IP and input samples for fSHAPE-eCLIP or in vitro SHAPE-eCLIP protocols was treated and ligated to an adapter that was later used for reverse transcription. FastAP master mix was added to each sample and incubated at 1200 rpm at 37° C. for 10 minutes. PNK master mix was then added to each sample and incubated at 1200 rpm at 37° C. for 20 minutes. To each sample, RNA binding buffer was added and each sample was transferred to a spin column, wherein the final flow-through contained purified RNA. Isolated RNA was treated with 3' RNA ligation master mix (InvRil19 adapter). The samples were cleaned up with Silane magnetic beads by binding the RNA samples to the beads, washing the beads, and eluting the RNA from the beads.

RNA from all samples were reverse transcribed with manganese to perform "mutual profiling" followed by 5' cDNA adapter ligation. To each sample, InvAR17 primer and DNTPs are added to anneal the primer. SHAPE reverse transcription master mix is then added to each sample and incubated at 45° C. for 3 hours for reverse transcription of the RNA. The resulting cDNA is isolated by treating the samples with ExoSAP-IT and removing the RNA. cDNA is then cleaned with Silane magnetic beads and 5' cDNA linker was ligated on the beads.

For all protocol types, cDNA was quantified with quantitative PCR (qPCR) followed by amplification and gel purification of libraries. A cDNA pPCR master mix was prepared and added to each cDNA sample in a 384 well plate. Libraries were amplified according to PCT protocol and then cleaned up with AmpureXP beads. The cDNA library was purified using agarose gel to separate library samples. Libraries were then extracted from the gel with Qiagen MinElute gel extraction kit, and quantitated and sequenced.

Example 2

Figure 1A:
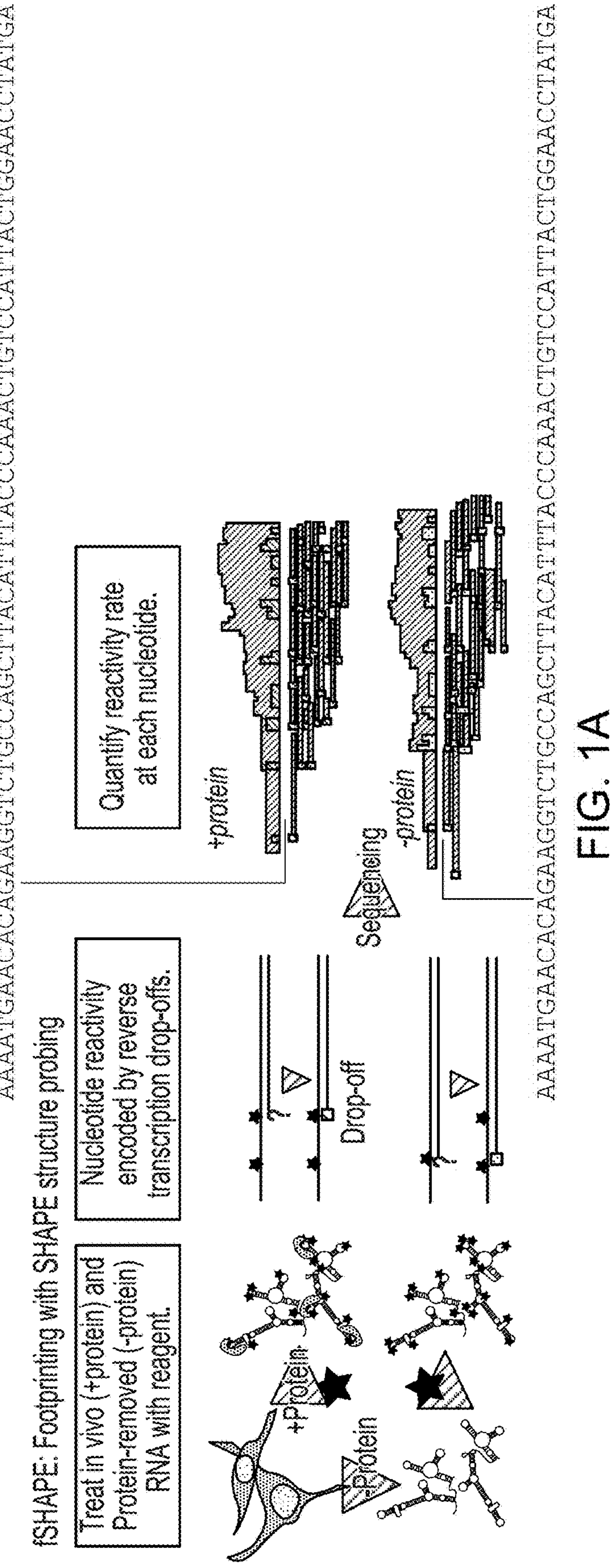
FIG. 1A is an exemplary schematic showing that fSHAPE requires two RNA samples processed in parallel: a "+protein" samples in which cellular RNA is treated with the probing reagent (star) and a "−protein" sample in which RNA is extracted from cells, stripped of protein, and treated with the probing reagent. Nucleotides that react with the reagent form adducts that result in drop-off events during reverse transcription, such that the frequency of drop-off events at a given nucleotide is proportional to its reactivity rate with the probing reagent. "+protein" drop-off frequencies are subtracted from "−protein" drop-off frequencies and normalized to obtain an fSHAPE reactivity value at each nucleotide describing its degree of increased reactivity with the reagent in the absence of protein, akin to footprinting.
Figure 1A:
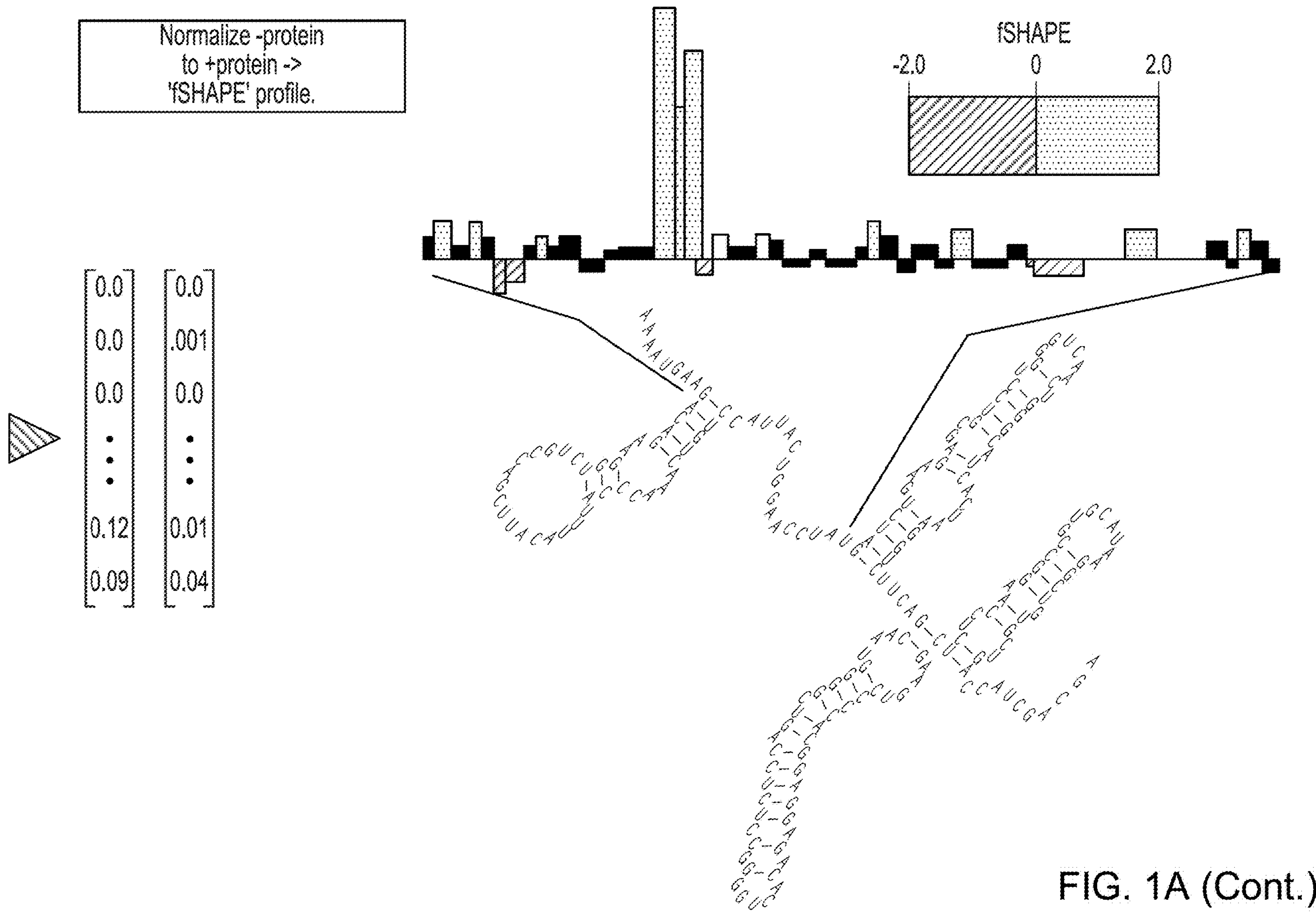
Figures 2A, 2B:
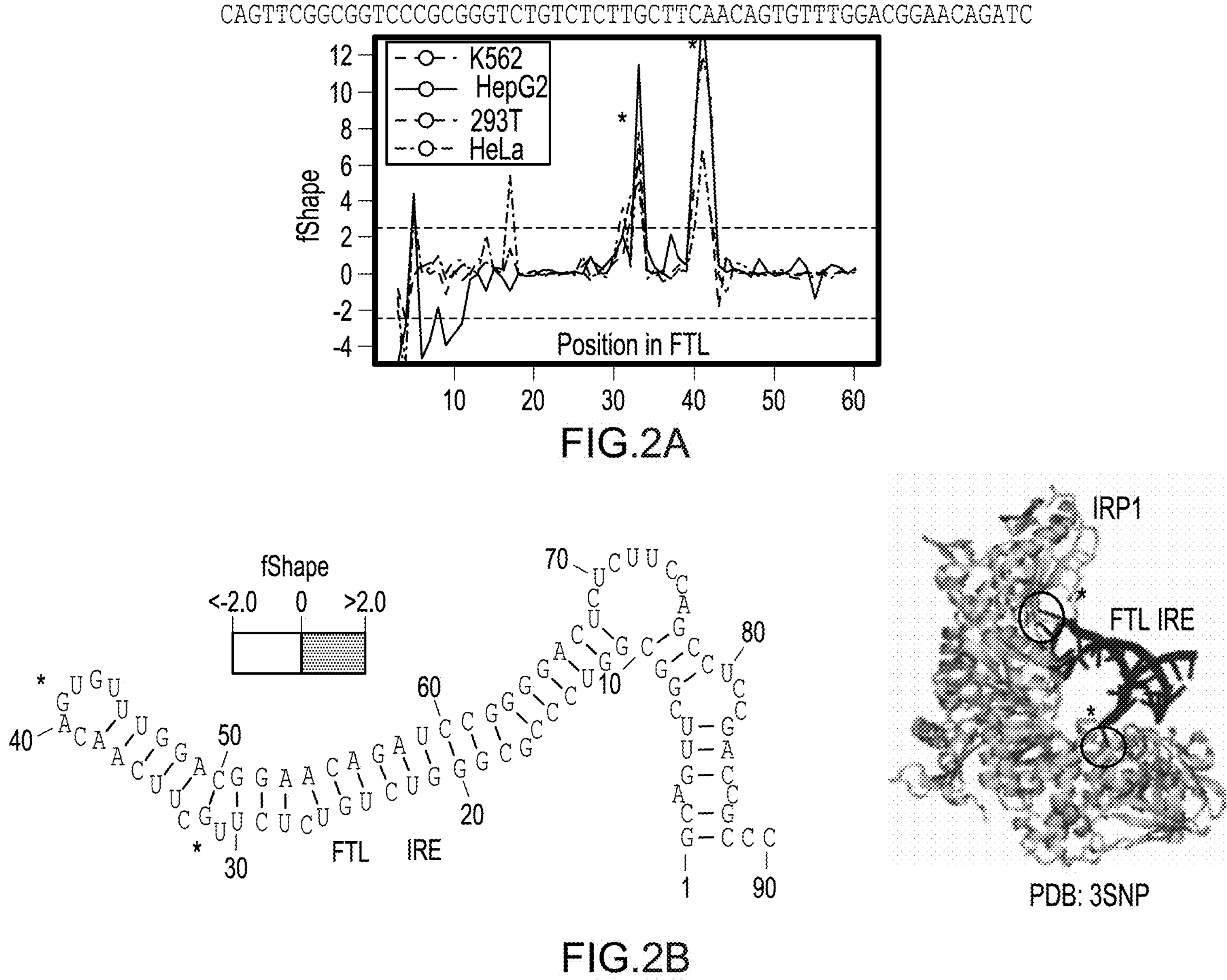
FIG. 2A shows exemplary fSHAPE reactivities from four cell types across the iron response element in the Ferritin light chain (FTL) transcript.
FIG. 2B shows the predicted secondary structure of the FTL iron response element (left), and numbered by position in FTL transcript NM_000146. Asterisks indicate bases known to hydrogen bond with iron response element binding protein (IRP1), based on the crystal structure (right; PDBID: 3SNP) of IRP1 bound to the FTL iron response element.

Footprinting with SHAPE (fSHAPE) Transcriptome-Wide in Human Cells fSHAPE reactivities were measured transcriptome-wide in duplicate on K562, HepG2, 293T, and HeLa cell lines, with good correlations between replicates (FIG. 7). The fSHAPE strategy successfully produces protein footprints on RNA by comparing in vivo (+protein) probed transcripts to protein-removed (−protein) probed transcripts (FIG. 1A). fSHAPE dispenses the need for the additional untreated sample used in other SHAPE footprinting experiments, as correlations between fSHAPE reactivities produced with the untreated sample versus without are very high (FIG. 8). fSHAPE reactivities in relation to known examples of RNA-protein interaction sites were first studied, such as the iron response element (IRE) in ferritin light chain (FTL) which binds iron response proteins. fSHAPE reactivity profiles in the FTL IRE display consistently prominent spikes in the RNA element's highly conserved apical loop and bulge, which have been structurally characterized contacting iron response protein (FIGS. 2A-2B).

Example 3

Interpreting fSHAPE Reactivities

Existing structures of human RBP-RNA complexes allow evaluation of how accurately fSHAPE reactivities detect RBP interactions with RNA nucleotides. 10 RNA-protein x-ray crystallography structures corresponding to transcript regions that also have fSHAPE data were curated. It was determined the hydrogen bonds and their bond lengths formed with the base, 2'-OH, or backbone atoms (FIG. 3A) of each nucleotide in the structures in order to quantify the "ground-truth" set of RNA-protein interactions. To determine which types of interactions (protein-RNA base, protein-RNA backbone, and/or protein-RNA sugar) fSHAPE values most correlate with, fSHAPE reactivities against several models of hydrogen bond interactions were compared in the ground-truth structures. Optimal hydrogen bond lengths for each model were fit to fSHAPE reactivities by maximizing receiver operator characteristic (ROC) curve performance (FIG. 3C). The best performing yet most parsimonious model achieves an area under the curve (AUC) of 0.82 and indicates that high fSHAPE values are highly correlated to RNA nucleotides that do not pair with other RNA nucleotides (within 3.0 Å) and whose base moieties hydrogen bond with protein within 3.0 Å (FIG. 3B). This model sheds light on how the probing reagent used to generate fSHAPE data, NAI-N3, reacts with RNA in the presence of protein. Consistent with its use in structure probing, the reagent does not appear to react with nucleotides whose bases hydrogen bond with other RNA bases in a base-pair, but also does not react with RNA whose bases hydrogen bond with protein. Thus, protein residues that interact with RNA "protect" RNA bases from the reagent by pairing with them, rather than stearic hindrance alone. The reagent does not differentially detect bases that pair with both protein and RNA, or backbone and 2'-OH moieties that pair with protein. Thus fSHAPE does not detect binding sites that typically use these modes of interaction, such as sites bound by double-stranded RNA binding proteins. It is unexpected that fSHAPE does not appear to detect sugar moieties that hydrogen bond with proteins, given that the probing reagent directly reacts with the 2'-OH.

However, this is consistent with the reagent's use in structure probing, in which reactivity with the 2'-OH is highly correlated with the flexibility of the adjacent base and is used to indicate the paired state of the base.

Example 4 fSHAPE Reactivities in the Context of RNA Structure

Consistent with its ability to detect protein-bound bases that are otherwise unpaired (FIGS. 3A-3C), it was assessed if high fSHAPE values correspond to unpaired bases transcriptome-wide (FIG. 4A-4C). For example, the structural model of the human MYC (c-myc) internal ribosome entry site (IRES) shows high fSHAPE reactivities almost exclusively in bulges and loops (FIG. 4A), particularly in the apical loops with demonstrated contributions to IRES-mediated translational control. Selecting for 200 nucleotides regions around bases with the strongest fSHAPE signals, base pairing probabilities were calculated for these regions via computational structure prediction supported by structure probing data in the same cell lines. This yielded 10,000 non-overlapping regions with K562 fSHAPE data and 3,000-5,000 regions in the other cell lines. Separating bases in these regions into low, middle, and high fSHAPE reactivities, it was observed that these bases occupy dramatically different sets of corresponding base pairing probabilities (FIG. 4B and FIG. 9). As expected, bases with the highest fSHAPE reactivities are predominantly predicted to have a low probability of base pairing, i.e. are unpaired (FIG. 4B). Bases with intermediate fSHAPE reactivities, that is, no difference in reactivity between in vivo and protein-removed conditions of structure probing, predominantly correspond to high base pairing probabilities (FIG. 4B). Bases with very low fSHAPE reactivities are more difficult to interpret. They may represent structurally dynamic nucleotides that become single-stranded upon RBP binding, and thus these types of nucleotides occupy both paired and unpaired states with equal frequencies (FIG. 4B).

Additionally, previous structure probing experiments have observed that A and U nucleotides tend to be less frequently base-paired than G and C, and this result is reproduced among fSHAPE reactivities (FIG. 10). However, higher fSHAPE reactivities among A and U nucleotides may also suggest that these bases hydrogen bond with protein more frequently, as observed among large numbers of RNA-protein crystal structures and in binding motifs determined by RNA Bind-N-Seq experiments. fSHAPE reactivities are thus in line with the known chemistry of SHAPE structure probing, while also revealing trends in the chemistry of RBP binding.

The Shannon entropy of nucleotides with high fSHAPE reactivities was further assessed in order to understand the larger structural context of regions that bind RBPs. Shannon entropy describes the density of the ensemble of secondary structures that an RNA region forms, where low Shannon entropy values indicate stable structural regions and high Shannon entropies indicate more dynamic regions of RNA. Shannon entropies in the same regions used for base pairing probability regions were calculated and the Shannon entropies were averaged in a 50 nucleotide window around bases with high fSHAPE values, as well as in their 50 nucleotide flanking regions for comparison. It was found that Shannon entropies are significantly lower in transcript regions with high fSHAPE values as compared to flanking regions (FIG. 4C and FIG. 11). This suggests that the RNA-protein interactions detected by fSHAPE tend to occur in the overarching context of stable structural elements. Indeed, stable RNA stems presenting RBP binding sites in unstructured loops is a common mode of interaction with proteins.

Example 5 fSHAPE Reactivity Patterns Predict RBP Interaction Sites

Patterns in fSHAPE reactivity profiles were used to predict interaction sites with iron response proteins 1 and 2 (IRP1 and IRP2) transcriptome-wide. IRP1 and IRP2 binding to the iron response element (IRE) in FTL is well-characterized, the former of which is measured binding the IRE with picomolar affinity. The IRE consists of a bulge-stem-loop structure with conserved bases in the bulge and apical loop that hydrogen bond with iron response protein, whose binding to an IRE in the 5'UTR regulates translation and binding in the 3'UTR regulates degradation of the transcript. Additional IREs have been discovered in the untranslated regions of multiple genes, implying that many more IREs may await detection. It was reasoned that the clear pattern of fSHAPE reactivities in the IRE of FTL (FIGS. 2A-2B) and its highly conserved sequence would enable a simple search for IREs transcriptome-wide. This strategy first searches the transcriptome for the conserved IRE motif sequence, then compares the pattern of fSHAPE reactivities for each match to the pattern of fSHAPE reactivities in the FTL IRE. Matches whose correlation with the FTL IRE exceeds 0.8 and whose bulge and apical loop bases have sufficiently high fSHAPE reactivities were selected as candidate IREs (FIG. 5A). IREs identified by this algorithm include known IREs in FTH1, ALAS2, and multiple IREs in TFRC (5 out of 7 known human IREs with available fSHAPE data) in addition to novel putative IREs (FIG. 5B and FIGS. 12A-12C). Putative IREs from CDC34, H19, SLC2A4RG, and COASY were selected and tested for IRP binding via electrophoretic mobility shift assay (EMSA), all demonstrating binding to IRP1 and/or IRP2 by comparison to FTL, which reliably binds either IRP1 or IRP2 depending on cellular conditions (FIG. 5C and FIG. 16). The IREs in CDC34 and SLC2A4RG are surprisingly found in the coding regions, while the IRE is in the 3'UTR of COASY and near the 3' end of H19, which is noncoding. All previously known IREs have been found in UTRs, although IREs have been predicted in the coding sequence of a few transcripts. To further test how these IRE candidates respond at the transcriptional level to cellular iron levels, K562 cells were supplemented with either an iron source (ferric ammonium citrate; FAC) or an iron chelator (deferoxamine mesylate; DFOM) for 24 hours and CDC34, COASY, and SLC2A4RG transcript abundance was measured via quantitative RT-PCR (H19 is not expressed in K562 cells).

TFRC, which is known to be negatively regulated by high cellular iron at the transcriptional level, was also measured as a positive control. TFRC transcript abundance relative to housekeeping gene RPL4 strongly increased in response to DFOM and decreased in response to FAC, as expected (FIG. 13). CDC34 responded in a similar manner as TFRC, indicating that this transcript is protected by IRPs under low iron conditions. CDC34 is an E2 ubiquitin conjugating enzyme without reported links to iron metabolism, except that IRP2 itself is degraded by the ubiquitin pathway in the presence of high cellular iron. It was found that CDC34 levels increase in the presence of DFOM (FIG. 13). CDC34 binding by IRP2 suggests a feedback loop whereby CDC34 transcripts are protected from decay by IRP2 (FIG. 5C) and also indirectly check IRP2 protein levels, and CDC34 transcript levels increase following extended low iron conditions that increase IRP2 availability. SLC2A4RG and COASY also demonstrate significant changes under low iron conditions, albeit in the opposite direction compared to TFRC and CDC34 (FIG. 13).

Decreased transcript abundance under low iron conditions—when IRPs are available for binding—suggests a mechanism in which these transcripts are degraded upon IRP recruitment by their IREs, which is contrary to known IRP mechanisms. SLC2A4RG produces a transcription factor that regulates SLC2A4 expression, reflecting several members of the solute carrier (SLC) gene family known to harbor IREs. COASY produces an enzyme whose loss is linked to brain iron accumulation through an unknown mechanism. H19 is an unconventional IRE candidate as a noncoding RNA, although the known IRE-containing gene SLC11A2 also produces a noncoding transcript variant (NCBI ID: NR_033421) that contains the same IRE sequence as its coding variant siblings. Recent evidence linking H19 to an inverse relationship with known iron regulator FTH1 argues for a functional role for its IRE, which likely recruits IRP1 to its 3' end to regulate H19 abundance.

Example 6

SHAPE-eCLIP and fSHAPE-eCLIP Application

Figure 1B:
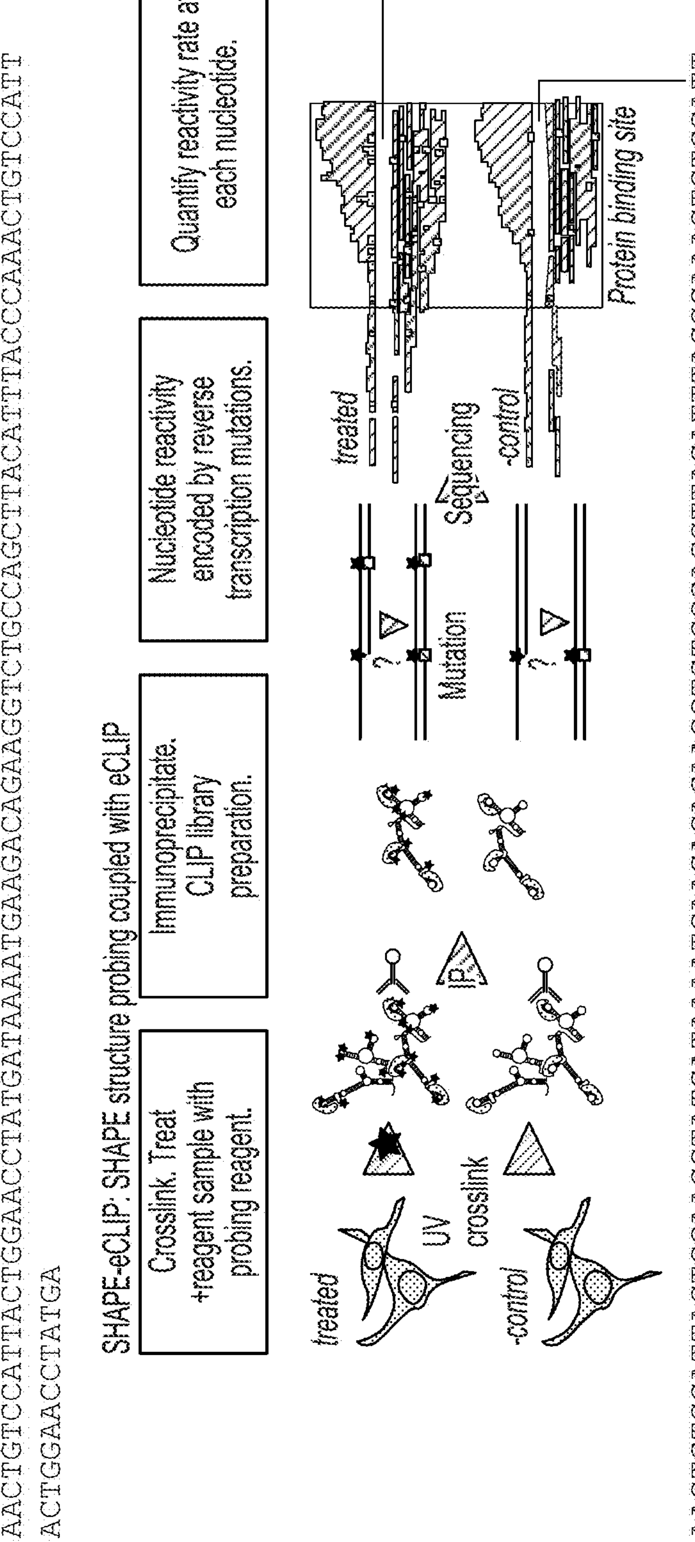
FIG. 1B is an exemplary schematic showing SHAPE-CLIP probes secondary structure in transcripts selected by CLIP. Cell samples are either treated with a structure probing reagent (star) or an untreated negative control sample. Samples are UV crosslinked and extracted protein-bound transcripts are immunoprecipitated (IP) with an antibody to the desired protein. Nucleotides that react with the reagent form adducts that result in mutations during a modified reverse transcription, such that the frequency of sequenced mutations at a given nucleotide is proportional to its reactivity rate with the probing reagent. "Treated" sample mutation rates are subtracted from "−control" mutation rates and normalized to obtain a SHAPE reactivity value at each nucleotide. Sequencing reads are also be used to determine protein binding sites.
Figure 1B:
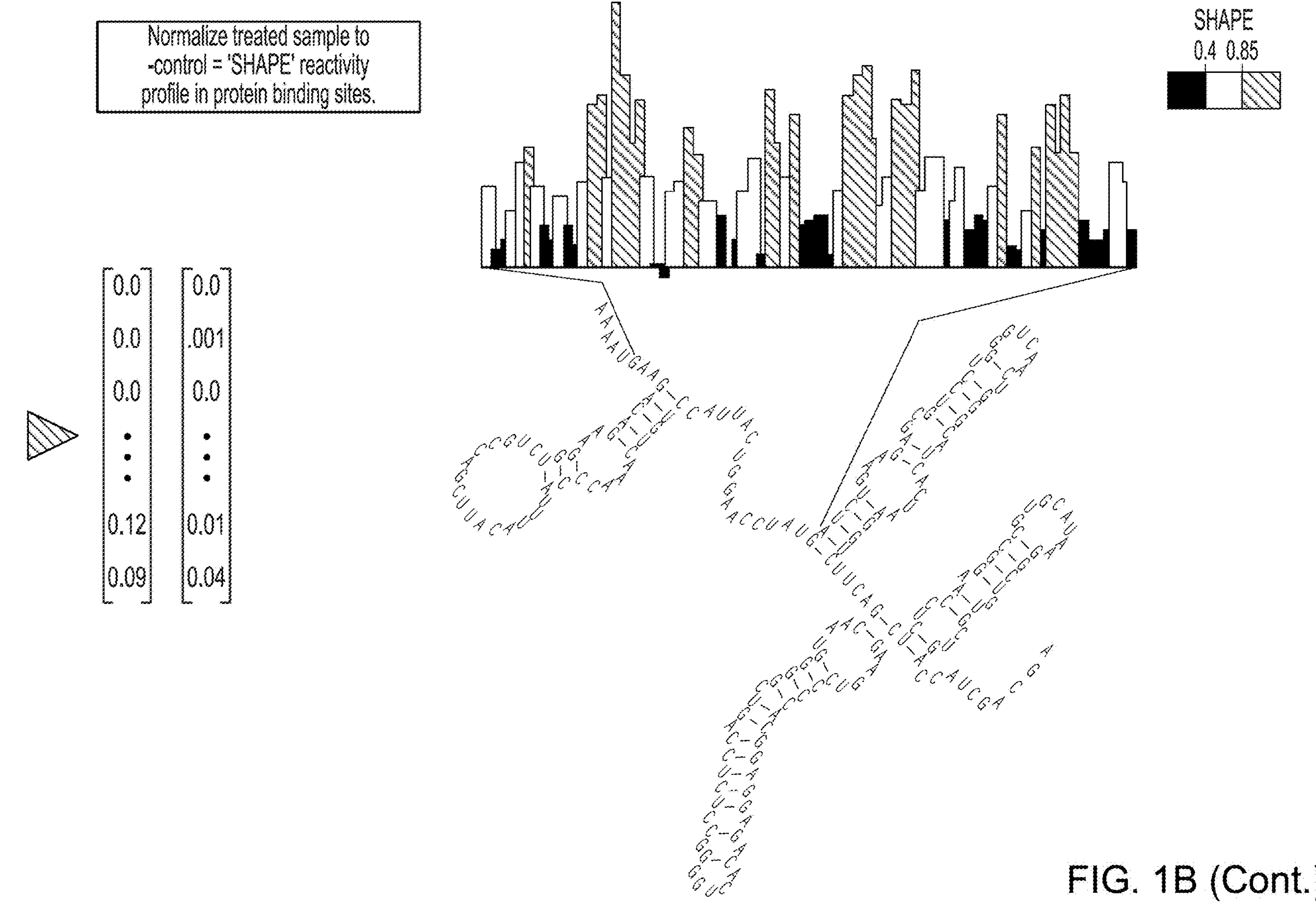
Figure 1C:
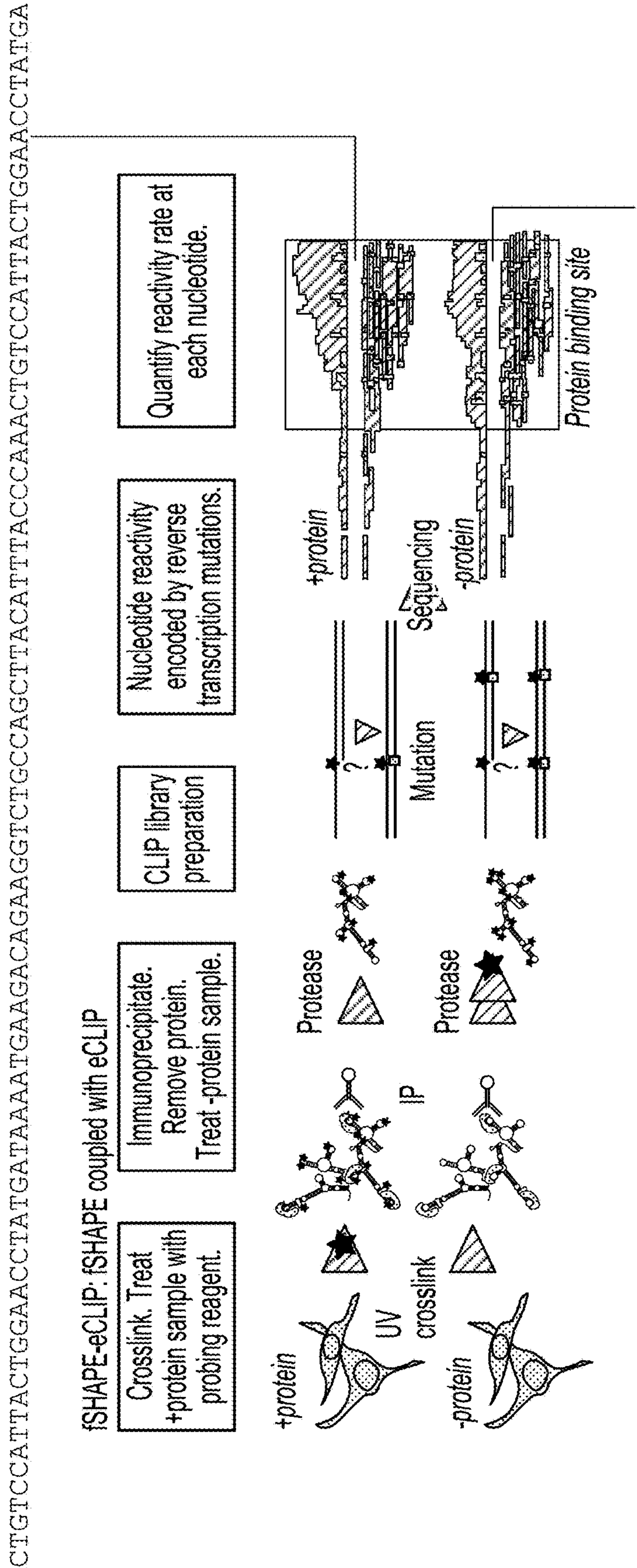
FIG. 1C is an exemplary schematic showing that fSHAPE-CLIP identifies nucleotides bound by protein in transcripts selected by CLIP. Cell samples are either initially treated with a structure probing reagent ("+protein") or untreated ("−protein"). Samples are UV crosslinked and extracted protein-bound transcripts are immunoprecipitated (IP) with an antibody to the desired protein. RNA is protease-treated and refolded; the "−protein" samples is treated with the structure probing reagent. Nucleotides that react with the reagent form adducts that result in mutations during a modified reverse transcription, such that the frequency of sequenced mutations at a given nucleotide is proportional to its reactivity rate with the probing reagent. "+protein" sample mutation rates are subtracted from "−protein" mutation rates and normalized to obtain an fSHAPE reactivity value at each nucleotide. Sequencing reads are also be used to determine protein binding sites.

The use of enhanced crosslinking and immunoprecipitation (eCLIP) to selectively probe transcript regions bound by an RBP of interest was next explored with SHAPE-and fSHAPE-eCLIP (FIGS. 1B-1C). fSHAPE-eCLIP was developed to identify protein-interacting nucleotides in transcripts specifically bound by an RBP of interest, and SHAPE-eCLIP to more effectively interrogate the structural motifs that recruit RBPs, since RNA sequence motifs alone do not account for many protein binding events. To validate SHAPE- and fSHAPE-eCLIP approaches they were applied to stem loop binding protein (SLBP) (FIGS. 14A-14C). SLBP is structurally well characterized binding stem loop elements at the 3' ends of histone mRNAs, and published eCLIP binding sites for SLBP reiterates this association. Binding sites identified for both SHAPE-eCLIP and fSHAPE-eCLIP closely match known eCLIP binding sites for SLBP, demonstrating that modifications to eCLIP implemented for SHAPE and fSHAPE techniques did not interfere with immunoprecipitation of SLBP-bound transcripts (FIGS. 6A-6B). Two structure probing reagents, dimethyl sulfate (DMS) and 2-methylnicotinic acid imidazolide (NAD, were tested with SHAPE-CLIP to gauge the compatibility of various reagents with eCLIP. DMS yields structure information on adenine and cytosine nucleotides; NAI yields on all four nucleotides (FIG. 1C). Both reagents were successfully implemented in SHAPE-eCLIP, but because NAI returns information on all nucleotides this reagent was chosen for implementation in fSHAPE-eCLIP. SHAPE-eCLIP accurately and consistently returns low SHAPE reactivities in the stems of histone mRNA stem loop elements (FIG. 6C and FIG. 14C), as expected. However, SHAPE-eCLIP reactivities are also consistently low in the apical loop of histone stem loop elements which are unpaired and thus expected to display high SHAPE reactivities. The loop reactivities are much lower than expected because the bases hydrogen bond with SLBP and 3'hExonuclease (FIG. 6D), dampening their reactivity with the probing reagent in the same manner as a base pair. High (SHAPE-eCLIP reactivities in these loops confirm this interpretation (FIG. 6D).

fSHAPE-eCLIP reactivities across multiple histone mRNA stem loops reveal higher reactivities in the apical loop and the single-stranded region 5' to the loop, whose bases hydrogen bond with SLBP and its binding partner 3'hExonuclease (FIGS. 6D-6E, lower). Additionally, (SHAPE reactivities in the apical loop are their maximal at the uracil nucleotides previously identified to be most sequence-conserved in the context of SLBP binding. By comparison, CLIP-seq methods use nucleotide crosslinking rates in RBP binding sites as a proxy indicator of the nucleotide-specific protein interaction site. However, the occurrence of crosslinking is restricted to aromatic amino acids and predominantly uracil and cytosine nucleotides.

Thus crosslinking sites do not necessarily coincide with the select nucleotides that form molecular bonds with protein. For example, nucleotides that display the highest crosslinking rate in eCLIP SLBP binding sites are upstream of the stem loop elements that actually binds SLBP (FIG. 6E, upper), contrasting with fSHAPE-eCLIP reactivities that peak in the stem loops of histone transcripts (FIG. 6E, lower). In summary, SHAPE-eCLIP and fSHAPE-eCLIP successfully select for and probe transcript regions bound SLBP, corroborating details of the regions' structure and protein interactions, which are intimately linked.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of identifying an RNA nucleobase that interacts with an RNA binding protein (RBP), the method comprising:

(a) providing a biological sample, wherein the biological sample comprises a first plurality of cells and a second plurality of cells;

(b) contacting the first plurality of cells with an RNA structure probing agent;

(c) crosslinking the RNA binding protein to an RNA fragment in both the first plurality of cells and the second plurality of cells;

(d) detecting an RNA-RBP complex in both the first plurality of cells and the second plurality of cells, wherein the RNA-RBP complex comprises the RNA fragment bound by the RNA binding protein;

(e) isolating the RNA fragment of the RNA-RBP complex in both the first plurality of cells and the second plurality of cells;

(f) contacting the second plurality of cells with the RNA structure probing agent; and (g) profiling (i) the RNA fragment bound by the RNA binding protein from the first plurality of cells and (ii) the RNA fragment bound by the RNA binding protein from the second plurality of cells, thereby identifying the RNA nucleobase(s) of the RNA fragment that interact with the RNA binding protein via a hydrogen bond, wherein steps (a)-(g) are completed in the order presented.

2. The method of claim 1, wherein the crosslinking comprises formaldehyde crosslinking, UV crosslinking, psoralen crosslinking, or combinations thereof.

3. The method of claim 1, wherein the detecting step (d) further comprises contacting the RNA-RBP complex with an RBP specific antibody, and immunoprecipitating the RNA-RBP complex using the RBP specific antibody.

4. The method of claim 3, wherein the isolating step (e) further comprises treating the immunoprecipitated RNA-RBP complex with a protease.

5. The method of claim 1, wherein the profiling step (g) further comprises sequencing all or a part of a sequence of the isolated RNA fragment or a complement thereof.

6. The method of claim 1, wherein the RNA structure probing reagent comprises 2-methylnicotinic acid imidazolide (NAI), dimethyl sulfate (DMS), 1-methyl-7-nitroisatoic anhydride (1M7), 1-methyl-6-nitroisatoic anhydride (1M6), N-methylisatoic anhydride (NMIA), 2-methylnicotinic acid imidazolide-azide (NAI-N3), Nicotinoyl azide (NaZ), Nicotinoyl azide (NaZ-N3), 2-aminopyridine-3-carboxylic acid imidazolide (2A3), Carbodiimide N-cyclohexyl-N'-(2-morpholinoethyl) carbodiimide metho-p-toluenesulfonate (CMC), Isoquinoline-6-carboxylic acid imidazolide (I6), Indoline-5-carboxylic acid imidazolide (15), 1-Methylimidazole-4-carboxylic acid imidazolide (1M4), 6-Aminopyridine-3-carboxylic acid imidazolide (6A3), Benzotriazole-5-carboxylic acid imidazolide (B5), Nicotinic acid imidazolide (NIC), 3-Azaisatoic anhydride (3AIA), 2-methyl-3-furoic acid imidazolide (FAI), 2-methyl-3-furoic acid imidazolide-azide (FAI-N3), N-propanone isatoic anhydride (NPIA), 5-nitroisatoic anhydride (5NIA), azido-kethoxal (N3-kethoxal), Glyoxal, Methylglyoxal, Phenylglyoxal, 1-ethyl-3-(3-dimethylaminopropyl) carbodiimide (EDC), 4'-aminomethyltrioxalen (AMT), Psoralen-triethylene glycol azide, or Amotosalen.

* * * * *